(12) United States Patent
Obika et al.

(10) Patent No.: US 12,104,154 B2
(45) Date of Patent: Oct. 1, 2024

(54) ANTISENSE OLIGONUCLEIC ACID

(71) Applicant: Osaka University, Suita (JP)

(72) Inventors: Satoshi Obika, Suita (JP); Reiko Waki, Suita (JP); Takao Inoue, Suita (JP); Tokuyuki Yoshida, Suita (JP); Kunihiko Morihiro, Suita (JP); Yuya Kasahara, Suita (JP); Atsushi Mikami, Suita (JP)

(73) Assignee: Osaka University, Suita (JP)

( * ) Notice: Subject to any disclaimer, the term of this patent is extended or adjusted under 35 U.S.C. 154(b) by 67 days.

(21) Appl. No.: 17/666,341

(22) Filed: Feb. 7, 2022

(65) Prior Publication Data

US 2022/0170020 A1 Jun. 2, 2022

Related U.S. Application Data

(62) Division of application No. 16/487,762, filed as application No. PCT/JP2018/006061 on Feb. 20, 2018, now Pat. No. 11,261,440.

(30) Foreign Application Priority Data

Feb. 21, 2017 (JP) ................. 2017-030489

(51) Int. Cl.
 *C12N 15/113* (2010.01)
 *A61K 31/7115* (2006.01)
 *A61K 31/712* (2006.01)

(52) U.S. Cl.
 CPC ........ *C12N 15/113* (2013.01); *A61K 31/7115* (2013.01); *A61K 31/712* (2013.01)

(58) Field of Classification Search
 CPC ............... C12N 15/113; A61K 31/7115; A61K 31/712
 See application file for complete search history.

(56) References Cited

U.S. PATENT DOCUMENTS

| | | |
|---|---|---|
| 8,541,562 B2 | 9/2013 | Obika et al. |
| 9,597,632 B2 | 3/2017 | Okada et al. |
| 9,611,479 B2 | 4/2017 | Obika et al. |
| 10,377,789 B2 | 8/2019 | Obika et al. |
| 11,261,440 B2 | 3/2022 | Obika et al. |
| 2008/0015162 A1 | 1/2008 | Bhanot et al. |
| 2010/0197762 A1 | 8/2010 | Swayze |
| 2014/0303235 A1 | 10/2014 | Oestergaard et al. |
| 2014/0309279 A1 | 10/2014 | Oestergaard et al. |
| 2014/0323707 A1 | 10/2014 | Seth et al. |
| 2015/0051389 A1 | 2/2015 | Seth et al. |
| 2015/0337002 A1 | 11/2015 | Obika et al. |
| 2015/0376625 A1 | 12/2015 | Oestergaard et al. |
| 2016/0160280 A1 | 6/2016 | Burel |
| 2017/0130224 A1 | 5/2017 | Oestergaard et al. |
| 2017/0182082 A1 | 6/2017 | Swayze |
| 2019/0338281 A1 | 11/2019 | Seth et al. |
| 2020/0055890 A1 | 2/2020 | Obika et al. |
| 2020/0056178 A1 | 2/2020 | Obika et al. |
| 2020/0056187 A1 | 2/2020 | Oestergaard et al. |
| 2020/0276221 A1 | 9/2020 | Swayze |

FOREIGN PATENT DOCUMENTS

| | | |
|---|---|---|
| JP | H08-508493 A | 9/1996 |
| JP | 2016-096826 A | 5/2016 |
| WO | WO 1994/022892 A1 | 10/1994 |
| WO | WO 2008/049085 A1 | 4/2008 |
| WO | WO 2011/052436 A1 | 5/2011 |
| WO | WO 2013/022966 A1 | 2/2013 |
| WO | WO 2013/118776 A1 | 8/2013 |
| WO | WO 2014/046212 A1 | 3/2014 |
| WO | WO 2014/112463 A1 | 7/2014 |
| WO | WO 2014/121287 A1 | 8/2014 |
| WO | WO 2015/125783 A1 | 8/2015 |
| WO | WO 2016/017422 A1 | 2/2016 |
| WO | WO 2017/053722 A1 | 3/2017 |
| WO | WO 2018/106566 A1 | 6/2018 |
| WO | WO 2018/155451 A1 | 8/2018 |

OTHER PUBLICATIONS

U.S. Appl. No. 16/487,762, filed Aug. 21, 2019.
Burdick et al., "Sequence motifs associated with hepatotoxicity of locked nucleic acid—modified antisense oligonucleotides," *Nucleic Acids Res.*, 42(8): 4882-4891 (2014).
Hagedom et al., "Hepatotoxic Potential of Therapeutic Oligonucleotides Can Be Predicted from Their Sequence and Modification Pattern," *Nucleic Acid Ther.*, 23(5): 302-310 (2013).
Merits, "New antisense inhibitors of hepatitis C virus," *J. Antivir. Antiretrovir.*, 3(4): 165 (2011).
Mutso et al., "RNA Interference-Guided Targeting of Hepatitis C Virus Replication with Antisense Locked Nucleic Acid-Based Oligonucleotides Containing 8-oxo-dG Modifications," *PLoS One*, 10(6): e0128686 (2015).
Prakash et al., "Antisense Oligonucleotides Containing Conformationally Constrained 2',4'-(N-Methoxy)aminomethylene and 2',4'-Aminooxymethylene and 2'-O,4'-C-Aminomethylene Bridged Nucleoside Analogues Show Improved Potency in Animal Models," *J. Med. Chem.*, 53(4): 1636-1650 (2010).
Rosemeyer et al., "Oligonucleotides Incorporating 7-(Aminoalkynyl)-7-deaza-2'-deoxyguanosines: Duplex Stability and Phosphodiester Hydrolysis by Exonucleases," *Bioconjug. Chem.*, 13(6): 1274-1285 (2002).
Seth et al., "Short Antisense Oligonucleotides with Novel 2'-4' Conformationaly Restricted Nucleoside Analogues Show Improved Potency without Increased Toxicity in Animals," *J. Med. Chem.*, 52(1): 10-13 (2009).

(Continued)

*Primary Examiner* — J. E. Angell
(74) *Attorney, Agent, or Firm* — Leydig, Voit & Mayer, Ltd.

(57) ABSTRACT

The present invention aims to provide an antisense oligonucleic acid with reduced hepatotoxicity. The antisense oligonucleic acid according to the present invention is characterized in that it has a base length of not less than 7 nt and not more than 30 nt, wherein nucleic acid residues of not less than 1 nt and not more than 5 nt respectively from the both terminals are 2',4'-bridged nucleic acids, 2',4'-non-bridged nucleic acid residue(s) is(are) present between the above-mentioned both terminals, and one or more bases in the nucleic acid residue(s) of the above-mentioned 2',4'-non-bridged nucleic acid residue(s) is/are modified.

16 Claims, 30 Drawing Sheets

Specification includes a Sequence Listing.

(56) References Cited

OTHER PUBLICATIONS

Seth et al., "An Exocyclic Methylene Group Acts as a Bio-isostere of the 2'-Oxygen Atom in LNA," *J. Am. Chem. Soc.*, 132(42): 14942-14950 (2010).

Japanese Patent Office, International Search Report in International Patent Application No. PCT/JP2018/006061 (May 22, 2018).

(2) activity evaluation (1) hepatotoxicity test (ALT)

(2) activity evaluation (1) hepatotoxicity test (ALT)

(2) activity evaluation (1) hepatotoxicity test (ALT)

(2) activity evaluation (1) hepatotoxicity test (ALT)

```
                         SEQUENCE LISTING

<160> NUMBER OF SEQ ID NOS: 95

<210> SEQ ID NO 1
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 1
nnnatgccac cnnn                                                       14

<210> SEQ ID NO 2
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (7)..(7)
<223> OTHER INFORMATION: n stands for 5-hydroxycytidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
```

```
<220> FEATURE:
<221> NAME/KEY: modified_base
<222> LOCATION: (14)..(14)
<223> OTHER INFORMATION: n stands for 2',4'-bridged adenosine

<400> SEQUENCE: 2
nnnatgncac cnnn                                                                 14

<210> SEQ ID NO 3
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged adenosine
<220> FEATURE:
<221> NAME/KEY: modified_base
<222> LOCATION: (14)..(14)
<223> OTHER INFORMATION: n stands for 2',4'-bridged adenosine

<400> SEQUENCE: 3
nnncgcatgc cnnn                                                                 14

<210> SEQ ID NO 4
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged m5c
<220> FEATURE:
<221> NAME/KEY: modified_base
<222> LOCATION: (10)..(10)
<223> OTHER INFORMATION: n stands for 5-hydroxycytidine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged adenosine
<220> FEATURE:
<221> NAME/KEY: modified_base
<222> LOCATION: (14)..(14)
```

<223> OTHER INFORMATION: n stands for 2',4'-bridged adenosine

<400> SEQUENCE: 4
nnncgcatgn cnnn                                                         14

<210> SEQ ID NO 5
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged adenosine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 5
nnnatgccct annn                                                         14

<210> SEQ ID NO 6
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged adenosine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (7)..(7)
<223> OTHER INFORMATION: n stands for 5-hydroxycytidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

```
<400> SEQUENCE: 6
nnnatgncct annn                                                    14

<210> SEQ ID NO 7
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 7
nnntgcctcc gnnn                                                    14

<210> SEQ ID NO 8
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (6)..(6)
<223> OTHER INFORMATION: n stands for 5-hydroxycytidine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine
```

<400> SEQUENCE: 8
nnntgnctcc gnnn                                                             14

<210> SEQ ID NO 9
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged guanosine
<220> FEATURE:
<221> NAME/KEY: modified_base
<222> LOCATION: (14)..(14)
<223> OTHER INFORMATION: n stands for 2',4'-bridged guanosine

<400> SEQUENCE: 9
nnntctttac cnnn                                                             14

<210> SEQ ID NO 10
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged m5c
<220> FEATURE:
<221> NAME/KEY: modified_base
<222> LOCATION: (11)..(11)
<223> OTHER INFORMATION: n stands for 5-hydroxycytidine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged guanosine
<220> FEATURE:
<221> NAME/KEY: modified_base
<222> LOCATION: (14)..(14)
<223> OTHER INFORMATION: n stands for 2',4'-bridged guanosine

<400> SEQUENCE: 10
nnntctttac nnnn                                                     14

<210> SEQ ID NO 11
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (3)..(3)
<223> OTHER INFORMATION: n stands for 2',4'-bridged guanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged thymidine

<400> SEQUENCE: 11
nnntgctttg gnnn                                                     14

<210> SEQ ID NO 12
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (3)..(3)
<223> OTHER INFORMATION: n stands for 2',4'-bridged guanosine
<220> FEATURE:
<221> NAME/KEY: modified_base
<222> LOCATION: (6)..(6)
<223> OTHER INFORMATION: n stands for 5-hydroxycytidine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged thymidine

<400> SEQUENCE: 12
nnntgntttg gnnn                              14

<210> SEQ ID NO 13
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged m5c
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged m5c

<400> SEQUENCE: 13
nnnccaagtt cnnn                              14

<210> SEQ ID NO 14
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged m5c
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (4)..(4)
<223> OTHER INFORMATION: n stands for 5-hydroxycytidine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged m5c

```
<400> SEQUENCE: 14
nnnncaagtt cnnn                                                         14

<210> SEQ ID NO 15
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged m5c
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (11)..(11)
<223> OTHER INFORMATION: n stands for 5-hydroxycytidine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged m5c

<400> SEQUENCE: 15
nnnccaagtt nnnn                                                         14

<210> SEQ ID NO 16
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged m5c
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (11)..(11)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c

<400> SEQUENCE: 16
nngtgatgac nnn                                                          13

<210> SEQ ID NO 17
```

-continued

```
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged m5c
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (10)..(10)
<223> OTHER INFORMATION: n stands for 5-hydroxycytidine
<220> FEATURE:
<221> NAME/KEY: modified_base
<222> LOCATION: (11)..(11)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c

<400> SEQUENCE: 17
nngtgatgan nnn                                                      13

<210> SEQ ID NO 18
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged m5c
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (11)..(11)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c

<400> SEQUENCE: 18
nnccctcgcc nnn                                                      13

<210> SEQ ID NO 19
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged m5c
<220> FEATURE:
<221> NAME/KEY: modified_base
```

```
<222> LOCATION: (2)..(2)
<223> OTHER INFORMATION: n stands for 2',4'-bridged guanosine
<220> FEATURE:
<221> NAME/KEY: modified_base
<222> LOCATION: (7)..(7)
<223> OTHER INFORMATION: n stands for 5-hydroxycytidine
<220> FEATURE:
<221> NAME/KEY: modified_base
<222> LOCATION: (11)..(11)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c

<400> SEQUENCE: 19
nnccctngcc nnn                                                           13

<210> SEQ ID NO 20
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged m5c
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (9)..(9)
<223> OTHER INFORMATION: n stands for 5-hydroxycytidine
<220> FEATURE:
<221> NAME/KEY: modified_base
<222> LOCATION: (11)..(11)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c

<400> SEQUENCE: 20 nncccctcgnc nnn                                                          13

<210> SEQ ID NO 21
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged m5c
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (10)..(10)
<223> OTHER INFORMATION: n stands for 5-hydroxycytidine
<220> FEATURE:
```

```
<221> NAME/KEY: modified_base
<222> LOCATION: (11)..(11)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c

<400> SEQUENCE: 21
nnccctcgcn nnn                                                              13

<210> SEQ ID NO 22
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 22
nnnatgccac cnnn                                                             14

<210> SEQ ID NO 23
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (5)..(5)
<223> OTHER INFORMATION: n stands for thiocarbonylthymidine
<220> FEATURE:
<221> NAME/KEY: modified_base
<222> LOCATION: (12)..(12)
<223> OTHER INFORMATION: n stands for 2',4'-bridged m5c
```

```
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 23
nnnangccac cnnn                                                            14

<210> SEQ ID NO 24
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged adenosine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 24
nnnatgccct annn                                                            14

<210> SEQ ID NO 25
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged adenosine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (5)..(5)
<223> OTHER INFORMATION: n stands for 2-thiocarbonylthymidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
```

<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 25
nnnangccct annn                                                              14

<210> SEQ ID NO 26
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 26
nnntgcctcc gnnn                                                              14

<210> SEQ ID NO 27
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (4)..(4)
<223> OTHER INFORMATION: n stands for 2-thiocarbonylthymidine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 27
nnnngcctcc gnnn                                                              14

<210> SEQ ID NO 28
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged guanosine
<220> FEATURE:
<221> NAME/KEY: modified_base
<222> LOCATION: (14)..(14)
<223> OTHER INFORMATION: n stands for 2',4'-bridged guanosine

<400> SEQUENCE: 28
nnntctttac cnnn                                                              14

<210> SEQ ID NO 29
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged m5c
<220> FEATURE:
<221> NAME/KEY: modified_base
<222> LOCATION: (4)..(4)
<223> OTHER INFORMATION: n stands for 2-thiocarbonylthymidine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged guanosine
<220> FEATURE:
<221> NAME/KEY: modified_base
<222> LOCATION: (14)..(14)
<223> OTHER INFORMATION: n stands for 2',4'-bridged guanosine

```
<400> SEQUENCE: 29
nnnnctttac cnnn                                                    14

<210> SEQ ID NO 30
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (3)..(3)
<223> OTHER INFORMATION: n stands for 2',4'-bridged guanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged thymidine

<400> SEQUENCE: 30
nnntgctttg gnnn                                                    14

<210> SEQ ID NO 31
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (3)..(3)
<223> OTHER INFORMATION: n stands for 2',4'-bridged guanosine
<220> FEATURE:
<221> NAME/KEY: modified_base
<222> LOCATION: (4)..(4)
<223> OTHER INFORMATION: n stands for 2-thiocarbonylthymidine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged thymidine

<400> SEQUENCE: 31
nnnngctttg gnnn                                                    14
```

```
<210> SEQ ID NO 32
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged m5c
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (11)..(11)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c

<400> SEQUENCE: 32
nngtgatgac nnn                                                    13

<210> SEQ ID NO 33
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged m5c
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (4)..(4)
<223> OTHER INFORMATION: n stands for 2-thiocarbonylthymidine
<220> FEATURE:
<221> NAME/KEY: modified_base
<222> LOCATION: (11)..(11)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c

<400> SEQUENCE: 33
nngngatgac nnn                                                    13

<210> SEQ ID NO 34
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
```

```
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 34
nnnatgccac cnnn                                                         14

<210> SEQ ID NO 35
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (6)..(6)
<223> OTHER INFORMATION: n stands for 8-aminoguanosine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 35
nnnatnccac cnnn                                                         14

<210> SEQ ID NO 36
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
```

```
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged adenosine
<220> FEATURE:
<221> NAME/KEY: modified_base
<222> LOCATION: (14)..(14)
<223> OTHER INFORMATION: n stands for 2',4'-bridged adenosine

<400> SEQUENCE: 36
nnncgcatgc cnnn                                                    14

<210> SEQ ID NO 37
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged m5c
<220> FEATURE:
<221> NAME/KEY: modified_base
<222> LOCATION: (9)..(9)
<223> OTHER INFORMATION: n stands for 8-aminoguanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged adenosine
<220> FEATURE:
<221> NAME/KEY: modified_base
<222> LOCATION: (14)..(14)
<223> OTHER INFORMATION: n stands for 2',4'-bridged adenosine

<400> SEQUENCE: 37
nnncgcatnc cnnn                                                    14

<210> SEQ ID NO 38
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged adenosine
<220> FEATURE:
```

```
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 38
nnnatgccct annn                                                        14

<210> SEQ ID NO 39
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged adenosine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (6)..(6)
<223> OTHER INFORMATION: n stands for 8-aminoguanosine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 39
nnnatnccct annn                                                        14

<210> SEQ ID NO 40
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged adenosine
```

```
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 40
nnntgcctcc gnnn                                                          14

<210> SEQ ID NO 41
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (5)..(5)
<223> OTHER INFORMATION: n stands for 8-aminoguanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 41
nnntncctcc gnnn                                                          14

<210> SEQ ID NO 42
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (12)..(12)
```

```
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 42
nnnatgccac cnnn                                                         14

<210> SEQ ID NO 43
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (6)..(6)
<223> OTHER INFORMATION: n stands for 8-bromoguanosine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 43
nnnatnccac cnnn                                                         14

<210> SEQ ID NO 44
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
```

```
<222> LOCATION: (13)..(13)
<223> OTHER INFORMATION: n stands for 2',4'-bridged adenosine
<220> FEATURE:
<221> NAME/KEY: modified_base
<222> LOCATION: (14)..(14)
<223> OTHER INFORMATION: n stands for 2',4'-bridged adenosine

<400> SEQUENCE: 44
nnncgcatgc cnnn                                                            14

<210> SEQ ID NO 45
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged m5c
<220> FEATURE:
<221> NAME/KEY: modified_base
<222> LOCATION: (9)..(9)
<223> OTHER INFORMATION: n stands for 8-bromoguanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged adenosine
<220> FEATURE:
<221> NAME/KEY: modified_base
<222> LOCATION: (14)..(14)
<223> OTHER INFORMATION: n stands for 2',4'-bridged adenosine

<400> SEQUENCE: 45
nnncgcatnc cnnn                                                            14

<210> SEQ ID NO 46
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged adenosine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
```

```
<221> NAME/KEY: modified_base
<222> LOCATION: (14)..(14)
<223> OTHER INFORMATION: n stands for 2',4'-bridged adenosine

<400> SEQUENCE: 46
nnnatgccct annn                                                              14

<210> SEQ ID NO 47
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged adenosine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (6)..(6)
<223> OTHER INFORMATION: n stands for 8-bromoguanosine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 47
nnnatnccct annn                                                              14

<210> SEQ ID NO 48
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine
```

<400> SEQUENCE: 48
nnntgcctcc gnnn                                                                                      14

<210> SEQ ID NO 49
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (5)..(5)
<223> OTHER INFORMATION: n stands for 8-bromoguanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 49
nnntncctcc gnnn                                                                                      14

<210> SEQ ID NO 50
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (3)..(3)
<223> OTHER INFORMATION: n stands for 2',4'-bridged guanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged thymidine

<400> SEQUENCE: 50
nnntgctttg gnnn    14

<210> SEQ ID NO 51
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (3)..(3)
<223> OTHER INFORMATION: n stands for 2',4'-bridged guanosine
<220> FEATURE:
<221> NAME/KEY: modified_base
<222> LOCATION: (10)..(10)
<223> OTHER INFORMATION: n stands for 8-bromoguanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged thymidine

<400> SEQUENCE: 51
nnntgctttn gnnn    14

<210> SEQ ID NO 52
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged m5c
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged m5c -continued

```
<400> SEQUENCE: 52
nnnccaagtt cnnn                                                    14

<210> SEQ ID NO 53
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged m5c
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (8)..(8)
<223> OTHER INFORMATION: n stands for 8-bromoguanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged m5c

<400> SEQUENCE: 53
nnnccaantt cnnn                                                    14

<210> SEQ ID NO 54
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged m5c
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (11)..(11)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c

<400> SEQUENCE: 54
nngtgatgac nnn                                                     13

<210> SEQ ID NO 55
```

```
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged m5c
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 8-bromoguanosine
<220> FEATURE:
<221> NAME/KEY: modified_base
<222> LOCATION: (11)..(11)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c

<400> SEQUENCE: 55
nnntgatgac nnn                                                        13

<210> SEQ ID NO 56
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged m5c
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (5)..(5)
<223> OTHER INFORMATION: n stands for 8-bromoguanosine
<220> FEATURE:
<221> NAME/KEY: modified_base
<222> LOCATION: (11)..(11)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c

<400> SEQUENCE: 56
nngtnatgac nnn                                                        13

<210> SEQ ID NO 57
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
```

```
<222> LOCATION: (1)..(1)
<223> OTHER INFORMATION: n stands for 2',4'-bridged m5c
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (8)..(8)
<223> OTHER INFORMATION: n stands for 8-bromoguanosine
<220> FEATURE:
<221> NAME/KEY: modified_base
<222> LOCATION: (11)..(11)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c

<400> SEQUENCE: 57
nngtgatnac nnn                                              13

<210> SEQ ID NO 58
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged m5c
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (11)..(11)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c

<400> SEQUENCE: 58
nnccctcgcc nnn                                              13

<210> SEQ ID NO 59
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged m5c
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (8)..(8)
<223> OTHER INFORMATION: n stands for 8-bromoguanosine
<220> FEATURE:
```

```
<221> NAME/KEY: modified_base
<222> LOCATION: (11)..(11)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c

<400> SEQUENCE: 59
nnccctcncc nnn                                                          13

<210> SEQ ID NO 60
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged m5c
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged m5c

<400> SEQUENCE: 60
nnnccaagtt cnnn                                                         14

<210> SEQ ID NO 61
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged m5c
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (8)..(8)
<223> OTHER INFORMATION: n stands for 7-phenylethynylguanosine
<220> FEATURE:
<221> NAME/KEY: modified_base
<222> LOCATION: (12)..(12)
<223> OTHER INFORMATION: n stands for 2',4'-bridged thymidine
```

```
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged m5c

<400> SEQUENCE: 61
nnnccaantt cnnn                                                            14

<210> SEQ ID NO 62
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged m5c
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (11)..(11)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c

<400> SEQUENCE: 62
nnccctcgcc nnn                                                             13

<210> SEQ ID NO 63
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged m5c
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (8)..(8)
<223> OTHER INFORMATION: n stands for 8-aminoguanosine
<220> FEATURE:
<221> NAME/KEY: modified_base
<222> LOCATION: (11)..(11)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
```

```
<400> SEQUENCE: 63
nnccctcncc nnn                                              13

<210> SEQ ID NO 64
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (3)..(3)
<223> OTHER INFORMATION: n stands for 2',4'-bridged guanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged thymidine

<400> SEQUENCE: 64
nnntgctttg gnnn                                             14

<210> SEQ ID NO 65
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (3)..(3)
<223> OTHER INFORMATION: n stands for 2',4'-bridged guanosine
<220> FEATURE:
<221> NAME/KEY: modified_base
<222> LOCATION: (5)..(5)
<223> OTHER INFORMATION: n stands for 8-aminoguanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged thymidine
```

<400> SEQUENCE: 65
nnntnctttg gnnn                                                                14

<210> SEQ ID NO 66
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (3)..(3)
<223> OTHER INFORMATION: n stands for 2',4'-bridged guanosine
<220> FEATURE:
<221> NAME/KEY: modified_base
<222> LOCATION: (10)..(10)
<223> OTHER INFORMATION: n stands for 8-aminoguanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged thymidine

<400> SEQUENCE: 66
nnntgctttn gnnn                                                                14

<210> SEQ ID NO 67
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged m5c
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged m5c

```
<400> SEQUENCE: 67
nnnccaagtt cnnn                                                    14

<210> SEQ ID NO 68
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged m5c
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (8)..(8)
<223> OTHER INFORMATION: n stands for 8-aminoguanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged m5c

<400> SEQUENCE: 68
nnnccaantt cnnn                                                    14

<210> SEQ ID NO 69
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged m5c
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (11)..(11)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c

<400> SEQUENCE: 69
nngtgatgac nnn                                                     13

<210> SEQ ID NO 70
```

```
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged m5c
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 8-aminoguanosine
<220> FEATURE:
<221> NAME/KEY: modified_base
<222> LOCATION: (11)..(11)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c

<400> SEQUENCE: 70
nnntgatgac nnn                                              13

<210> SEQ ID NO 71
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged m5c
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged adenosine
<220> FEATURE:
<221> NAME/KEY: modified_base
<222> LOCATION: (14)..(14)
<223> OTHER INFORMATION: n stands for 2',4'-bridged adenosine

<400> SEQUENCE: 71
nnncgcatgc cnnn                                             14

<210> SEQ ID NO 72
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
```

```
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged m5c
<220> FEATURE:
<221> NAME/KEY: modified_base
<222> LOCATION: (9)..(9)
<223> OTHER INFORMATION: n stands for 7-phenylethynylguanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged adenosine
<220> FEATURE:
<221> NAME/KEY: modified_base
<222> LOCATION: (14)..(14)
<223> OTHER INFORMATION: n stands for 2',4'-bridged adenosine

<400> SEQUENCE: 72
nnncgcatnc cnnn                                                     14

<210> SEQ ID NO 73
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged m5c
<220> FEATURE:
<221> NAME/KEY: modified_base
<222> LOCATION: (9)..(9)
<223> OTHER INFORMATION: n stands for 7-(4-pyridyl)ethynylguanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged adenosine
<220> FEATURE:
<221> NAME/KEY: modified_base
<222> LOCATION: (14)..(14)
<223> OTHER INFORMATION: n stands for 2',4'-bridged adenosine

<400> SEQUENCE: 73
nnncgcatnc cnnn                                                     14

<210> SEQ ID NO 74
<211> LENGTH: 14
<212> TYPE: DNA
<213> ORGANISM: Artificial Sequence
<220> FEATURE:
<223> OTHER INFORMATION: Synthetic Sequence
<220> FEATURE:
```

-continued

```
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged m5c
<220> FEATURE:
<221> NAME/KEY: modified_base
<222> LOCATION: (9)..(9)
<223> OTHER INFORMATION: n stands for 7-hydroxymethylethynylguanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged adenosine
<220> FEATURE:
<221> NAME/KEY: modified_base
<222> LOCATION: (14)..(14)
<223> OTHER INFORMATION: n stands for 2',4'-bridged adenosine

<400> SEQUENCE: 74
nnncgcatnc cnnn                                                        14

<210> SEQ ID NO 75
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged m5c
<220> FEATURE:
<221> NAME/KEY: modified_base
<222> LOCATION: (9)..(9)
<223> OTHER INFORMATION: n stands for 7-iodoguanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged adenosine
<220> FEATURE:
<221> NAME/KEY: modified_base
<222> LOCATION: (14)..(14)
<223> OTHER INFORMATION: n stands for 2',4'-bridged adenosine

<400> SEQUENCE: 75
nnncgcatnc cnnn                                                        14

<210> SEQ ID NO 76
<211> LENGTH: 14
<212> TYPE: DNA
<213> ORGANISM: Artificial Sequence
<220> FEATURE:
<223> OTHER INFORMATION: Synthetic Sequence
```

```
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (3)..(3)
<223> OTHER INFORMATION: n stands for 2',4'-bridged guanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged thymidine

<400> SEQUENCE: 76
nnntgctttg gnnn                                                        14

<210> SEQ ID NO 77
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (3)..(3)
<223> OTHER INFORMATION: n stands for 2',4'-bridged guanosine
<220> FEATURE:
<221> NAME/KEY: modified_base
<222> LOCATION: (5)..(5)
<223> OTHER INFORMATION: n stands for 7-(4-pyridyl)ethynylguanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged thymidine

<400> SEQUENCE: 77
nnntnctttg gnnn                                                        14

<210> SEQ ID NO 78
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
```

```
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (3)..(3)
<223> OTHER INFORMATION: n stands for 2',4'-bridged guanosine
<220> FEATURE:
<221> NAME/KEY: modified_base
<222> LOCATION: (5)..(5)
<223> OTHER INFORMATION: n stands for 7-iodoguanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged thymidine

<400> SEQUENCE: 78
nnntnctttg gnnn                                                           14

<210> SEQ ID NO 79
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged guanosine
<220> FEATURE:
<221> NAME/KEY: modified_base
<222> LOCATION: (3)..(3)
<223> OTHER INFORMATION: n stands for 2',4'-bridged guanosine
<220> FEATURE:
<221> NAME/KEY: modified_base
<222> LOCATION: (10)..(10)
<223> OTHER INFORMATION: n stands for 7-iodoguanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged thymidine

<400> SEQUENCE: 79
nnntgctttn gnnn                                                           14

<210> SEQ ID NO 80
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
```

```
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged m5c
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged m5c

<400> SEQUENCE: 80
nnnccaagtt cnnn                                                      14

<210> SEQ ID NO 81
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
<221> NAME/KEY: modified_base
<222> LOCATION: (2)..(2)
<223> OTHER INFORMATION: n stands for 2',4'-bridged m5c
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (8)..(8)
<223> OTHER INFORMATION: n stands for 7-(4-pyridyl)ethynylguanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged m5c

<400> SEQUENCE: 81
nnnccaantt cnnn                                                      14

<210> SEQ ID NO 82
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged adenosine
<220> FEATURE:
```

```
<221> NAME/KEY: modified_base
<222> LOCATION: (2)..(2)
<223> OTHER INFORMATION: n stands for 2',4'-bridged m5c
<220> FEATURE:
<221> NAME/KEY: modified_base
<222> LOCATION: (3)..(3)
<223> OTHER INFORMATION: n stands for 2',4'-bridged adenosine
<220> FEATURE:
<221> NAME/KEY: modified_base
<222> LOCATION: (8)..(8)
<223> OTHER INFORMATION: n stands for 7-iodoguanosine
<220> FEATURE:
<221> NAME/KEY: modified_base
<222> LOCATION: (12)..(12)
<223> OTHER INFORMATION: n stands for 2',4'-bridged thymidine
<220> FEATURE:
<221> NAME/KEY: modified_base
<222> LOCATION: (13)..(13)
<223> OTHER INFORMATION: n stands for 2',4'-bridged m5c
<220> FEATURE:
<221> NAME/KEY: modified_base
<222> LOCATION: (14)..(14)
<223> OTHER INFORMATION: n stands for 2',4'-bridged m5c

<400> SEQUENCE: 82
nnnccaantt cnnn                                                  14

<210> SEQ ID NO 83
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 83
nnnatgccac cnnn                                                  14

<210> SEQ ID NO 84
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
```

```
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (7)..(7)
<223> OTHER INFORMATION: n stands for 5-hydroxycytidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 84
nnnatgncac cnnn                                                       14

<210> SEQ ID NO 85
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (8)..(8)
<223> OTHER INFORMATION: n stands for 5-hydroxycytidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 85
nnnatgcnac cnnn                                                       14

<210> SEQ ID NO 86
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
```

```
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (10)..(10)
<223> OTHER INFORMATION: n stands for 5-hydroxycytidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 86
nnnatgccan cnnn                                                         14

<210> SEQ ID NO 87
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (11)..(11)
<223> OTHER INFORMATION: n stands for 5-hydroxycytidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 87
nnnatgccac nnnn                                                         14

<210> SEQ ID NO 88
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
```

```
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 88
nnnatgccac cnnn                                                        14

<210> SEQ ID NO 89
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (7)..(7)
<223> OTHER INFORMATION: n stands for 5-hydroxycytidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 89
nnnatgncac cnnn                                                        14

<210> SEQ ID NO 90
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
```

```
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (5)..(5)
<223> OTHER INFORMATION: n stands for 2-thiocarbonylthymidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 90
nnnangccac cnnn                                                           14

<210> SEQ ID NO 91
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (6)..(6)
<223> OTHER INFORMATION: n stands for 8-bromoguanosine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 91
nnnatnccac cnnn                                                           14

<210> SEQ ID NO 92
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
```

```
-continued

<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (5)..(5)
<223> OTHER INFORMATION: n stands for 2-thiocarbonylthymidine
<220> FEATURE:
<221> NAME/KEY: modified_base
<222> LOCATION: (7)..(7)
<223> OTHER INFORMATION: n stands for 5-hydroxycytidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 92
nnnangncac cnnn                                                      14

<210> SEQ ID NO 93
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (5)..(5)
<223> OTHER INFORMATION: n stands for 2-thiocarbonylthymidine
<220> FEATURE:
<221> NAME/KEY: modified_base
<222> LOCATION: (6)..(6)
<223> OTHER INFORMATION: n stands for 8-bromoguanosine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 93
nnnannccac cnnn                                                      14

<210> SEQ ID NO 94
<211> LENGTH: 14
<212> TYPE: DNA
<213> ORGANISM: Artificial Sequence
<220> FEATURE:
```

```
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (6)..(6)
<223> OTHER INFORMATION: n stands for 8-bromoguanosine
<220> FEATURE:
<221> NAME/KEY: modified_base
<222> LOCATION: (7)..(7)
<223> OTHER INFORMATION: n stands for 5-hydroxycytidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
<222> LOCATION: (14)..(14)
<223> OTHER INFORMATION: n stands for 2',4'-bridged adenosine

<400> SEQUENCE: 94
nnnatnncac cnnn                                                         14

<210> SEQ ID NO 95
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n stands for 2',4'-bridged guanosine
<220> FEATURE:
<221> NAME/KEY: modified_base
<222> LOCATION: (2)..(2)
<223> OTHER INFORMATION: n stands for 2',4'-bridged thymidine
<220> FEATURE:
<221> NAME/KEY: modified_base
<222> LOCATION: (3)..(3)
<223> OTHER INFORMATION: n stands for 2',4'-bridged thymidine
<220> FEATURE:
<221> NAME/KEY: modified_base
<222> LOCATION: (5)..(5)
<223> OTHER INFORMATION: n stands for 2-thiocarbonylthymidine
<220> FEATURE:
<221> NAME/KEY: modified_base
<222> LOCATION: (6)..(6)
<223> OTHER INFORMATION: n stands for 8-bromoguanosine
<220> FEATURE:
<221> NAME/KEY: modified_base
<222> LOCATION: (7)..(7)
<223> OTHER INFORMATION: n stands for 5-hydroxycytidine
<220> FEATURE:
<221> NAME/KEY: modified_base
<222> LOCATION: (12)..(12)
<223> OTHER INFORMATION: n stands for 2',4'-bridged m5c
<220> FEATURE:
<221> NAME/KEY: modified_base
<222> LOCATION: (13)..(13)
<223> OTHER INFORMATION: n stands for 2',4'-bridged thymidine
<220> FEATURE:
<221> NAME/KEY: modified_base
```

```
<222> LOCATION: (14)..(14)
<223> OTHER INFORMATION: n stands for 2',4'-bridged adenosine

<400> SEQUENCE: 95
nnnannncac cnnn                                               14
```

ANTISENSE OLIGONUCLEIC ACID

CROSS-REFERENCE TO RELATED APPLICATIONS

This patent application is a divisional of co-pending U.S. patent application Ser. No. 16/487,762, filed on Aug. 21, 2019, which is the U.S. national phase of International Patent Application No. PCT/JP2018/006061, filed Feb. 20, 2018, which claims the benefit of Japanese Patent Application No. 2017-030489, filed Feb. 21, 2017, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 75,307 bytes ASCII (Text) file named "758737Sequence-Listing.txt," created Feb. 3, 2022.

TECHNICAL FIELD

The present invention relates to an antisense oligonucleic acid with low hepatotoxicity.

BACKGROUND ART

Nucleic acid medicines can suppress expression of specific genes in cells unlike conventional pharmaceutical products. They are expected to lead to the creation of innovative pharmaceutical products for diseases that were previously difficult to treat. As a technique relating to nucleic acid medicine, for example, an antisense method has been developed in which an antisense oligonucleic acid complementary to a part of mRNA involved in the disease is introduced from the outside to cause formation of a double strand, which in turn inhibits translation process of the pathogenic mRNA and treats or prevents the disease.

However, antisense oligonucleic acid has a defect in that it is easily degraded by nucleases in vivo. In addition, the binding affinity and specificity for target mRNA need to be improved further. Thus, the study group of the present inventors developed a nucleic acid molecule bridged at the 2'- and 4'-positions in an attempt to improve nuclease resistance and binding affinity and specificity to target mRNA by stabilization of the steric structure (patent documents 1-5) and, using such bridged nucleic acid, developed an oligonucleotide useful as a therapeutic agent for dyslipidemia which is superior in binding affinity to PCSK9 gene and the like (patent document 6).

However, as nucleic acid medicament discovery research in anticipation of human clinical trials progresses, new issues to be solved have become apparent. The most important one is "avoidance of potential toxicity of artificial oligonucleotides".

For example, it is known that antisense oligonucleic acid intravenously administered to rats and mice is delivered to the liver in about 12 hours. Some antisense oligonucleic acids exhibit severe hepatotoxicity. While the mechanism is not necessarily clear, suppression of expression of non-target mRNA, activation of natural immunity, promotion of expression of unidentified protein gene and the like are considered. As a means to predict hepatotoxicity of antisense oligonucleic acids, research is being conducted to identify the base sequence common to antisense oligonucleic acids exhibiting hepatotoxicity (non-patent documents 1, 2).

DOCUMENT LIST

Patent Documents patent document 1: WO 2011/052436
patent document 2: WO 2014/046212
patent document 3: WO 2014/112463
patent document 4: WO 2015/125783
patent document 5: WO 2016/017422
patent document 6: WO 2013/118776

Non-Patent Document non-patent document 1: Peter H. Hagedorn et al., Nucleic Acid Therapeutics, 23(5), pp. 302-310 (2013)
non-patent document 2: Andrew D. Burdick et al., Nucleic Acids Research, 2014, pp. 1-10

SUMMARY OF THE INVENTION

Problems to be Solved by the Invention

As mentioned above, studies are being conducted to identify the base sequence considered to be involved in the hepatotoxicity of antisense oligonucleic acids. The base sequences considered to be involved in hepatotoxicity in the above-mentioned non-patent documents 1, 2 are only nt2 and nt3, and it is sometimes difficult to design an antisense oligonucleic acid free of such short base sequences. For example, mRNA has a partial self structure for stabilization such as a loop structure, a double strand and the like, and there is a limitation that antisense oligonucleic acid should be designed to hybridize to a single strand of the target mRNA. Moreover, a base sequence that hybridizes to a single strand of the target mRNA and is free of the above-mentioned base sequence does not necessarily show an excellent activity without hepatotoxicity.

Therefore, the present invention aims to provide an antisense oligonucleic acid with reduced hepatotoxicity.

Means of Solving the Problems

The present inventors have conducted intensive studies in an attempt to solve the aforementioned problems. As a result, they have found that particularly, hepatotoxicity of an antisense oligonucleic acid can be reduced while maintaining its activity by modifying a base of a nucleic acid residue in a particular region of the antisense oligonucleic acid, which resulted in the completion of the present invention.

The present invention is shown below.

[1] An antisense oligonucleic acid having a base length of not less than 7 nt and not more than 30 nt, wherein
nucleic acid residues of not less than 1 nt and not more than 5 nt respectively from the both terminals are 2',4'-bridged nucleic acids,
2',4'-non-bridged nucleic acid residue(s) is(are) present between the above-mentioned both terminals, and
one or more bases in the nucleic acid residue(s) of the above-mentioned 2',4'-non-bridged nucleic acid residue(s) is/are modified.

[2] The antisense oligonucleic acid of the above-mentioned [1] wherein the above-mentioned 2',4'-nonbridged nucleic acid residue with the modified base is contained in a sequence of TGC or TCC.

[3] The antisense oligonucleic acid of the above-mentioned [1] wherein the above-mentioned modified base is 5-hydroxycytosine, 4-acetylcytosine, 3-$C_{1-6}$ alkylcytosine, 5-$C_{1-6}$ alkylcytosine, 2-thiocytosine, 2-thiothymine, dihydrothymine, pseudo thymine, 2-thiouridine, 5-(carboxyhydroxymethyl)uridine, 5-carboxymethylaminomethyl-2-thiouridine, 5-carboxymethylaminomethyluridine, dihydrouridine, pseudo uridine, 5-methylaminomethyluridine, 5-methylaminomethyl-2-thiouridine, 5-methoxycarbonylmethyl-2-thiouridine, 5-methoxycarbonylmethyluridine, 5-methoxyuridine, 8-aminoguanine, 8-halogenoguanine, 7-deaza-7-(2-phenylethynyl)guanine, 7-deaza-7-(2-pyridylethynyl)guanine, 7-deaza-7-[2-($C_{1-7}$ alkanoyloxy-$C_{1-6}$alkyl)ethynyl]guanine, 7-deaza-7-[2-(hydroxy-$C_{1-6}$alkyl)ethynyl]guanine, 1-$C_{1-6}$alkylguanine, 2,2-di($C_{1-6}$alkyl)guanine, 2-$C_{1-6}$ alkylguanine, 7-deaza-7-$C_{1-6}$ alkylguanine, 7-deaza-7-$C_{2-6}$ alkenylguanine, 7-deaza-7-$C_{2-6}$ alkynylguanine, 7-deaza-7-halogenoguanine, inosine, 1-$C_{1-6}$alkylinosine, queuosine, β,D-galactosylqueuosine, β,D-mannosylqueuosine, $N^6$—$C_{2-6}$ alkenyladenine, 1-$C_{1-6}$ alkyladenine, 2-$C_{1-6}$ alkyladenine, $N^6$—$C_{1-6}$ alkyladenine or 2-$C_{1-6}$ alkylthio-$N^6$—$C_{2-6}$ alkenyladenine.

[4] The antisense oligonucleic acid of any of the above-mentioned [1] to [3] wherein the above-mentioned 2',4'-non-bridged nucleic acid residue is DNA.

[5] The antisense oligonucleic acid of any of the above-mentioned [1] to [4] wherein the above-mentioned 2',4'-bridged nucleic acid residue has a structure of any of the following formulas (I) to (III)

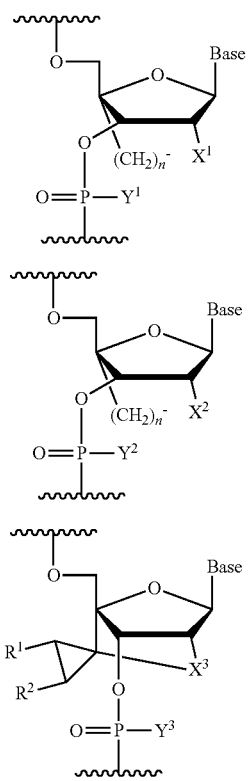

wherein
$X^1$ is O, S, a >N($R^3$) group, a —C(=O)—O— group or a —C(=O)—N($R^4$)— group ($R^3$ and $R^4$ are each independently H or a $C_{1-6}$ alkyl group),
$X^2$ is a guanidino group represented by any of the following formulas (IV) to (VII):

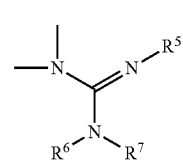

(IV)

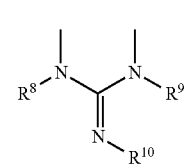

(V)

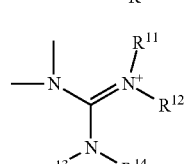

(VI)

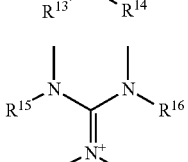

(VII)

wherein $R^5$-$R^{18}$ are each independently H, a $C_{1-6}$ alkyl group, a $C_{3-10}$ cycloalkyl group, an amino-protecting group or a 2-cyanoethyloxycarbonyl group,
$X^3$ is O, S, a >N($R^{19}$) group, a —C(=O)—O— group or a —C(=O)—N($R^{20}$)— group ($R^{19}$ and $R^{20}$ are each independently H or a $C_{1-6}$ alkyl group),
$Y^1$-$Y^3$ are each independently O— or S—,
Base is a nucleic acid base group,
$R^1$ and $R^2$ are each independently H, a $C_{1-6}$ alkyl group or $R^1$ and $R^2$ may be taken together to form a $C_{1-4}$ alkylene group, and
n is an integer of not less than 0 and not more than 2.

[6] The antisense oligonucleic acid of the above-mentioned [5] wherein the above-mentioned 2',4'-bridged nucleic acid residue has a structure of the above-mentioned formula (I), $X^1$ is O and n is 1.

[7] The antisense oligonucleic acid of any of the above-mentioned [1] to [6] showing reduced hepatotoxicity compared to that before introduction of the above-mentioned modification into the base of the nucleic acid residue.

In this disclosure, the "$C_{1-6}$ alkyl group" is a linear or branched chain monovalent saturated aliphatic hydrocarbon group with a carbon number of not less than one and not more than 6. For example, methyl, ethyl, n-propyl, isopropyl, n-butyl, isobutyl, s-butyl, t-butyl, n-pentyl, n-hexyl and the like can be mentioned. Preferred is a $C_{1-4}$ alkyl group, more preferred is a $C_{1-2}$ alkyl group, most preferred is methyl.

The "$C_{2-6}$ alkenyl group" is a linear or branched chain monovalent unsaturated aliphatic hydrocarbon group with a carbon number of not less than 2 and not more than 6 and having at least one carbon-carbon double bond. Examples include ethenyl(vinyl), 1-propenyl, 2-propenyl(allyl), isopropenyl, 2-butenyl, 3-butenyl, isobutenyl, pentenyl, isopentenyl, hexenyl and the like.

The "$C_{2-6}$ alkynyl group" is a linear or branched chain monovalent unsaturated aliphatic hydrocarbon group with a carbon number of not less than 2 and not more than 6 and having at least one carbon-carbon triple bond. Examples include ethynyl, 1-propynyl, 2-propynyl(propargyl), 2-butynyl, 3-butynyl, pentynyl, hexynyl and the like. Preferred is a $C_{2-4}$ alkynyl group, more preferred is a $C_{2-3}$ alkynyl group.

The "$C_{6-12}$ aryl group" is a monovalent aromatic hydrocarbon group with a carbon number of not less than 6 and not more than 12. Examples include phenyl, naphthyl, indenyl, biphenyl and the like.

Examples of the "halogeno group" include fluoro group, chloro group, bromo group and iodo group, with preference given to chloro group and bromo group.

The "$C_{3-10}$ cycloalkyl group" is a cyclic monovalent saturated aliphatic hydrocarbon group with a carbon number of not less than 3 and not more than 10. It is, for example, cyclopropyl, methylcyclopropyl, dimethylcyclopropyl, cyclobutyl, cyclopentyl, cyclohexyl, adamantyl or the like. Preferred is a $C_{3-6}$ cycloalkyl group.

Examples of the "amino-protecting group" include alkoxycarbonyl protecting groups such as t-butoxycarbonyl group, methoxycarbonyl group, ethoxycarbonyl group and the like; arylmethoxycarbonyl protecting groups such as benzyloxycarbonyl group, p-methoxybenzyloxycarbonyl group, p-nitrobenzyloxycarbonyl group, o-nitrobenzyloxycarbonyl group and the like; arylmethyl protecting groups such as benzyl group, 4-methoxybenzyl group, triphenylmethyl group and the like; alkanoyl protecting groups such as formyl group, acetyl group and the like; aroyl protecting groups such as benzoyl group and the like; arylsulfonyl protecting groups such as 2,4-di nitrobenzenesulfonyl group, o-nitrobenzenesulfonyl group and the like, and the like.

The "$C_{1-6}$ alkylene group" is a linear or branched chain divalent saturated aliphatic hydrocarbon group with a carbon number of not less than 1 and not more than 6. It is, for example, methylene, ethylene, methylmethylene, n-propylene, methylethylene, n-butylene, methylpropylene, dimethylethylene, n-pentylene, n-hexylene or the like. It is preferably a $C_{1-4}$ alkylene group, more preferably a $C_{1-2}$ alkylene group, further more preferably methylene.

The "$C_{1-7}$ alkanoyl group" is an atomic group of aliphatic carboxylic acid with a carbon number of 1 to 7 less OH. It is, for example, formyl, acetyl, ethylcarbonyl, n-propylcarbonyl, isopropylcarbonyl, n-butylcarbonyl, isobutylcarbonyl, t-butylcarbonyl, n-pentylcarbonyl, n-hexylcarbonyl or the like, preferably a $C_{1-4}$ alkanoyl group, more preferably acetyl.

Effect of the Invention

The hepatotoxicity of the antisense oligonucleic acid of the present invention is remarkably reduced. Furthermore, the antisense oligonucleic acid of the present invention has high binding affinity to target mRNA, is resistant to nuclease attack in vivo and is stable. Therefore, the antisense oligonucleic acid of the present invention is industrially extremely useful since it may be a highly practical nucleic acid medicament.

DESCRIPTION OF EMBODIMENTS

Figure 1:
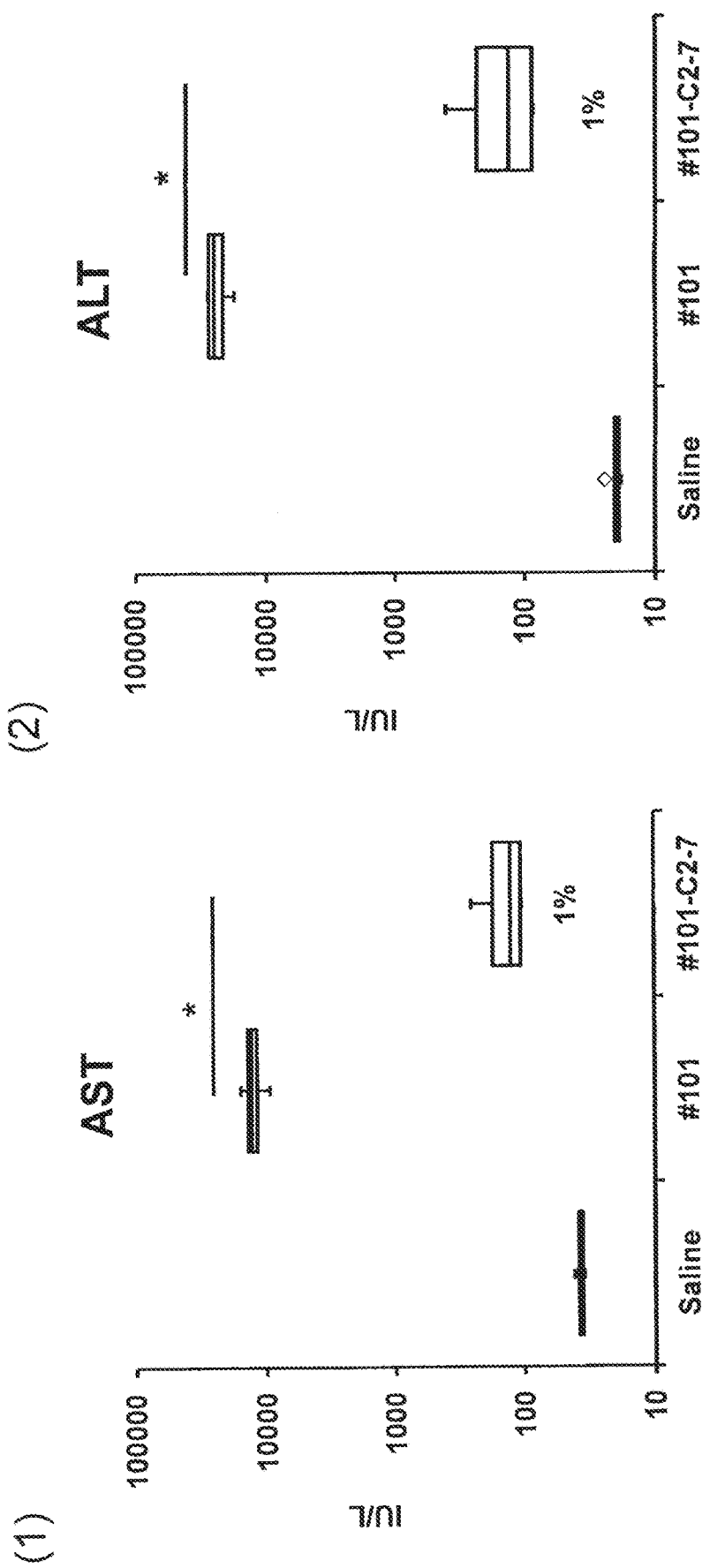
FIG. 1 is a graph showing the results of hepatotoxicity of antisense oligonucleic acid evaluated in the Example described later.

The antisense oligonucleic acid of the present invention is characterized in that it has a base length of not less than 7 nt, not more than 30 nt; nucleic acid residues of not less than 1 nt and not more than 5 nt respectively from the both terminals are 2',4'-bridged nucleic acids; 2',4'-non-bridged nucleic acid residue(s) is(are) present between the above-mentioned both terminals; and one or more bases in the nucleic acid residue(s) of the above-mentioned 2',4'-non-bridged nucleic acid residue(s) is/are modified.

The base sequence of the antisense oligonucleic acid of the present invention is not particularly limited as long as it can hybridize to the target mRNA with high binding affinity and one or more bases of nucleic acid residue in a particular region is/are modified. The original base sequence before modification of the base can be determined by a conventional method according to the target mRNA.

For example, when the translation initiation site of target mRNA is selected as a binding target site, an antisense oligonucleic acid with high translation inhibitory activity may be designed. mRNA sometimes forms a hairpin loop structure or a double strand structure in the molecule, and a single strand structure site is kinetically and thermodynamically preferable as a binding target site. Thus, the secondary structure of mRNA is predicted by calculation, and a site predicted to be a single-stranded structure can be selected as a binding target site. It is also possible to identify a sequence most likely to form a double strand with the target mRNA by random screening using RNaseH, which selectively cleaves the site where the double strand is formed.

The nucleic acid base in the antisense oligonucleic acid of the present invention may be, besides a modified base, general adenine, guanine, uracil, thymine or cytosine. Since methylcytosine can be easily synthesized from thymine, methylcytosine may also be used instead of cytosine.

The antisense oligonucleic acid of the present invention may also be a thioated oligonucleic acid. In general oligonucleic acids, riboses are linked by a phosphodiester bond. The resistance of oligonucleic acid to exonuclease and endonuclease is improved by binding riboses with a phosphorothioate bond. The oligonucleic acid may be complete thioated oligonucleic acid in which all phosphoric acid groups are thioated or chimeric thioated oligonucleic acid in which a part of the phosphoric acid group is thioated.

The base length of the antisense oligonucleic acid of the present invention is preferably not less than 7 nt and not more than 30 nt. When the base length is not less than 7 nt, the binding affinity and specificity to the target mRNA can be sufficiently ensured. On the other hand, when the base length is not more than 30 nt, the antigenicity is sufficiently suppressed and synthesis is facilitated. The base length is preferably not less than 10 nt, more preferably not less than 12 nt, and preferably not more than 25 nt and preferably not more than 20 nt. The number of oligonucleic acids with a base length of 17 nt is $4^{17}=1.7\times10^{10}$ and exceeds $2\times3\times10^9$ which is the total number of bases in the human genome. Accordingly, it is also possible to set the base length to not less than 17 nt to improve specificity.

In the antisense oligonucleic acid of the present invention, nucleic acid residues each independently not less than 1 nt and not more than 5 nt from the both terminals are 2',4'-bridged nucleic acids. The nucleic acids at at least both terminal sites are 2',4'-bridged, which renders attacks by various nucleases difficult in vivo, and the antisense oligonucleic acid can be present in the living body for a long time after administration to the living body. In addition, since the structure is stabilized by 2',4'-bridging, a double strand is easily formed with the target mRNA.

The 2',4'-bridged structures in two or more 2',4'-bridged nucleic acid residues may be identical to or different from one another. The 2',4'-bridged structure is not particularly limited as long as it stabilizes the structure of the ribose moiety and, for example, the structures of the above-mentioned formulas (I) to (III) can be mentioned.

The nucleic acid base in the 2',4'-bridged nucleic acid residue may be a general adenine, guanine, uracil, thymine or cytosine and may be modified. Since methylcytosine can be easily synthesized from thymine, methylcytosine may also be used instead of cytosine, particularly at the both terminal sites. The number of modified bases at the both terminal sites varies depending on the 2',4'-bridged nucleic acid residues at the both terminal sites and is preferably not more than 5 or not more than 4, more preferably not more than 3, further more preferably 1 or 2. The modified bases in the both terminal sites may be, for example, those similar to the modified base in the 2',4'-non-bridged nucleic acid residue.

The antisense oligonucleic acid according to the present invention has one or more 2',4'-non-bridged nucleic acid residues between both terminals composed of 2',4'-bridged nucleic acid residues. That is, the antisense oligonucleic acid according to the present invention is composed of 2',4'-non-bridged nucleic acid residues except for the both terminal sites thereof. Hereinafter, in the present disclosure, the parts other than the above-mentioned both terminal sites of the antisense oligonucleic acid according to the present invention are sometimes referred to as a "middle part". The 2',4'-non-bridged nucleic acid residue in the middle part may be RNA, DNA, a nucleic acid derivative, or a combination of two or more of these as long as bridging is absent between the 2' position and the 4' position. Examples of the nucleic acid derivative include 2'-$C_{1-6}$ alkylcarbonyloxynucleic acids such as 2'-halogenonucleic acid, 2'-acetoxynucleic acid and the like, 2'-$C_{1-6}$ alkyloxynucleic acids such as 2'-methoxynucleic acid and the like, 2'-tri$C_{1-6}$ alkylsilyloxynucleic acids such as 2'-trimethylsilyloxynucleic acid and the like, and the like. It is preferable that all the nucleic acids in the above-mentioned middle part be DNAs. When all the nucleic acids in the middle part are DNAs, an RNA-DNA double strand is formed to the target mRNA, the double strand becomes a substrate for RNAseH, and the target mRNA is cleaved. From the aspect of the substrate of RNAseH, the length of the above-mentioned middle part is preferably not less than 4, more preferably not less than 5, and still more preferably not less than 6. On the other hand, the length of the above-mentioned middle part is preferably not more than 10 nt from the aspect of antigenicity.

In the antisense oligonucleic acid according to the present invention, the bases of one or more nucleic acid residues in the above-mentioned middle part are modified. Since the original base sequence of the antisense oligonucleic acid of the present invention is complementary to the base sequence of the binding target site of the target mRNA, and has strong binding affinity to the binding target site, the binding affinity is considered to be maintained even if the base of the middle part that forms a double strand with the target mRNA is modified. On the other hand, the hepatotoxicity of the antisense oligonucleic acid is caused by the interaction with compounds other than the target mRNA and the binding affinity to such compounds is highly likely lower than that to the target mRNA. In the present invention, the interaction with such compounds is considered to be reduced to the extent that hepatotoxicity is reduced, by modifying the base of one or more nucleic acid residues in the above-mentioned middle part.

The number of nucleic acid residues whose bases are modified in the middle part is preferably not more than 5, depending on the number of nucleic acid residues constituting the middle part. It is considered that the lower the number, the more certainly the binding affinity to the target mRNA is maintained. The number is preferably not more than 4 or not more than 3, further more preferably 2 or 1 and particularly preferably 1.

As modification of the base, for example, substitution of a group, addition of a functional group, removal of a functional group are considered. For modification of a base, two or more modifications may be combined as long as it is within one base. The substitution of a group may be not only substitution of a substituent bound to heterocycle of the base, but also substitution of a group forming the heterocycle of the base. For example, it is also possible to substitute =N— forming heterocycle of the base with =C<. For example, =N— at the 7-position of adenine and guanine may become =N$^+$< by the addition of a functional group.

When cytosine is to be modified, a preferable substituent introduction position is, for example, the 5-position. As the substituent at the 5-position, $C_{1-6}$ alkyl group, $C_{2-6}$ alkenyl group, $C_{2-6}$ alkynyl group, $C_{6-12}$ aryl group, hydroxyl group, amino group, $C_{1-6}$ alkylamino group, di($C_{1-6}$ alkyl)amino group, a carboxy group, sulfonic acid group and the like can be mentioned. In addition, one or two from $C_{1-6}$ alkyl group, $C_{2-6}$ alkenyl group and $C_{2-6}$ alkynyl group may be introduced into the 4-position amino group.

Preferable modification of cytosine, thymine and uracil includes, for example, substitution of the 2-position carbonyl group with a thiocarbonyl group. In addition, a $C_{1-6}$ alkyl group may be introduced into the 3-position amino group of thymine or uracil.

When guanine or adenine is to be modified, a preferable substituent introduction position is, for example, the 8-position. Examples of the substituent at the 8-position include halogeno groups in addition to hydrophilic substituents such as amino group, $C_{1-6}$ alkylamino group, di($C_{1-6}$ alkyl)amino group and the like. Alternatively, the 7-position =N— may be converted to =C< and a phenylethynyl group may be introduced.

Examples of more specific modified base include cytosine derivatives such as 5-hydroxycytosine, 4-acetylcytosine, 3-$C_{1-6}$ alkylcytosine, 5-$C_{1-6}$ alkylcytosine, 2-thiocytosine and the like; thymine derivatives such as 2-thiothymine, dihydrothymine, pseudo thymine and the like; uridine derivatives such as 2-thiouridine, 5-(carboxyhydroxymethyl)uridine, 5-carboxymethylaminomethyl-2-thiouridine, 5-carboxymethylaminomethyluridine, dihydrouridine, pseudo uridine, 5-methylaminomethyluridine, 5-methylaminomethyl-2-thiouridine, 5-methoxycarbonylmethyl-2-thiouridine, 5-methoxycarbonylmethyluridine, 5-methoxyuridine and the like; guanine derivatives such as 8-aminoguanine, 8-halogenoguanine, 7-deaza-7-(2-phenylethynyl)guanine, 7-deaza-7-[2-(4-pyridyl)ethynyl]guanine, 7-deaza-7-[2-(2-pyridyl)ethynyl]guanine, 7-deaza-7-[2-(3-pyridyl)ethynyl]guanine, 7-deaza-7-[2-($C_{1-7}$ alkanoyloxy-$C_{1-6}$ alkyl)ethynyl]guanine, 7-deaza-7-[2-(hydroxy-$C_{1-6}$ alkyl)ethynyl]guanine, 1-$C_{1-6}$ alkylguanine, 2,2-di($C_{1-6}$ alkyl) guanine, 2-$C_{1-6}$ alkylguanine, 7-deaza-7-$C_{1-6}$ alkylguanine, 7-deaza-7-$C_{2-6}$ alkenylguanine, 7-deaza-7-$C_{2-6}$ alkynylguanine, 7-deaza-7-halogenoguanine, inosine, 1-$C_{1-6}$ alkylinosine, queuosine, β,D-galactosylqueuosine, β,D-mannosylqueuosine and the like; and adenine derivatives such as $N^6$—$C_{2-6}$ alkenyladenine, 1-$C_{1-6}$ alkyladenine, 2-$C_{1-6}$ alkyladenine, $N^6$—$C_{1-6}$ alkyladenine, 2-$C_{1-6}$ alkylthio-$N^6$—$C_{2-6}$ alkenyladenine and the like.

The present inventors developed the following novel 7-substituted guanosine derivative (VIII) as a compound having a modified base:

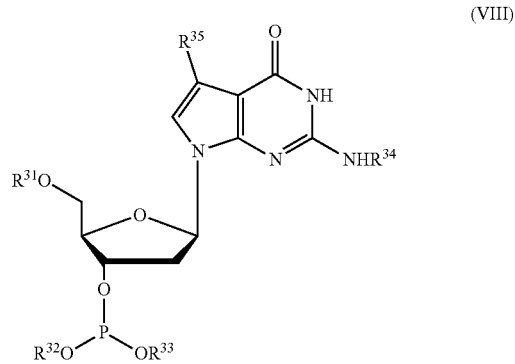

(VIII)

wherein
$R^{31}$ is H or a hydroxyl-protecting group selected from a silyl protecting group, a trityl protecting group, a carbamate protecting group and a benzylether protecting group;

$R^{32}$ and $R^{33}$ are each independently a phenyl group optionally substituted by a halogeno group, a nitro group or a $C_{1-6}$ alkyl group, or a $C_{1-6}$ alkyl group optionally substituted by a cyano group;

$R^{34}$ is an amino-protecting group; and $R^{35}$ is a halogeno group or $R^{36}$—C≡C— ($R^{36}$ is a $C_{6-12}$ aryl group, a heterocyclic aromatic ring group, a hydroxy-$C_{1-6}$ alkyl group or a $C_{1-7}$ alkanoyloxy-$C_{1-6}$ alkyl group).

Examples of the "silyl protecting group" include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxyphenylsilyl and the like, examples of the "trityl protecting group" include triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4''-tris(4,5-dichlorophthalimidophenyl)methyl, 4,4',4''-tris(levulinoyl oxyphenyl)methyl, 4,4',4''-tris(benzoyloxyphenyl)methyl, 3-(imidazoyl-1-ylmethyl)bis(4',4''-dimethoxyphenyl)methyl, 1,1-bis(4-methoxyphenyl)-1'-pyrenylmethyl and the like, examples of the "carbamate protecting group" include t-butoxycarbonyl, fluorenylmethyloxycarbonyl, benzyloxycarbonyl and the like, examples of the "benzylether protecting group" include benzyl, methoxybenzyl, nitrobenzyl, halobenzyl, phenylbenzyl and the like, and examples of the "alkanoyl protecting group" include formyl, acetyl, halogenated acetyl, pivaloyl, benzoyl and the like. As the "amino-protecting group", those recited above can be mentioned.

The "heterocyclic aromatic ring group" refers to a 5-membered ring aromatic heterocyclyl group, 6-membered ring aromatic heterocyclyl group or fused ring aromatic heterocyclyl group having at least one hetero atom such as a nitrogen atom, an oxygen atom, a sulfur atom and the like. For example, 5-membered heterocyclic aromatic ring groups such as pyrrolyl, imidazolyl, pyrazolyl, thienyl, furyl, oxazolyl, isoxazolyl, thiazolyl, isothiazolyl, thiadiazole and the like; 6-membered heterocyclic aromatic ring groups such as pyridyl, pyrazinyl, pyrimidinyl, pyridazinyl and the like; fused ring heterocyclic aromatic ring groups such as indolyl, isoindolyl, quinolinyl, isoquinolinyl, benzofuranyl, isobenzofuranyl, chromenyl and the like can be mentioned. It is preferably heterocyclic aromatic ring group containing a nitrogen atom, more preferably pyridyl.

The base to be modified is not particularly limited. For example, since the base length of the antisense oligonucleic acid of the present invention is not less than 7 nt and not more than 30 nt, the base sequence of the original antisense oligonucleic acid may be determined, the base is modified one by one and a modified base superior in a hepatotoxicity reducing effect may be determined. However, as described in the Examples below, since a favorable hepatotoxicity reducing effect tends to be seen when thymine, guanine or cytosine contained in the sequence of TGC or TCC is modified, modification of a base of the nucleic acid residue contained in these sequences can be one aim.

In the antisense oligonucleic acid according to the present invention, in particular, the base of one nucleic acid residue is modified, and thus shows reduced hepatotoxicity compared to the antisense oligonucleic acid before such modification. For example, the serum concentrations after administration of antisense oligonucleic acids of AST (aspartate aminotransferase) and ALT (alanine aminotransferase), which are indices of hepatotoxicity, are preferably not more than 60% or not more than 50%, more preferably not more than 40% or not more than 20%, further more preferably not more than 10%, particularly preferably not more than 5%, of the serum concentration measured under the same conditions except that the antisense oligonucleic acid before the above-mentioned modification is used. In addition, the serum concentration of AST after administration of the antisense oligonucleic acid of the present invention is preferably not more than 100 IU/L, more preferably not more than 40 IU/L, and the serum concentration of ALT is preferably not more than 100 IU/L, more preferably not more than 40 IU/L, further more preferably not more than 20 IU/L.

In the present disclosure, the serum concentrations of AST and ALT are determined by, for example, intravenously injecting antisense oligonucleic acid to mice or rats at a predetermined dose of about not less than 10 mg/kg body weight and not more than about 30 mg/kg body weight, collecting blood after lapse of predetermined time of not less than about 70 hours and not more than about 120 hr, and measuring same from a serum obtained by centrifugation.

The antisense oligonucleic acid according to the present invention can be produced by a conventional method. For example, since the base length of the antisense oligonucleic acid of the present invention is not less than 7 nt and not more than 30 nt, it can be easily produced using an automatic nucleic acid synthesizer.

Since the antisense oligonucleic acid according to the present invention has a base sequence complementary to the target mRNA, it can strongly inhibit translation of the target mRNA and can also reduce hepatotoxicity as described above. Therefore, the antisense oligonucleic acid is useful as a medicament for preventing or treating a disease involving a target mRNA.

The antisense oligonucleic acid of the present invention can be formulated as a parenteral preparation or a liposome preparation by blending with, for example, adjuvants generally used in the technical field of preparation formulation of medicaments such as excipient, binder, preservative, oxidation stabilizer, disintegrant, lubricant, corrigent and the like. In addition, a topical preparation such as liquid, cream, ointment and the like can be formulated by blending with, for example, a pharmaceutical carrier generally used in the pertinent technical field.

The antisense oligonucleic acids of the present invention can be administered to human and animals other than human. The dose may be appropriately adjusted depending on the patient's age, sex, body weight, condition, the kind of disease, severity, prophylactic or therapeutic use, and the like. For example, a dose per administration and per kg body weight for adult human is not less than 0.01 µg and not more than 100 g. The dose is preferably not less than 0.1 µg or not less than 1.0 µg, more preferably not less than 10 µg or not less than 100 µg, further preferably not less than 1 mg, and preferably not more than 10 g or not more than 1.0 g, more preferably not more than 100 mg or not more than 10 mg, further more preferably not more than 5 mg. The frequency of administration may be appropriately adjusted between once per month and about not more than 3 times per day.

This application claims the benefit of priority right based on a patent application No. 2017-30489 filed in Japan (filing date: Feb. 21, 2017). The contents of Japanese patent application No. 2017-30489 filed on Feb. 21, 2017 are incorporated in full herein for reference.

EXAMPLES

The present invention is more specifically described by way of Examples. However, the present invention is not

Example 1: Evaluation of Hepatotoxicity of Antisense Oligonucleic Acid (1) Selection and Synthesis of Antisense Oligonucleic Acid The mechanism of induction of hepatotoxicity which has been a problem in nucleic acid medicaments is considered to include (i) suppression of expression of non-target gene, (ii) activation of natural immunity, and (iii) signaling pathway via a biomolecule such as a protein and the like related to nucleic acid medicaments. As an antisense oligonucleic acid which avoids the above-mentioned mechanisms (i) and (ii) and induces particularly strong hepatotoxicity by the contribution of the above-mentioned mechanism (iii), #101 was selected. The synthesis of #101 having the sequence shown in Table 1 and derivative #101-C2-7 thereof was committed to Gene Design, Inc. The molecular weight of the obtained antisense oligonucleic acid was measured by mass spectrum. The theoretical value of the molecular weight of #101 was 4589.72, the measured value was 4600.61, and the theoretical value of the molecular weight of #101-C2-7 was 4605.72, the measured value was 4602.22.

| # | | |
|---|---|---|
| #101 | G T T a t g c c a c c $_m$C T A | SEQ ID NO: 1 |
| #101-02-7 | G T T a t g ζ c a c c $_m$C T A | SEQ ID NO: 2 |

In the above-mentioned sequence, capital letters indicate 2',4'-bridged nucleic acid (LNA) having the following structure, small letters indicate DNA, the base in $_m$C is 5-methylcytosine, and the base in ζ is 5-hydroxycytosine.

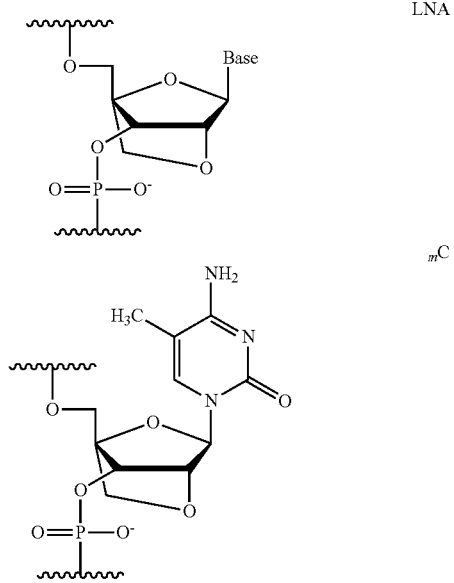

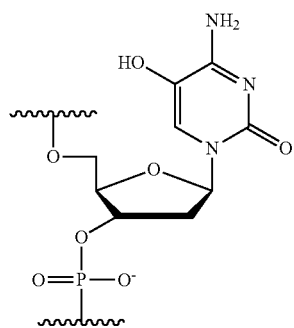

Each antisense oligonucleic acid was dissolved in physiological saline (manufactured by Otsuka Pharmaceutical Co., Ltd.) to give a 2 mg/mL solution, and the solution was cryopreserved at −30° C. until used in experiments.

(2) Hepatotoxicity Test

Five-week-old male C57BL/6NCrl mice (Nihon Charles River Co., Ltd.) were quarantined and acclimated for 1 week and used for experiments. The mice were optionally divided into 3 groups (4 mice per group), and physiological saline (manufactured by Otsuka Pharmaceutical Co., Ltd.) or each antisense oligonucleic acid solution was administered once at a dose of 10 mL/kg body weight (20 mg/kg body weight as dose of antisense oligonucleic acid) from the tail vein. On the fourth day (96 hours later), the mice were anesthetized by inhalation of 2.0 to 4.0% isoflurane (manufactured by DS Pharma Animal Health), and blood was collected from the abdominal portion of posterior vena cava as much as possible. The obtained blood was allowed to stand at room temperature for 20 to 60 min and centrifuged at 1700×g for 5 min to give serum. At the time of blood collection, when the blood volume did not reach the amount necessary for analysis, it was diluted with water for injection and used for the analysis. The concentrations of aspartate transaminase (AST) and alanine transaminase (ALT) in the obtained serum were measured using an automatic biochemical analyzer ("JCA-BM6070" manufactured by JEOL Ltd.). The breeding and experiment of the above-mentioned animal experiment were conducted in the animal experiment facility of Safety Laboratory, SHIN NIPPON BIOMEDICAL LABORATORIES, LTD. in accordance with the animal experiment regulations of SHIN NIPPON BIOMEDICAL LABORATORIES, LTD. The results are shown in FIG. 1. In FIG. 1, "*" indicates presence of a significant difference at $p<0.05$.

As shown in the results of FIG. 1, AST and ALT are enzymes to be the indices of liver dysfunction, and the serum concentrations of these enzymes due to particularly high hepatotoxicity of #101 could be reduced significantly only by changing cytosine, which is in one of the 2',4'-non-bridged nucleic acid residues in the middle part, to 5-hydroxycytosine.

Example 2: Evaluation of Hepatotoxicity of Antisense Oligonucleic Acid

Figure 2:
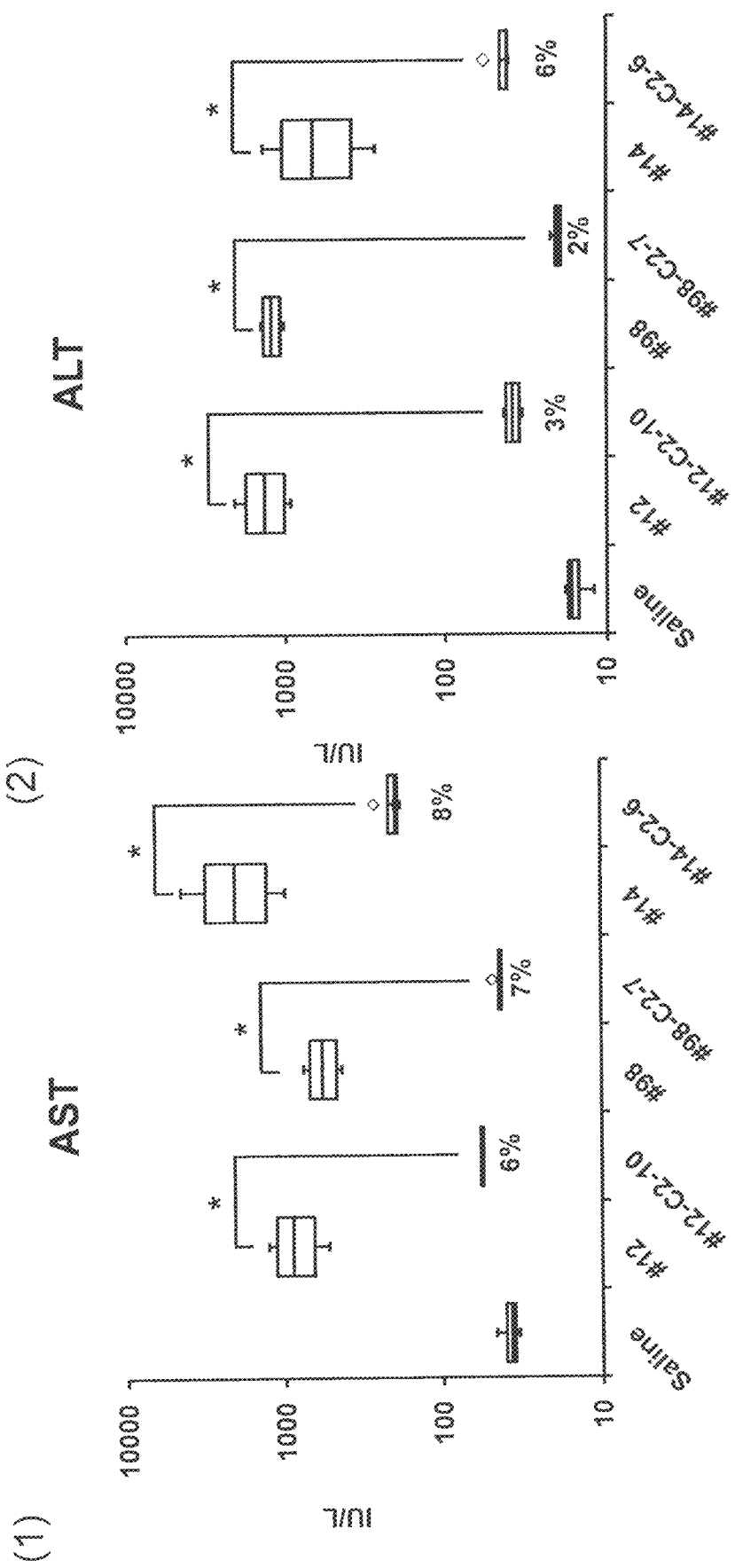
FIG. 2 is a graph showing the results of hepatotoxicity of antisense oligonucleic acid evaluated in the Example described later.

In the same manner as in the above-mentioned Example 1 except that #12, #98, #14 or derivatives thereof which induce strong hepatotoxicity by contribution of the above-mentioned hepatotoxicity induction mechanism (iii) were used instead of antisense oligonucleic acid #101, the hepatotoxicity was evaluated. The theoretical value of the molecular weight of #12 was 4614.73 and the measured value was 4614.27, the theoretical value of the molecular weight of #12-C2-10 was 4630.73 and the measured value was 4627.86, the theoretical value of the molecular weight of #98 was 4613.75 and the measured value was 4612.79, the theoretical value of the molecular weight of #98-C2-7 was 4629.75 and the measured value was 4631.10, the theoretical value of the molecular weight of #14 was 4606.71 and the measured value was 4605.66, and the theoretical value of the molecular weight of #14-C2-6 was 4622.71 and the measured value was 4619.72. The sequence of each antisense oligonucleic acid used in this Example is shown in Table 2, and the measurement results of the hepatotoxicity are shown in FIG. 2. In FIG. 2, "*" indicates presence of a significant difference at p<0.05.

TABLE 2

| # | Sequence | SEQ ID |
|---|---|---|
| #12 | G T $_m$C c g c a t g c c T A A | SEQ ID NO: 3 |
| #12-C2-10 | G T $_m$C c g c a t g ζ c T A A | SEQ ID NO: 4 |
| #98 | G A T a t g c c c t a $_m$C T A | SEQ ID NO: 5 |
| #98-C2-7 | G A T a t g ζ c c t a $_m$C T A | SEQ ID NO: 6 |
| #14 | G T A t g c c t c c g T T A | SEQ ID NO: 7 |
| #14-C2-6 | G T A t g ζ c t c c g T T A | SEQ ID NO: 8 |

As shown in the results of FIG. 2, the serum concentrations of AST and ALT could be reduced significantly only by changing cytosine, which is in one of the 2',4'-non-bridged nucleic acid residues in the middle part, to 5-hydroxycytosine also in other antisense oligonucleic acids #12, #98 and #14 having high hepatotoxicity. The serum concentrations of AST and ALT were reduced to several percents by the above-mentioned mutation, though not as much as that in #101 having particularly high hepatotoxicity.

Example 3: Evaluation of Hepatotoxicity and Activity of Antisense Oligonucleic Acid GR (Glucocortiocoid Receptor) is one kind of steroid receptors and works as a receptor for the steroid hormone hydrocortisone. It also undergoes nuclear translocation in a ligand-dependent manner and also works as a transcription factor. Therefore, Posi12 (Nucleic Acid Ther., 2012, 22, 5, 344-359) was selected as an antisense oligonucleic acid targeting same, and the synthesis of Posi12 having the sequence shown in Table 3 and its derivative Posi12-C2-11 was committed to Gene Design, Inc. The theoretical value of the molecular weight of Posi12 was 4611.71 and the measured value was 4610.81, and the theoretical value of the molecular weight of Posi12-C2-11 was 4627.71 and the measured value was 4625.65.

TABLE 3

| | Sequence | SEQ ID |
|---|---|---|
| Posi12 | G T $_m$C t c t t t a c c T G G | SEQ ID NO: 9 |
| Posi12-02-11 | G T $_m$C t c t t t a c ζ T G G | SEQ ID NO: 10 |

With regard to each of the obtained antisense oligonucleic acids, the ALT concentration in mouse serum was measured in the same manner as in the above-mentioned Example 1 (2). The results are shown in FIG. 3 (1).

In addition, the GR gene expression-suppressing activity of each antisense oligonucleic acid was measured. To be specific, after blood was collected in the above-mentioned hepatotoxicity test, the mouse was euthanized by freezing, and the liver was removed and the weight was measured. About 100 mg was collected as a sample from a site where no abnormality was found macroscopically in the excised liver. The weight of the collected sample was measured, the sample was frozen in liquid nitrogen and stored in an ultra low temperature freezer. The cryopreserved liver sample was homogenized as much as possible using a homogenizer (Shake Master auto, Bio Medical Science Inc.) and TRIzol reagent (Thermo Fisher Scientific) under ice-cooling and total RNA was extracted. The UV absorption spectrum of the extracted total RNA was measured using Nano Vue or Nano Vue Plus (GE Healthcare), and the purity was calculated from the RNA concentration and O.D.260/O.D.280 ratio. Quantitative PCR was performed on total RNA using One Step SYBR PrimeScript RT-PCR Kit (Takara) and Applied Biosystems 7500 (Life Technologies Japan Ltd), the expression ratio of the target gene in the antisense oligonucleic acid administration group relative to the saline administration group was calculated, and the activity was evaluated. The results are shown in FIG. 3 (2).

Figure 3:
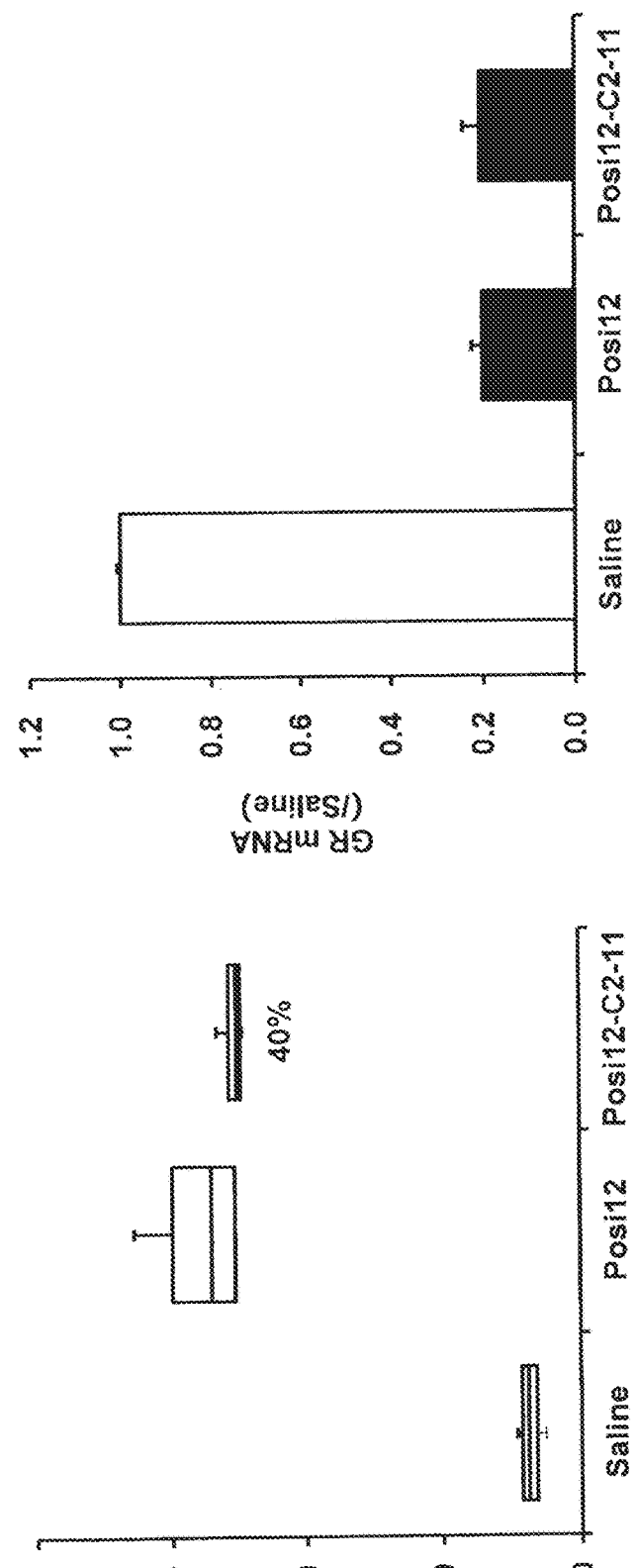
FIG. 3 is a graph showing the results of hepatotoxicity of antisense oligonucleic acid and GR gene expression-suppressing activity evaluated in the Example described later.

As shown in the results of FIG. 3 (1), the hepatotoxicity by Posi12 was reduced to 40% by only changing cytosine, which is in one of the 2',4'-non-bridged nucleic acid residues in the middle part, to 5-hydroxycytosine. On the other hand, as shown in the results of FIG. 3 (2), GR gene expression-suppressing activity did not change even when cytosine, which is in one of the 2',4'-non-bridged nucleic acid residues in the middle part of Posi12, was changed to 5-hydroxycytosine. Thus, according to the present invention, hepatotoxicity can be reduced without reducing the activity of antisense oligonucleic acid.

Example 4: Evaluation of Hepatotoxicity and Activity of Antisense Oligonucleic Acid Posi14 (Nucleic Acid Ther., 2012, 22, 5, 344-359) was selected as an antisense oligonucleic acid targeting mouse GR, and the synthesis of Posi14 having the sequence shown in Table 4 and its derivative Posi14-C2-6 was committed to Gene Design, Inc. The theoretical value of the molecular weight of Posi14 was 4691.78 and the measured value was 4691.10, and the theoretical value of the molecular weight of Posi14-C2-6 was 4707.78 and the measured value was 4705.24.

TABLE 4

| | Sequence | SEQ ID |
|---|---|---|
| Posi14 | A G G t g c t t t g g T $_m$C T | SEQ ID NO: 11 |
| Posi14-C2-6 | A G G t g ζ t t t g g T $_m$C T | SEQ ID NO: 12 |

With regard to each of the obtained antisense oligonucleic acids, the ALT concentration in mouse serum and GR gene expression-suppressing activity were measured in the same manner as in the above-mentioned Example 3. The results are shown in FIG. 4.

Figure 4:
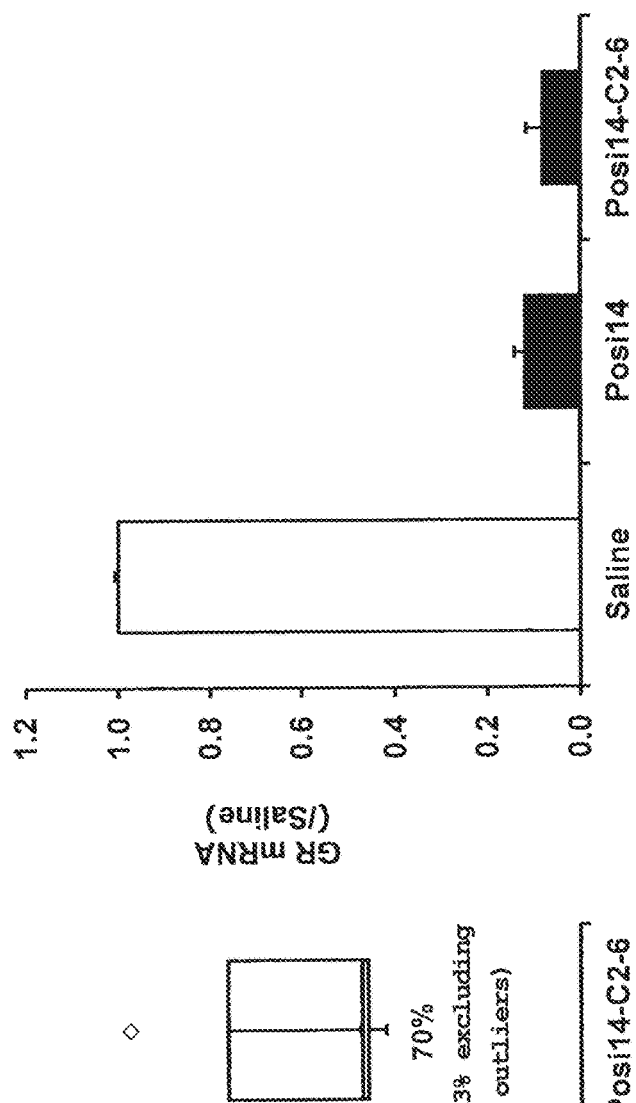
FIG. 4 is a graph showing the results of hepatotoxicity of antisense oligonucleic acid and GR gene expression-suppressing activity evaluated in the Example described later.
Figure 4:
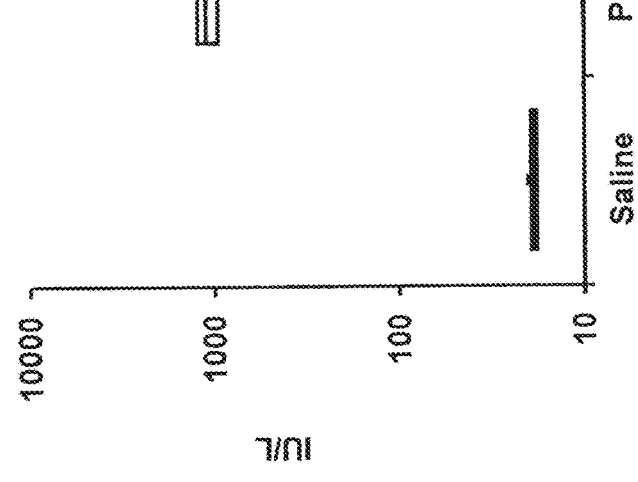

As shown in the results of FIG. 4 (1), the hepatotoxicity by Posi14 was reduced to 70% by only changing cytosine, which is in one of the 2',4'-non-bridged nucleic acid residues in the middle part, to 5-hydroxycytosine, and the degree of reduction became 13% by removing abnormal measurement values. On the other hand, as shown in the results of FIG. 4 (2), GR gene expression-suppressing activity did not change even when cytosine, which is in one of the 2',4'-non-bridged nucleic acid residues in the middle part, was changed to 5-hydroxycytosine. Thus, according to the present invention, hepatotoxicity can be reduced without reducing the activity of antisense oligonucleic acid.

Example 5: Evaluation of Hepatotoxicity and Activity of Antisense Oligonucleic Acid PCSK9 (Pro-protein Convertase Subtilisin Kexin 9) is one kind of endoproteases. It reduces LDL uptake by binding to and degrading the receptor for LDL, thus resulting in an increase in the blood LDL level. Posi15 was selected as an antisense oligonucleic acid targeting mouse PCSK9 gene, and the synthesis of Posi15 having the sequence shown in Table 5 and its derivatives Posi15-C2-4 and Posi15-C2-11 was committed to Gene Design, Inc. The theoretical value of the molecular weight of Posi15 was 4586.77 and the measured value was 4586.73, the theoretical value of the molecular weight of Posi15-C2-4 was 4602.77 and the measured value was 4600.61, and the theoretical value of the molecular weight of Posi15-C2-11 was 4602.77 and the measured value was 4602.09.

TABLE 5

| Posi15 | A $_m$C A c c a a g t t c T $_m$C $_m$C | SEQ ID NO: 13 |
|---|---|---|
| Posi15-C2-4 | A $_m$C A ζ c a a g t t c T $_m$C $_m$C | SEQ ID NO: 14 |
| Posi15-C2-11 | A $_m$C A c c a a g t t ζ T $_m$C $_m$C | SEQ ID NO: 15 |

With regard to each of the obtained antisense oligonucleic acids, the ALT concentration in mouse serum and PCSK9 gene expression-suppressing activity were measured in the same manner as in the above-mentioned Example 3. The results are shown in FIG. 5.

Figure 5:
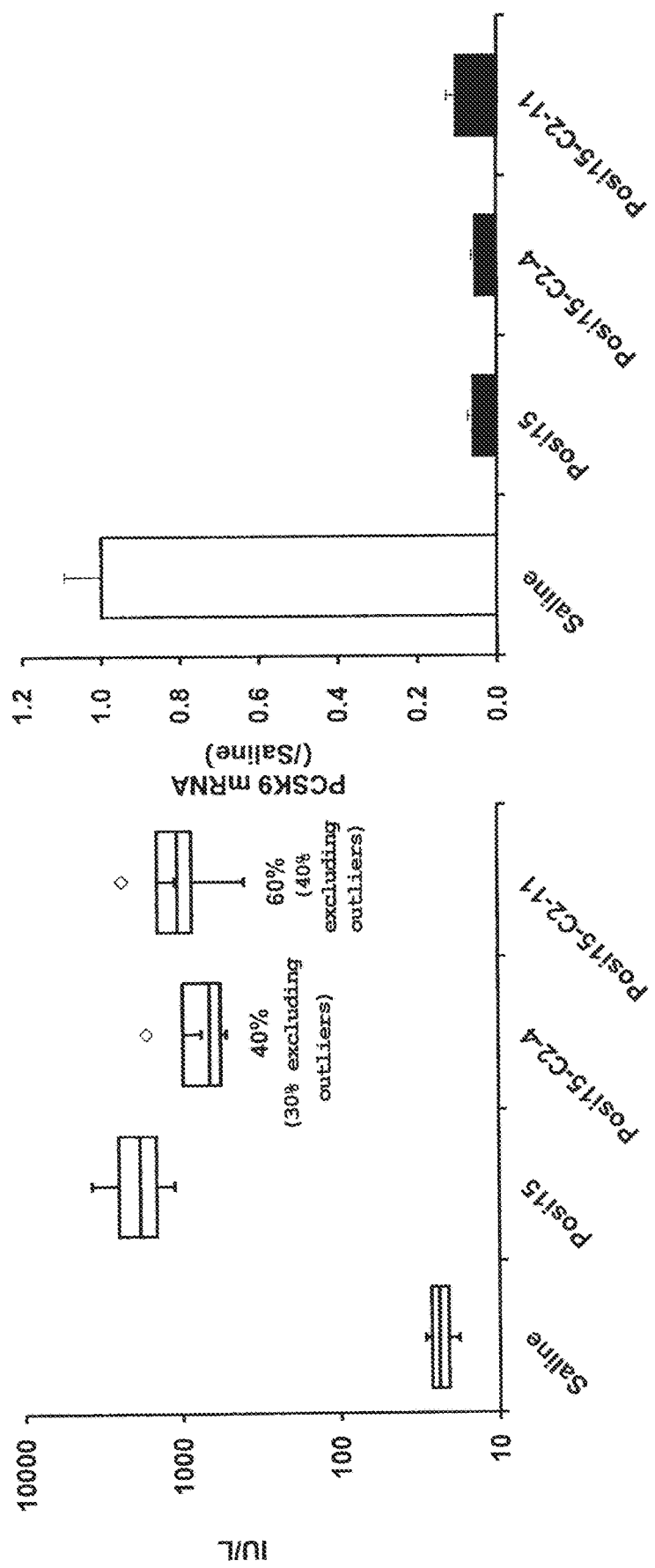
FIG. 5 is a graph showing the results of hepatotoxicity of antisense oligonucleic acid and PCSK9 gene expression-suppressing activity evaluated in the Example described later.

As shown in the results of FIG. 5 (1), the hepatotoxicity by Posi15 was reduced to 40% or 60% by only changing cytosine, which is in one of the 2',4'-non-bridged nucleic acid residues in the middle part, to 5-hydroxycytosine, and the degree of reduction became 30% or 40% by removing abnormal measurement values. On the other hand, as shown in the results of FIG. 5 (2), PCSK9 gene expression-suppressing activity almost did not change even when cytosine, which is in one of the 2',4'-non-bridged nucleic acid residues in the middle part of Posi15, was changed to 5-hydroxycytosine. Thus, according to the present invention, hepatotoxicity can be reduced without reducing the activity of antisense oligonucleic acid.

Example 6: Evaluation of Hepatotoxicity and Activity of Antisense Oligonucleic Acid Posi17 was selected as an antisense oligonucleic acid targeting mouse PCSK9 gene, and the synthesis of Posi17 having the sequence shown in Table 6 and its derivative Posi17-C2-10 was committed to Gene Design, Inc. The theoretical value of the molecular weight of Posi17 was 4300.54 and the measured value was 4300.92, and the theoretical value of the molecular weight of Posi17-C2-10 was 4316.54 and the measured value was 4314.46.

TABLE 6

| Posi17 | $_m$C T g t g a t g a c $_m$C T $_m$C | SEQ ID NO: 16 |
|---|---|---|
| Posi17-C2-10 | $_m$C T g t g a t g a ζ $_m$C T $_m$C | SEQ ID NO: 17 |

Figure 6:
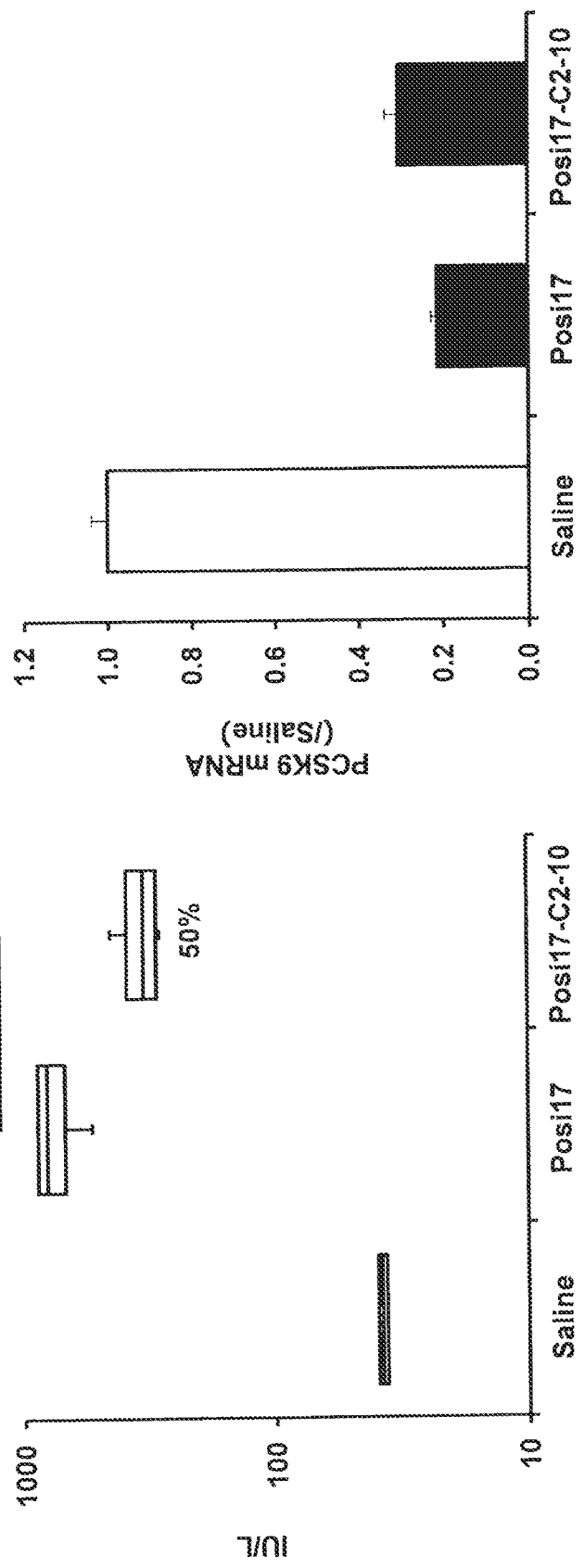
FIG. 6 is a graph showing the results of hepatotoxicity of antisense oligonucleic acid and PCSK9 gene expression-suppressing activity evaluated in the Example described later.

With regard to each of the obtained antisense oligonucleic acids, the ALT concentration in mouse serum and PCSK9 gene expression-suppressing activity were measured in the same manner as in the above-mentioned Example 3. The results are shown in FIG. 6. In FIG. 6, "*" indicates presence of a significant difference at $p<0.05$.

As shown in the results of FIG. 6 (1), the hepatotoxicity by Posi17 was significantly reduced to 50% by only changing cytosine, which is in one of the 2',4'-non-bridged nucleic acid residues in the middle part, to 5-hydroxycytosine. On the other hand, as shown in the results of FIG. 6 (2), PCSK9 gene expression-suppressing activity almost did not change even when cytosine, which is in one of the 2',4'-non-bridged nucleic acid residues in the middle part of Posi17, was changed to 5-hydroxycytosine. Thus, according to the present invention, hepatotoxicity can be reduced without reducing the activity of antisense oligonucleic acid.

Example 7: Evaluation of Hepatotoxicity and Activity of Antisense Oligonucleic Acid Rps6kb2 (Ribosomal protein S6 kinase beta-2) is a serine-threonine kinase identified as an enzyme that phosphorylates ribosome protein S6, activated by stimulation with growth factor, stress and the like, and regulates cell cycle and protein synthesis. No. 97 was selected as an antisense oligonucleic acid targeting same, and the synthesis of No. 97 having the sequence shown in Table 7 and its derivatives No. 97-C2-7, No. 97-C2-9 and No. 97-C2-10 was committed to Gene Design, Inc. The theoretical value of the molecular weight of No. 97 was 4182.40 and the measured value was 4183.06, the theoretical value of the molecular weight of No. 97-C2-7 was 4198.40 and the measured value was 4197.54, the theoretical value of the molecular weight of No. 97-C2-9 was 4198.40 and the measured value was 4196.60, and the theoretical value of the molecular weight of No. 97-C2-10 was 4198.40 and the measured value was 4199.40.

TABLE 7

| No.97 | $_m$C G c c c t c g c c $_m$C T $_m$C | SEQ ID NO: 18 |
|---|---|---|
| No.97-C2-7 | $_m$C G c c c t ζ g c c $_m$C T $_m$C | SEQ ID NO: 19 |
| No.97-C2-9 | $_m$C G c c c t c g ζ c $_m$C T $_m$C | SEQ ID NO: 20 |
| No.97-C2-10 | $_m$C G c c c t c g c ζ $_m$C T $_m$C | SEQ ID NO: 21 |

Figure 7:
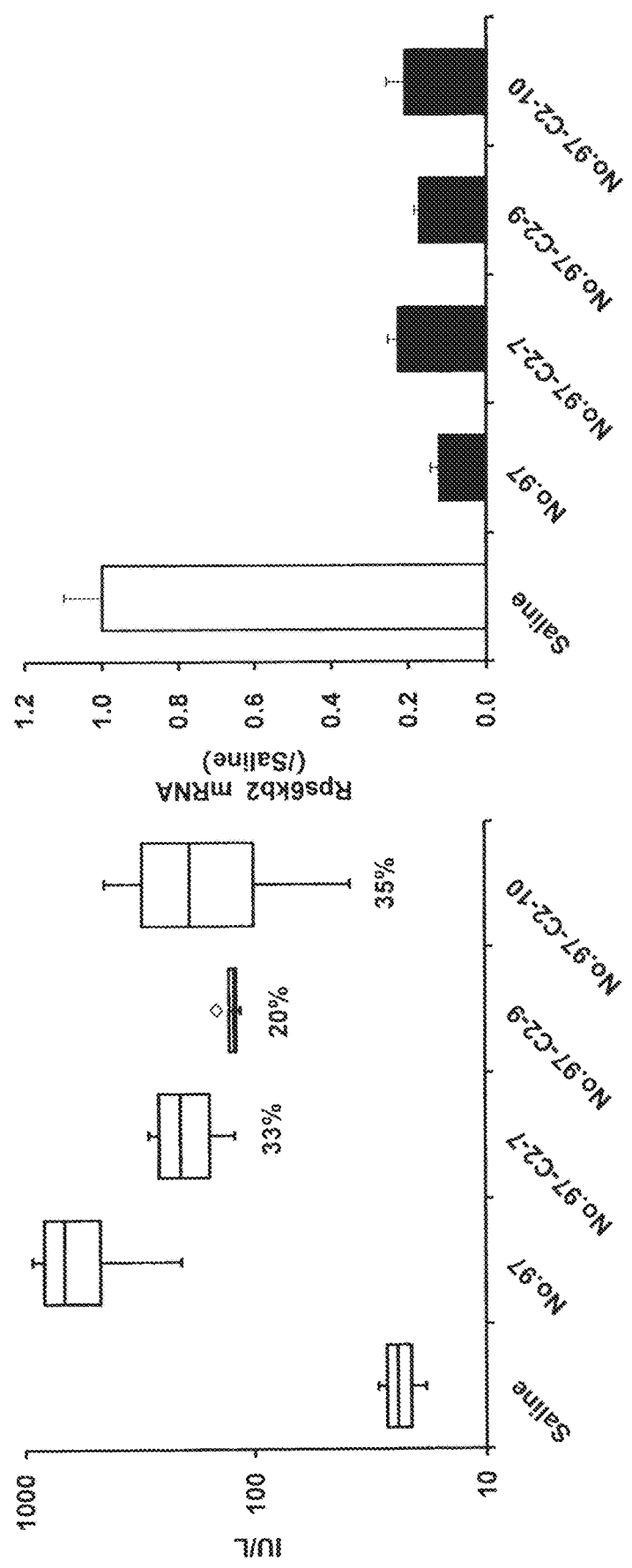
FIG. 7 is a graph showing the results of hepatotoxicity of antisense oligonucleic acid and Rps6kb2 gene expression-suppressing activity evaluated in the Example described later.

With regard to each of the obtained antisense oligonucleic acids, the ALT concentration in mouse serum and Rps6kb2 expression-suppressing activity were measured in the same manner as in the above-mentioned Example 3. The results are shown in FIG. 7. In FIG. 7, "*" indicates presence of a significant difference at p<0.05.

As shown in the results of FIG. 7 (1), the hepatotoxicity by No. 97 was reduced to 33%, 20% or 35% by only changing cytosine, which is in one of the 2',4'-non-bridged nucleic acid residues in the middle part, to 5-hydroxycytosine. On the other hand, as shown in the results of FIG. 7 (2), GR gene expression-suppressing activity almost did not change even when cytosine, which is in one of the 2',4'-non-bridged nucleic acid residues in the middle part of No. 97, was changed to 5-hydroxycytosine. Thus, according to the present invention, hepatotoxicity can be reduced without reducing the activity of antisense oligonucleic acid.

Example 8: Evaluation of Hepatotoxicity of Antisense Oligonucleic Acid

Figure 8:
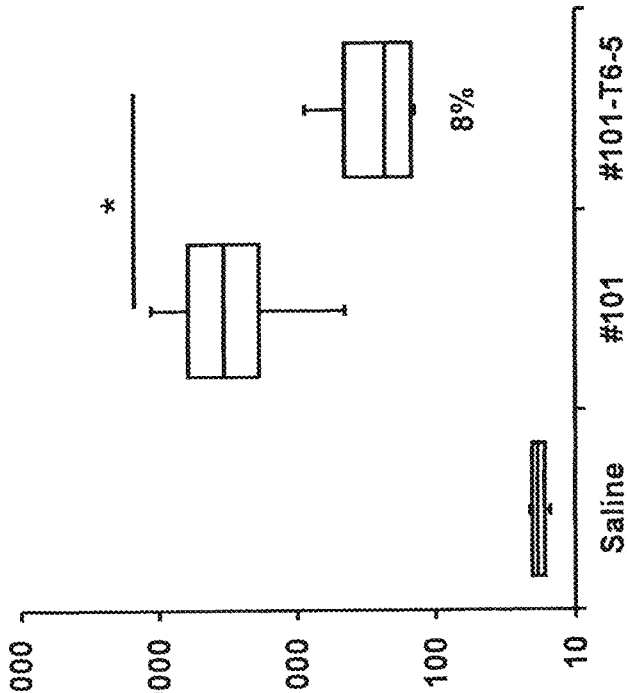
FIG. 8 is a graph showing the results of hepatotoxicity of antisense oligonucleic acid evaluated in the Example described later.
Figure 8:
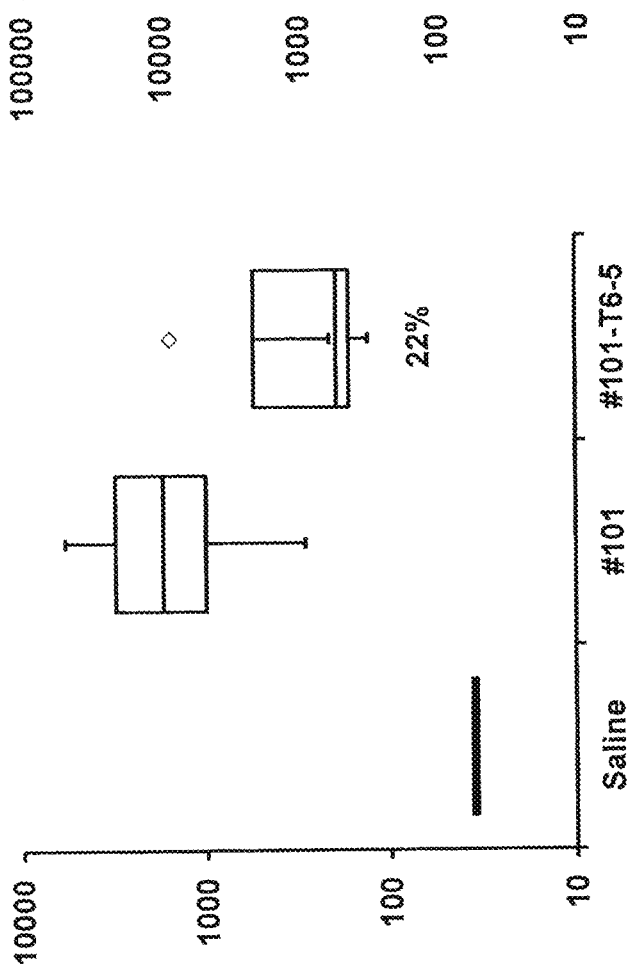

In the same manner as in the above-mentioned Example 1 except that #101-T6-5 was used as the derivative of antisense oligonucleic acid #101, hepatotoxicity was evaluated. The theoretical value of the molecular weight of #101-T6-5 was 4605.78 and the measured value was 4605.10. The sequence of each antisense oligonucleic acid used in this Example is shown in Table 8, and the measurement results of the hepatotoxicity are shown in FIG. 8. In FIG. 8, "*" indicates presence of a significant difference at p<0.05.

TABLE 8

| #101 | G T T a t g c c a c c $_m$C T A | SEQ ID NO: 22 |
| #101-T6-5 | G T T a κ g c c a c c $_m$C T A | SEQ ID NO: 23 |

In the above-mentioned sequences, the base in κ is 2-thiocarbonylthymine and κ has the following structure:

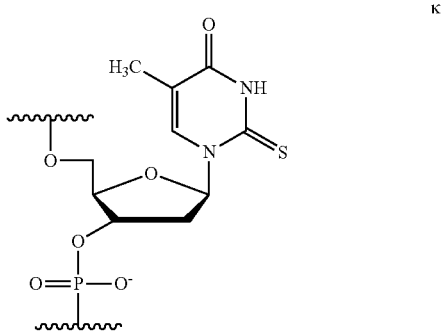 [SMILES: *OC[C@H]1O[C@@H](n2cc(C)c(=O)[nH]c2=S)C[C@H]1OP(*)(=O)[O-]]

κ

As shown in the results of FIG. 8, the serum concentrations of AST and ALT could be reduced by converting thymine, which is in one of the 2',4'-non-bridged nucleic acid residues in the middle part of antisense oligonucleic acid #101 having very high hepatotoxicity, to 2-thiocarbonylthymine.

Example 9: Evaluation of Hepatotoxicity of Antisense Oligonucleic Acid

Figure 9:
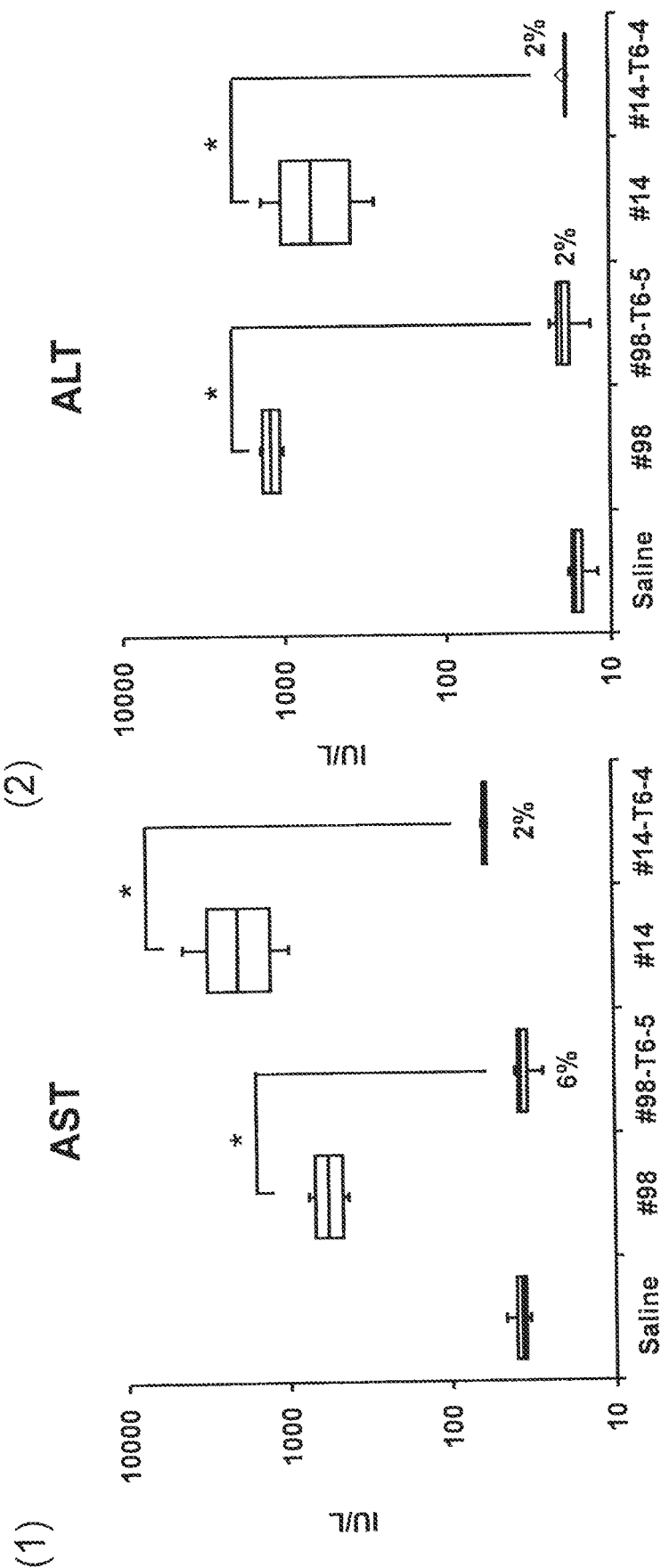
FIG. 9 is a graph showing the results of hepatotoxicity of antisense oligonucleic acid evaluated in the Example described later.

In the same manner as in the above-mentioned Example 1 except that #98, #14 or a derivative thereof was used instead of antisense oligonucleic acid #101, hepatotoxicity was evaluated. The theoretical value of the molecular weight of #98-T6-5 was 4629.81 and the measured value was 4631.05, and the theoretical value of the molecular weight of #14-T6-4 was 4622.77 and the measured value was 4623.11. The sequence of each antisense oligonucleic acid used in this Example is shown in Table 9, and the measurement results of the hepatotoxicity are shown in FIG. 9. In FIG. 9, "*" indicates presence of a significant difference at p<0.05.

TABLE 9

| #98 | G A T a t g c c c t a $_m$C T A | SEQ ID NO: 24 |
| #98-T6-5 | G A T a κ g c c c t a $_m$C T A | SEQ ID NO: 25 |
| #14 | G T A t g c c t c c g T T A | SEQ ID NO: 26 |
| #14-T6-4 | G T A κ g c c t c c g T T A | SEQ ID NO: 27 |

The serum concentrations of AST and ALT could be reduced significantly only by changing thymine, which is in one of the 2',4'-non-bridged nucleic acid residues in the middle part, to 2-thiocarbonylthymine also in other antisense oligonucleic acids #98 and #14 having high hepatotoxicity.

Example 10: Evaluation of Hepatotoxicity and Activity of Antisense Oligonucleic Acid Posi12 (Nucleic Acid Ther., 2012, 22, 5, 344-359) was selected as an antisense oligonucleic acid targeting mouse GR, and the synthesis of Posi12 having the sequence shown in Table 10 and its derivative Posi12-T6-4 was committed to Gene Design, Inc. The theoretical value of the molecular weight of Posi12-T6-4 was 4627.77 and the measured value was 4629.03.

TABLE 10

| Posi12 | G T $_m$C t c t t t a c c T G G | SEQ ID NO: 28 |
| Posi12-T6-4 | G T $_m$C κ c t t t a c c T G G | SEQ ID NO: 29 |

Figure 10:
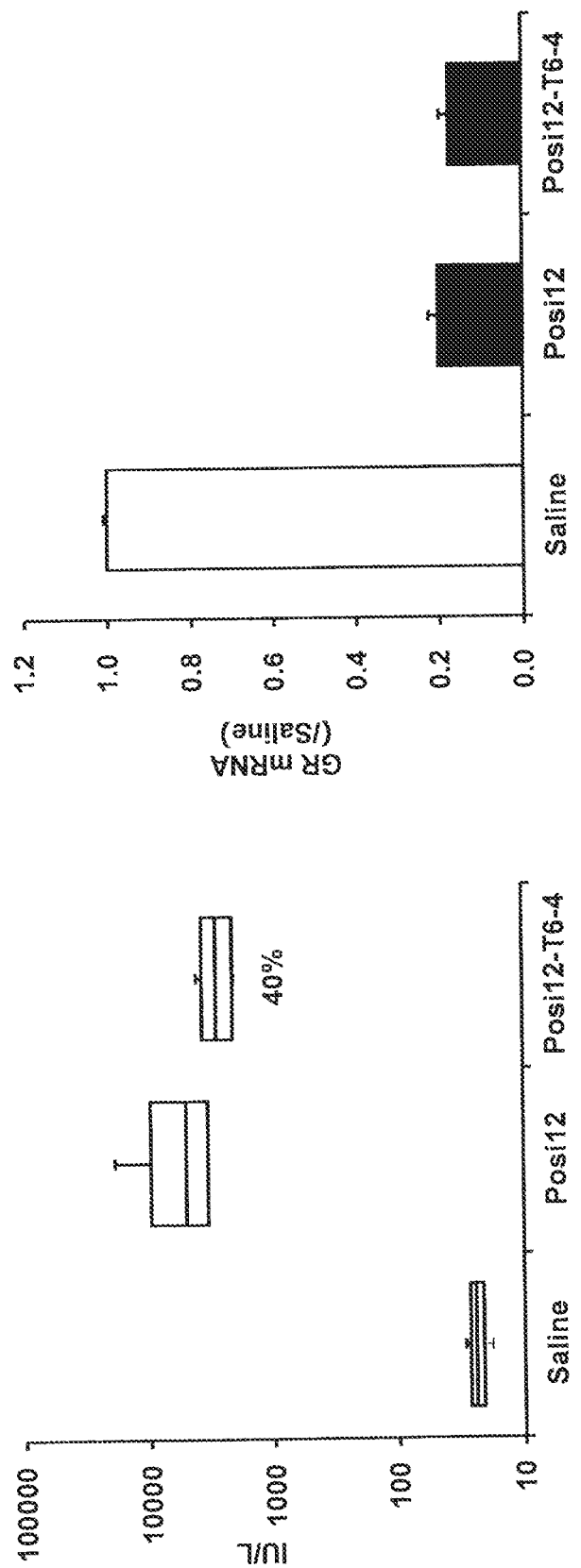
FIG. 10 is a graph showing the results of hepatotoxicity of antisense oligonucleic acid and GR gene expression-suppressing activity evaluated in the Example described later.

With regard to each of the obtained antisense oligonucleic acids, the ALT concentration in mouse serum and GR gene expression-suppressing activity were measured in the same manner as in the above-mentioned Example 3. The results are shown in FIG. 10. In FIG. 10, "*" indicates presence of a significant difference at p<0.05.

As shown in the results of FIG. 10 (1), the hepatotoxicity by Posi12 was reduced to 40% by only changing thymine, which is in one of the 2',4'-non-bridged nucleic acid residues in the middle part, to 2-thiocarbonylthymine. On the other hand, as shown in the results of FIG. 10 (2), GR gene expression-suppressing activity did not change even when thymine, which is in one of the 2',4'-non-bridged nucleic acid residues in the middle part of Posi12, was changed to 2-thiocarbonylthymine. Thus, according to the present invention, hepatotoxicity can be reduced without reducing the activity of antisense oligonucleic acid.

Example 11: Evaluation of Hepatotoxicity and Activity of Antisense Oligonucleic Acid Posi14 (Nucleic Acid Ther., 2012, 22, 5, 344-359) was selected as an antisense oligonucleic acid targeting mouse GR, and the synthesis of Posi14 having the sequence shown in Table 11 and its derivative Posi14-T6-4 was committed to Gene Design, Inc. The theoretical value of the molecular weight of Posi14-T6-4 was 4707.84 and the measured value was 4708.38.

TABLE 11

| Posi14 | A G G t g c t t t g g T $_m$C T | SEQ ID NO: 30 |
|---|---|---|
| Posi14-T6-4 | A G G κ g c t t t g g T $_m$C T | SEQ ID NO: 31 |

Figure 11:
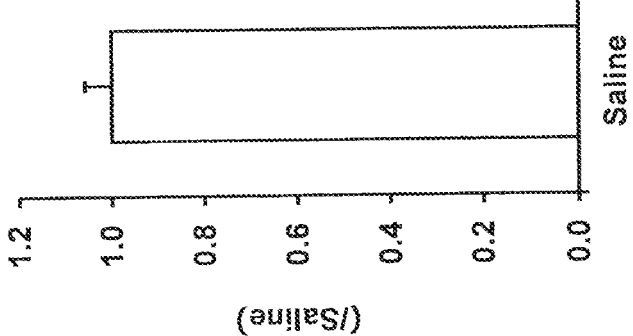
FIG. 11 is a graph showing the results of hepatotoxicity of antisense oligonucleic acid and GR gene expression-suppressing activity evaluated in the Example described later.
Figure 11:
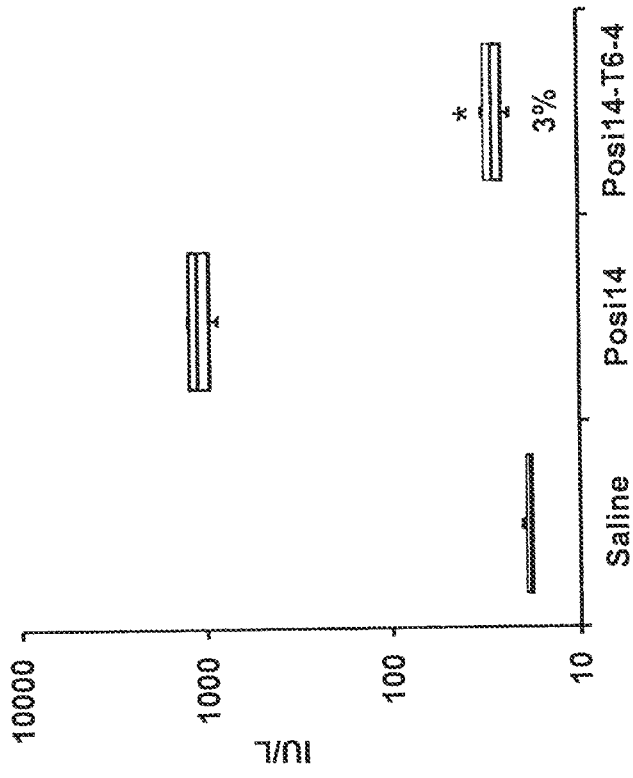

With regard to each of the obtained antisense oligonucleic acids, the ALT concentration in mouse serum and GR gene expression-suppressing activity were measured in the same manner as in the above-mentioned Example 3. The results are shown in FIG. 11. In FIG. 11, "*" indicates presence of a significant difference at p<0.05.

As shown in the results of FIG. 11 (1), the hepatotoxicity by Posi14 was reduced to 3% by only changing thymine, which is in one of the 2',4'-non-bridged nucleic acid residues in the middle part, to 2-thiocarbonylthymine. On the other hand, as shown in the results of FIG. 11 (2), GR gene expression-suppressing activity did not change even when thymine, which is in one of the 2',4'-non-bridged nucleic acid residues in the middle part of Posi14, was changed to 2-thiocarbonylthymine. Thus, according to the present invention, hepatotoxicity can be reduced without reducing the activity of antisense oligonucleic acid.

Example 12: Evaluation of Hepatotoxicity and Activity of Antisense Oligonucleic Acid Posi17 (Nucleic Acid Ther., 2012, 22, 5, 344-359) was selected as an antisense oligonucleic acid targeting mouse PCSK9, and the synthesis of Posi17 having the sequence shown in Table 12 and its derivative Posi17-T6-4 was committed to Gene Design, Inc. The theoretical value of the molecular weight of Posi17-T6-4 was 4316.60 and the measured value was 4316.08.

TABLE 12

| Posi17 | $_m$C T g t g a t g a c $_m$C T $_m$C | SEQ ID NO: 32 |
|---|---|---|
| Posi17-T6-4 | $_m$C T g κ g a t g a c $_m$C T $_m$C | SEQ ID NO: 33 |

Figure 12:
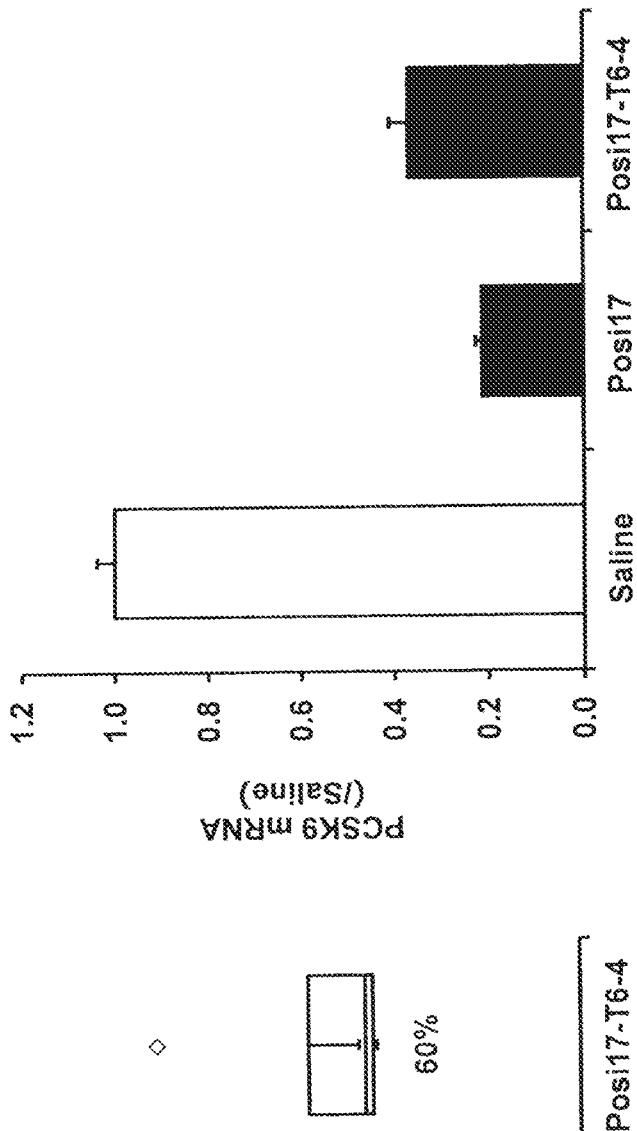
FIG. 12 is a graph showing the results of hepatotoxicity of antisense oligonucleic acid and PCSK9 gene expression-suppressing activity evaluated in the Example described later.
Figure 12:
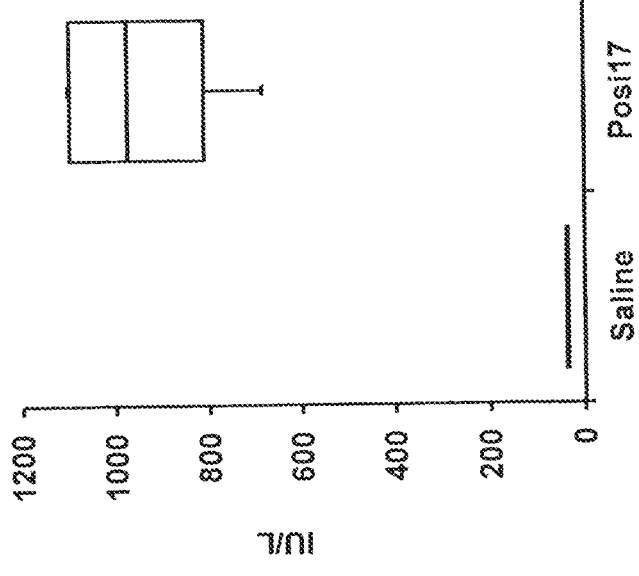

With regard to each of the obtained antisense oligonucleic acids, the ALT concentration in mouse serum and PCSK9 gene expression-suppressing activity were measured in the same manner as in the above-mentioned Example 3. The results are shown in FIG. 12. In FIG. 12, "*" indicates presence of a significant difference at p<0.05.

As shown in the results of FIG. 12 (1), the hepatotoxicity by Posi17 was reduced to 60% by only changing thymine, which is in one of the 2',4'-non-bridged nucleic acid residues in the middle part, to 2-thiocarbonylthymine. On the other hand, as shown in the results of FIG. 12 (2), PCSK9 gene expression-suppressing activity almost did not change even when thymine, which is in one of the 2',4'-non-bridged nucleic acid residues in the middle part of Posi17, was changed to 2-thiocarbonylthymine. Thus, according to the present invention, hepatotoxicity can be reduced without reducing the activity of antisense oligonucleic acid.

Example 13: Evaluation of Hepatotoxicity of Antisense Oligonucleic Acid

Figure 13:
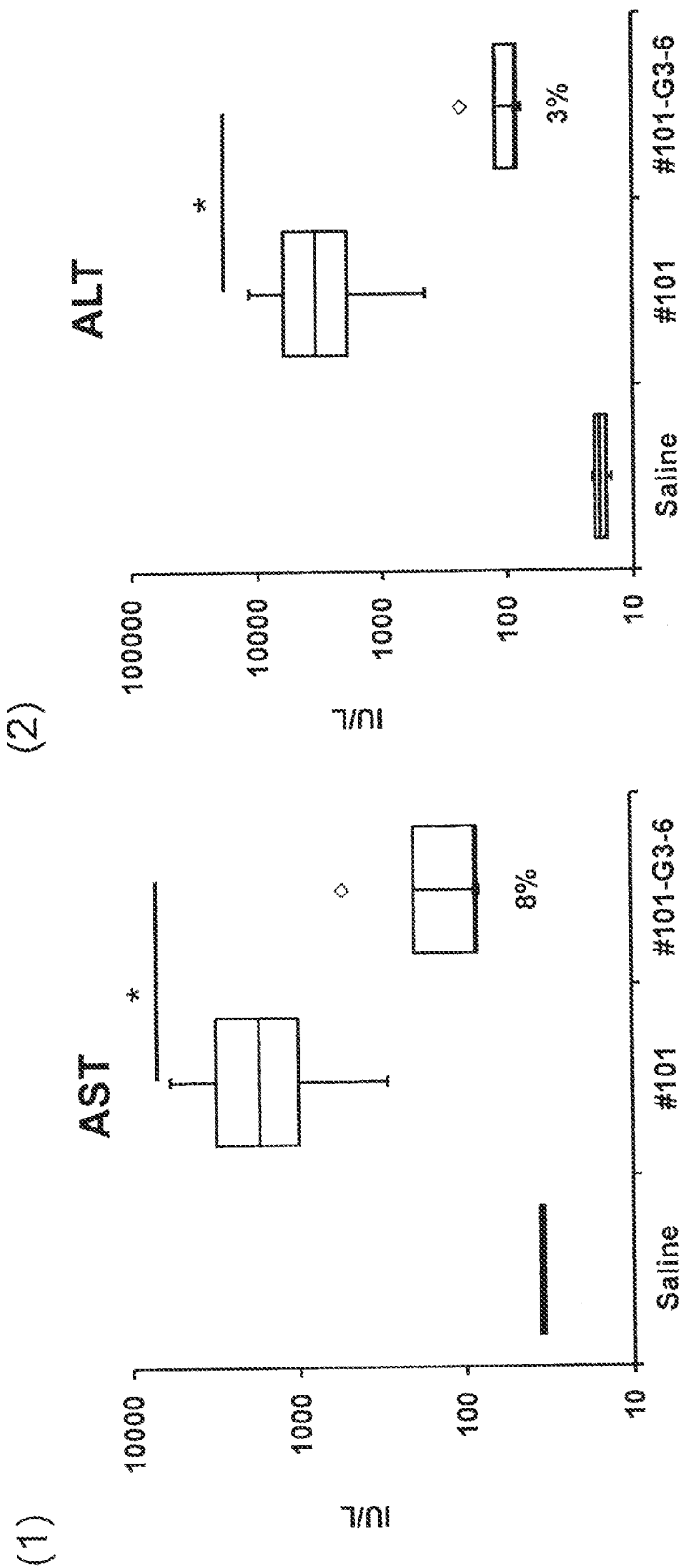
FIG. 13 is a graph showing the results of hepatotoxicity of antisense oligonucleic acid evaluated in the Example described later.

In the same manner as in the above-mentioned Example 1 except that #101-G3-6 was used as the derivative of antisense oligonucleic acid #101, hepatotoxicity was evaluated. The theoretical value of the molecular weight of #101-G3-6 was 4604.73 and the measured value was 4605.45. The sequence of each antisense oligonucleic acid used in this Example is shown in Table 13, and the measurement results of the hepatotoxicity are shown in FIG. 13. In FIG. 13, "*" indicates presence of a significant difference at p<0.05.

TABLE 13

| #101 | G T T a t g c c a c c $_m$C T A | SEQ ID NO: 34 |
|---|---|---|
| #101-G3-6 | G T T a t λ c c a c c $_m$C T A | SEQ ID NO: 35 |

In the above-mentioned sequences, the base in λ is 8-aminoguanine and λ has the following structure:

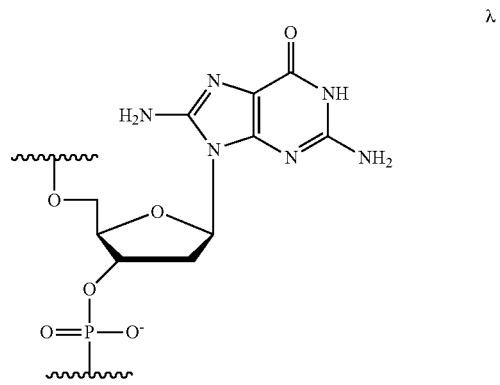 [SMILES: *OC[C@H]1O[C@@H](n2c(N)nc3c(=O)[nH]c(N)nc32)C[C@H]1OP(*)(=O)[O-]]

As shown in the results of FIG. 13, the serum concentrations of AST and ALT could be reduced by only converting guanine, which is in one of the 2',4'-non-bridged nucleic acid residues in the middle part of antisense oligonucleic acid #101 having very high hepatotoxicity, to 8-aminoguanine.

Example 14: Evaluation of Hepatotoxicity of Antisense Oligonucleic Acid

Figure 14:
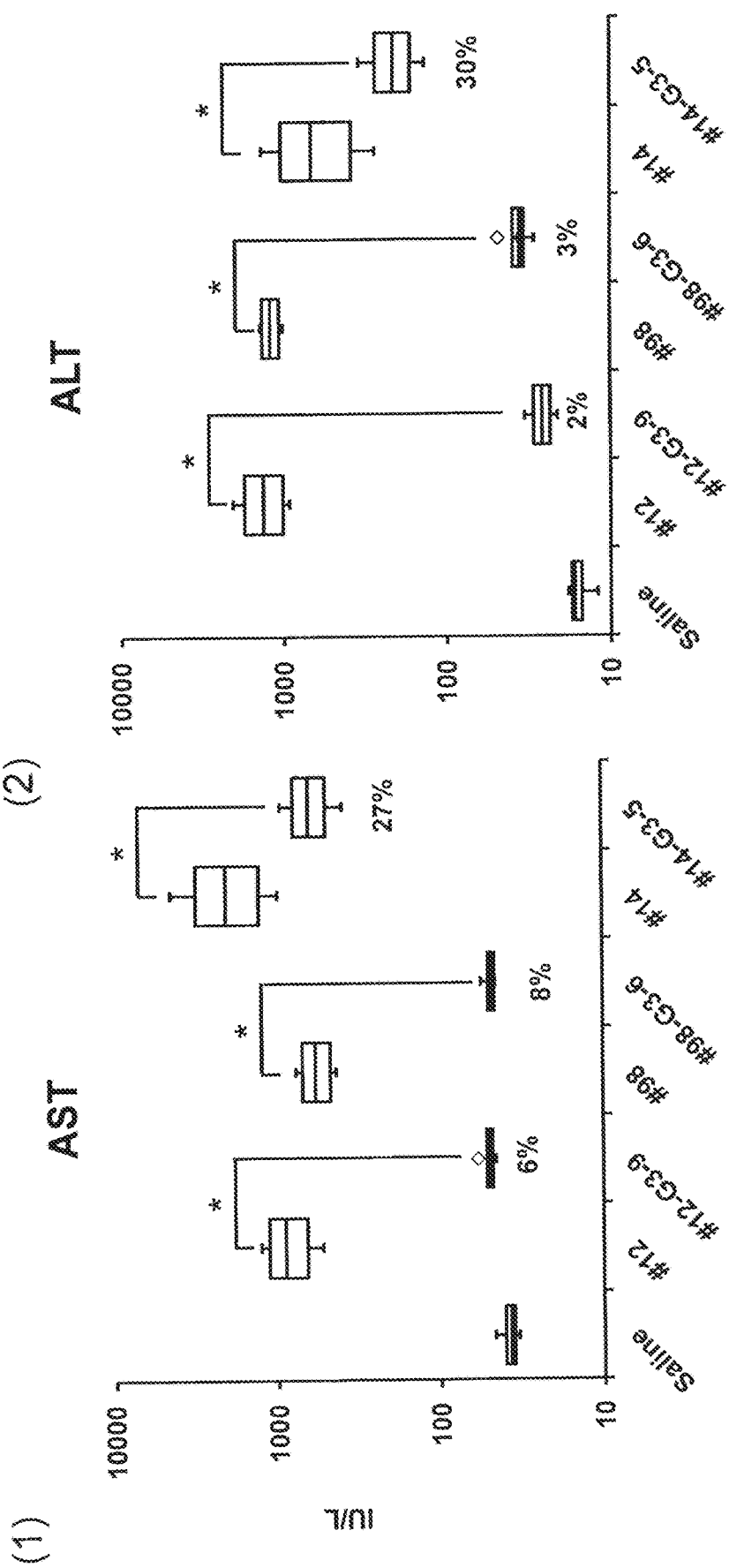
FIG. 14 is a graph showing the results of hepatotoxicity of antisense oligonucleic acid evaluated in the Example described later.

In the same manner as in the above-mentioned Example 1 except that #12, #98, #14 or derivatives thereof were used, hepatotoxicity was evaluated. The theoretical value of the molecular weight of #12-G3-9 was 4629.74 and the measured value was 4628.19, the theoretical value of the molecular weight of #98-G3-6 was 4628.76 and the measured value was 4628.93, and the theoretical value of the molecular weight of #14-G3-5 was 4621.72 and the measured value was 4621.39. The sequence of each antisense oligonucleic acid used in this Example is shown in Table 14, and the measurement results of the hepatotoxicity are shown in FIG. 14. In FIG. 14, "*" indicates presence of a significant difference at p<0.05.

23

TABLE 14

| #12 | G T $_m$C c g c a t g c c T A A | SEQ ID NO: 36 |
|---|---|---|
| #12-G3-9 | G T $_m$C c g c a t λ c c T A A | SEQ ID NO: 37 |
| #98 | G A T a t g c c c t a $_m$C T A | SEQ ID NO: 38 |
| #98-G3-6 | G A T a t λ c c c t a $_m$C T A | SEQ ID NO: 39 |
| #14 | G T A t g c c t c c g T T A | SEQ ID NO: 40 |
| #14-G3-5 | G T A t λ c c t c c g T T A | SEQ ID NO: 41 |

As shown in the results of FIG. 14, the serum concentrations of AST and ALT could be reduced significantly only by changing guanine, which is in one of the 2',4'-non-bridged nucleic acid residues in the middle part, to 8-aminoguanine also in other antisense oligonucleic acids #12, #98 and #14 having high hepatotoxicity.

Example 15: Evaluation of Hepatotoxicity of Antisense Oligonucleic Acid

Figure 15:
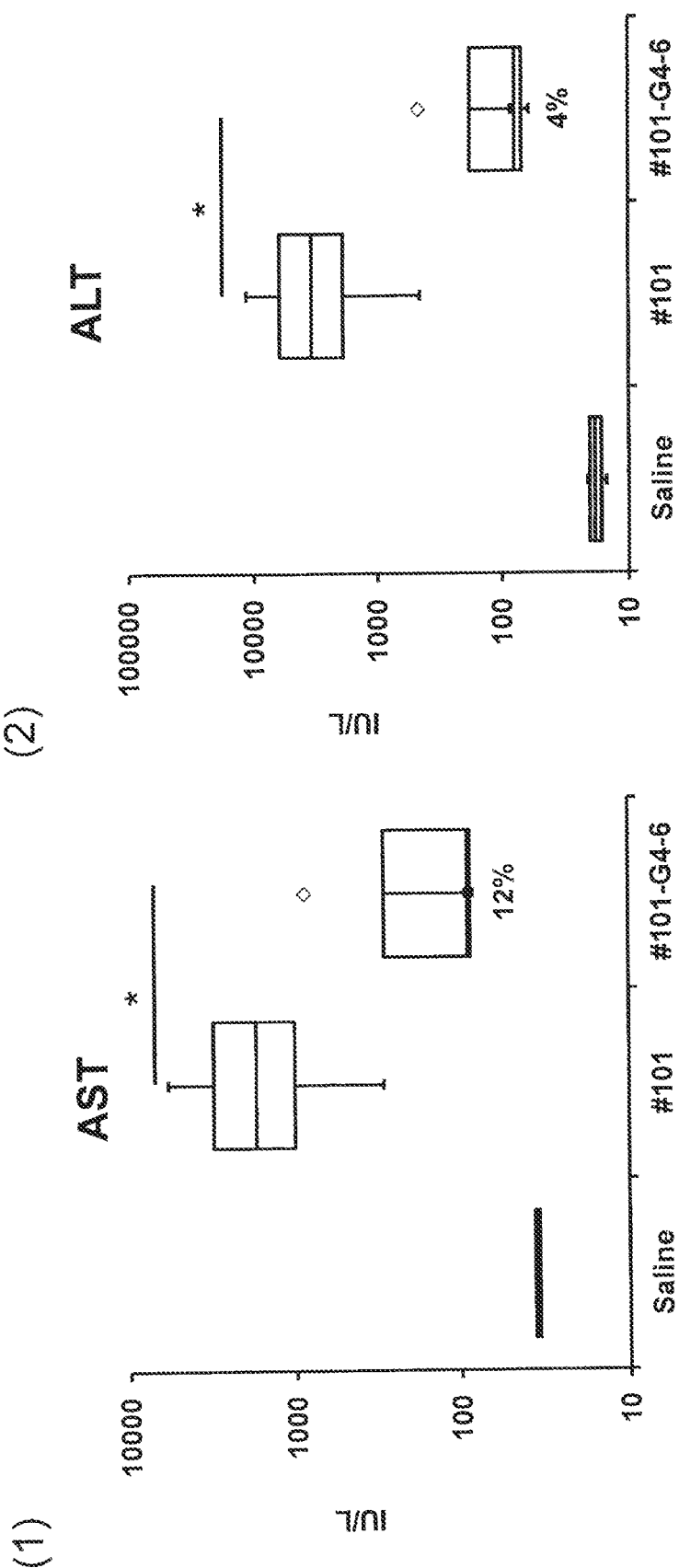
FIG. 15 is a graph showing the results of hepatotoxicity of antisense oligonucleic acid evaluated in the Example described later.

In the same manner as in the above-mentioned Example 1 except that #101 or a derivative thereof #101-G4-6 was used, hepatotoxicity was evaluated. The theoretical value of the molecular weight of #101-G4-6 was 4668.61 and the measured value was 4670.31. The sequence of each antisense oligonucleic acid used in this Example is shown in Table 15, and the measurement results of the hepatotoxicity are shown in FIG. 15. In FIG. 15, "*" indicates presence of a significant difference at p<0.05.

TABLE 15

| #101 | G T T a t g c c a c c $_m$C T A | SEQ ID NO: 42 |
|---|---|---|
| #101-G4-6 | G T T a t μ c c a c c $_m$C T A | SEQ ID NO: 43 |

In the above-mentioned sequences, the base in μ is 8-bromoguanine and μ has the following structure:

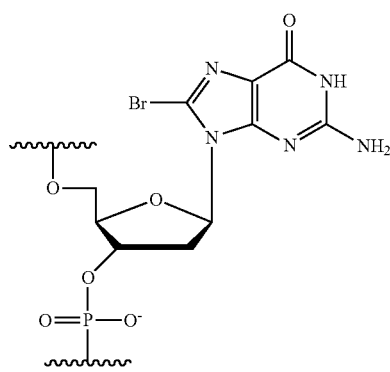

μ

As shown in the results of FIG. 15, the serum concentrations of AST and ALT could be reduced by only converting guanine, which is in one of the 2',4'-non-bridged nucleic acid residues in the middle part of antisense oligonucleic acid #101 having very high hepatotoxicity, to 8-bromoguanine.

Example 16: Evaluation of Hepatotoxicity of Antisense Oligonucleic Acid

Figure 16:
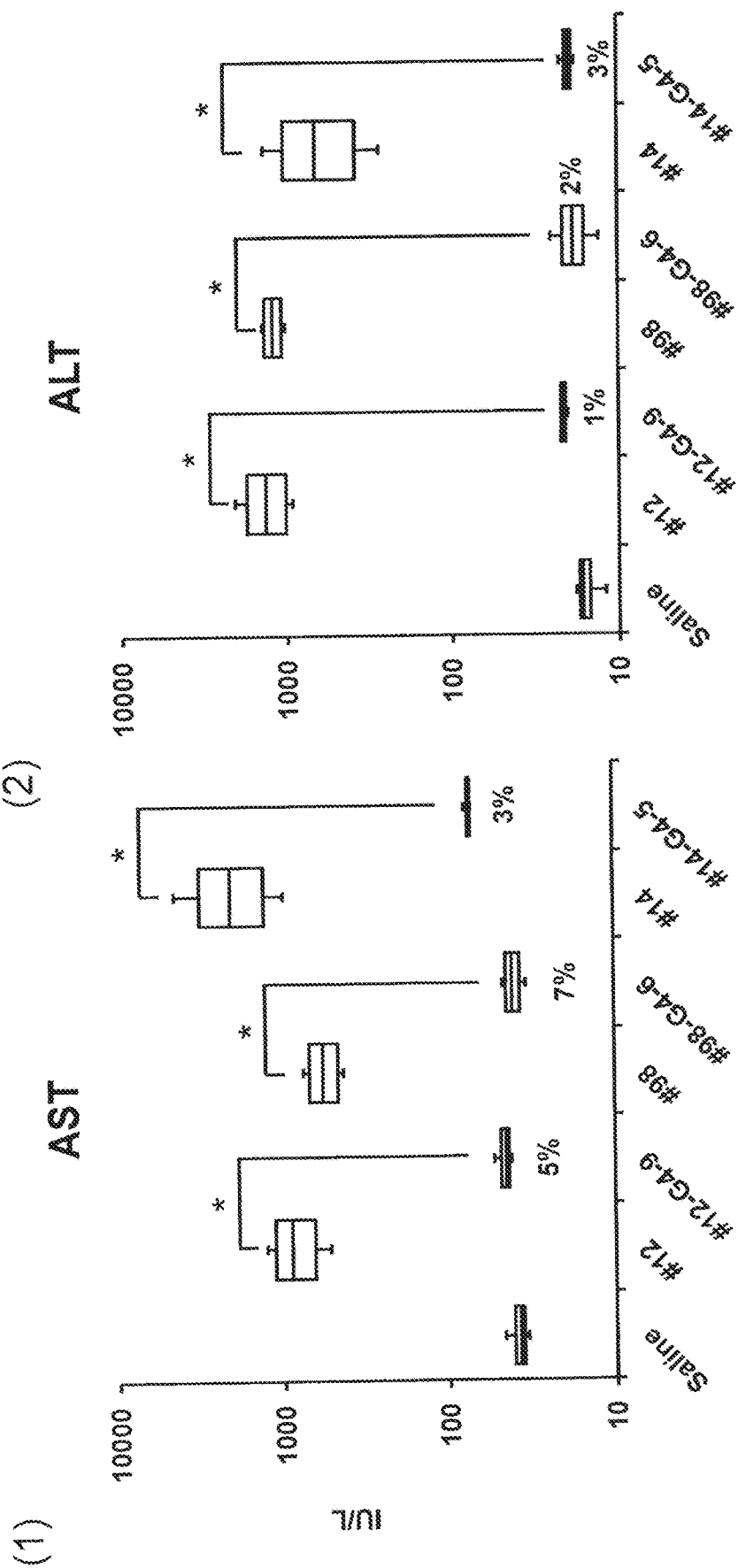
FIG. 16 is a graph showing the results of hepatotoxicity of antisense oligonucleic acid evaluated in the Example described later.

In the same manner as in the above-mentioned Example 1 except that #12, #98, #14 or derivatives thereof were used instead of antisense oligonucleic acid #101, hepatotoxicity was evaluated. The theoretical value of the molecular weight of #12-G4-9 was 4693.62 and the measured value was 4692.50, the theoretical value of the molecular weight of #98-G4-6 was 4692.64 and the measured value was 4693.45, the theoretical value of the molecular weight of #14-G4-5 was 4685.60 and the measured value was 4683.86. The sequence of each antisense oligonucleic acid used in this Example is shown in Table 16, and the measurement results of the hepatotoxicity are shown in FIG. 16. In FIG. 16, "*" indicates presence of a significant difference at p<0.05.

TABLE 16

| #12 | G T $_m$C c g c a t g c c T A A | SEQ ID NO: 44 |
|---|---|---|
| #12-G4-9 | G T $_m$C c g c a t μ c c T A A | SEQ ID NO: 45 |
| #98 | G A T a t g c c c t a $_m$C T A | SEQ ID NO: 46 |
| #98-G4-6 | G A T a t μ c c c t a $_m$C T A | SEQ ID NO: 47 |
| #14 | G T A t g c c t c c g T T A | SEQ ID NO: 48 |
| #14-G4-5 | G T A t μ c c t c c g T T A | SEQ ID NO: 49 |

As shown in the results of FIG. 16, the serum concentrations of AST and ALT could be reduced significantly only by changing guanine, which is in one of the 2',4'-non-bridged nucleic acid residues in the middle part, to 8-bromoguanine also in other antisense oligonucleic acids #12, #98 and #14 having high hepatotoxicity.

Example 17: Evaluation of Hepatotoxicity and Activity of Antisense Oligonucleic Acid Posi14 (Nucleic Acid Ther., 2012, 22, 5, 344-359) was selected as an antisense oligonucleic acid targeting mouse GR, and the synthesis of Posi14 having the sequence shown in Table 17 and its derivative Posi14-G4-10 was committed to Gene Design, Inc. The theoretical value of the molecular weight of Posi14-G4-10 was 4770.67 and the measured value was 4771.46.

TABLE 17

| Posi14 | A G G t g c t t t g g T $_m$C T | SEQ ID NO: 50 |
|---|---|---|
| Posi14-G4-10 | A G G t g c t t t μ g T $_m$C T | SEQ ID NO: 51 |

Figure 17:
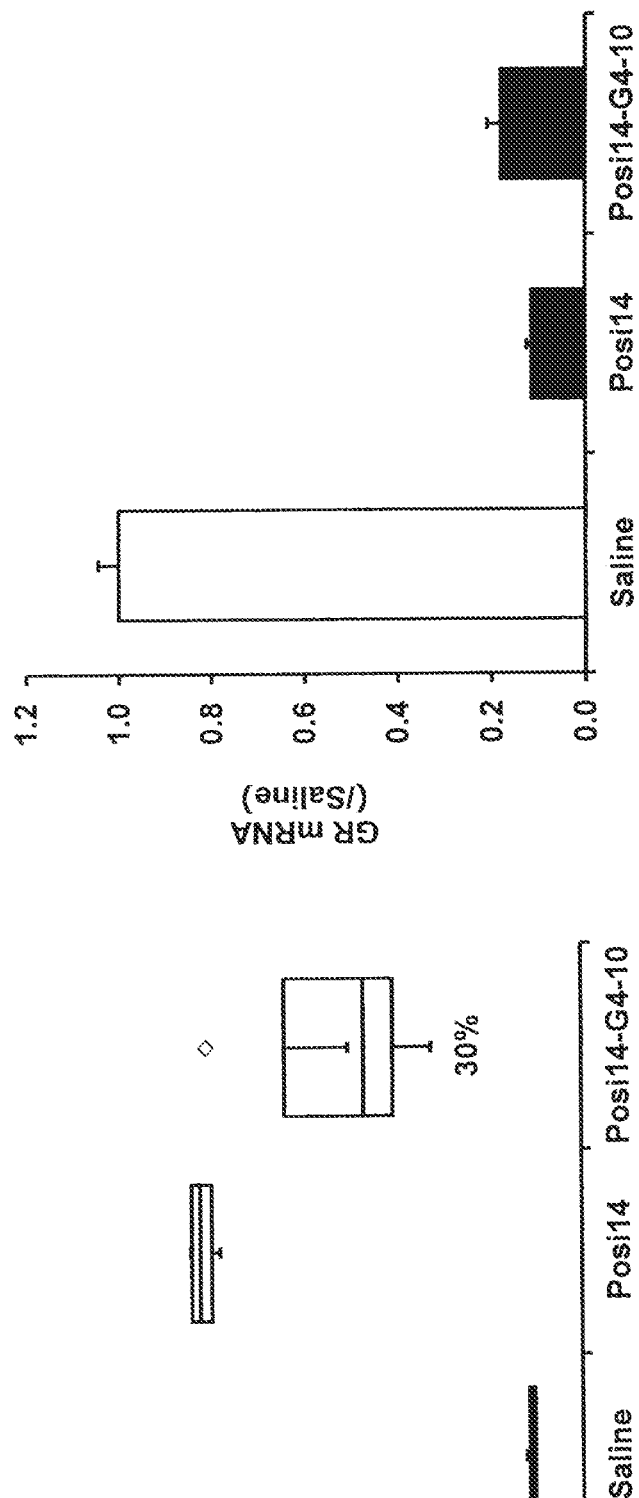
FIG. 17 is a graph showing the results of hepatotoxicity of antisense oligonucleic acid and GR gene expression-suppressing activity evaluated in the Example described later.

With regard to each of the obtained antisense oligonucleic acids, the ALT concentration in mouse serum and GR gene expression-suppressing activity were measured in the same manner as in the above-mentioned Example 3. The results are shown in FIG. 17. In FIG. 17, "*" indicates presence of a significant difference at p<0.05.

As shown in the results of FIG. 17 (1), the hepatotoxicity by Posi14 was reduced to 30% by only changing guanine, which is in one of the 2',4'-non-bridged nucleic acid residues in the middle part, to 8-bromoguanine. On the other hand, as shown in the results of FIG. 17 (2), GR gene expression-suppressing activity almost did not change even when guanine, which is in one of the 2',4'-non-bridged nucleic acid residues in the middle part of Posi14, was changed to 8-bromoguanine. Thus, according to the present invention, hepatotoxicity can be reduced without reducing the activity of antisense oligonucleic acid.

Example 18: Evaluation of Hepatotoxicity and Activity of Antisense Oligonucleic Acid Posi15 was selected as an antisense oligonucleic acid targeting mouse PCSK9, and the synthesis of Posi15 having the sequence shown in Table 18 and its derivative Posi15-G4-8 was committed to Gene Design, Inc. The theoretical value of the molecular weight of Posi15-G4-8 was 4665.66 and the measured value was 4666.01.

TABLE 18

| Posi15    | A $_m$C A c c a a g t t c T $_m$C $_m$C | SEQ ID NO: 52 |
|-----------|-----------------------------------------|---------------|
| Posi15-G4-8 | A $_m$C A c c a a μ t t c T $_m$C $_m$C | SEQ ID NO: 53 |

Figure 18:
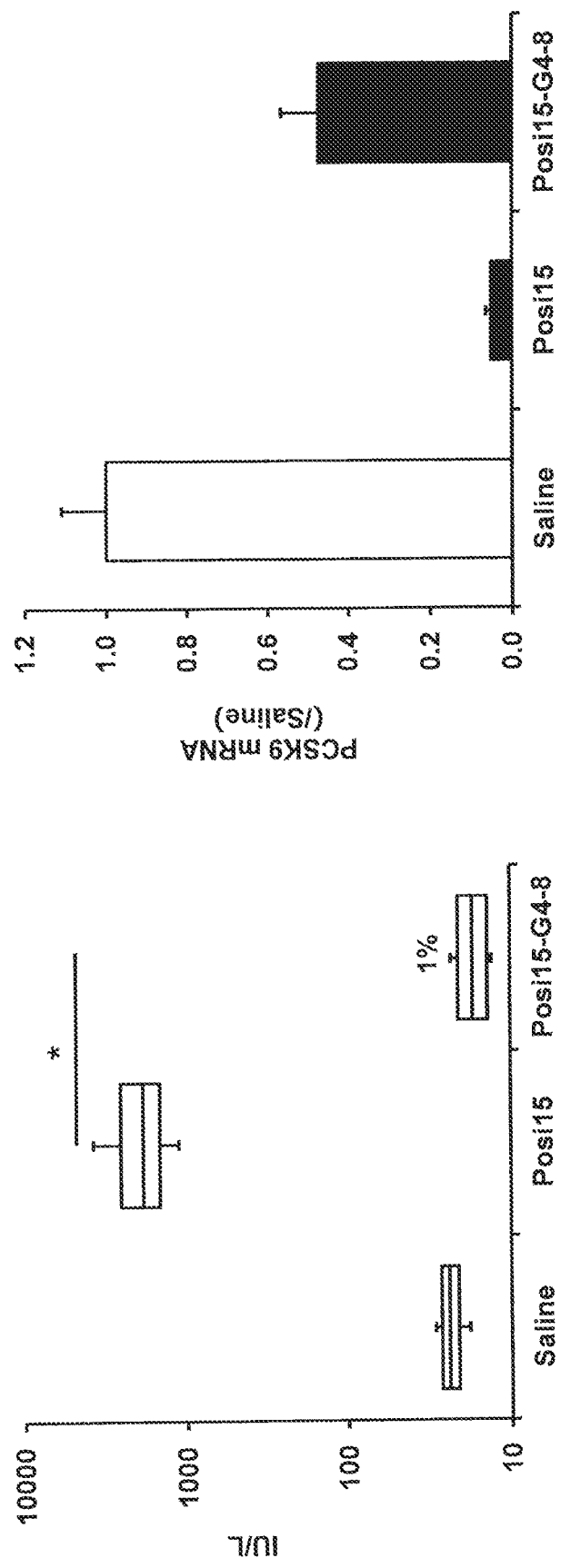
FIG. 18 is a graph showing the results of hepatotoxicity of antisense oligonucleic acid and PCSK9 gene expression-suppressing activity evaluated in the Example described later.

With regard to each of the obtained antisense oligonucleic acids, the ALT concentration in mouse serum and PCSK9 gene expression-suppressing activity were measured in the same manner as in the above-mentioned Example 3. The results are shown in FIG. 18. In FIG. 18, "*" indicates presence of a significant difference at $p<0.05$.

As shown in the results of FIG. 18 (2), PCSK9 gene expression-suppressing activity somewhat decreased when guanine, which is in one of the 2',4'-non-bridged nucleic acid residues in the middle part of Posi15, was changed to 8-bromoguanine. As shown in the results of FIG. 18 (1), hepatotoxicity due to Posi15 was significantly reduced to 1%. Thus, according to the present invention, hepatotoxicity can be reduced without reducing the activity of antisense oligonucleic acid too much.

Example 19: Evaluation of Hepatotoxicity and Activity of Antisense Oligonucleic Acid Posi17 was selected as an antisense oligonucleic acid targeting mouse PCSK9, and the synthesis of Posi17 having the sequence shown in Table 19 and its derivatives Posi17-G4-3, Posi17-G4-5 and Posi17-G4-8 was committed to Gene Design, Inc. The theoretical value of the molecular weight of Posi17-G4-3 was 4379.43 and the measured value was 4378.54, the theoretical value of the molecular weight of Posi17-G4-5 was 4379.43 and the measured value was 4377.25, and the theoretical value of the molecular weight of Posi17-G4-8 was 4379.43 and the measured value was 4378.34.

TABLE 19

| Posi17      | $_m$C T g t g a t g a c $_m$C T $_m$C | SEQ ID NO: 54 |
|-------------|---------------------------------------|---------------|
| Posi17-G4-3 | $_m$C T μ t g a t g a c $_m$C T $_m$C | SEQ ID NO: 55 |
| Posi17-G4-5 | $_m$C T g t μ a t g a c $_m$C T $_m$C | SEQ ID NO: 56 |
| Posi17-G4-8 | $_m$C T g t g a t μ a c $_m$C T $_m$C | SEQ ID NO: 57 |

Figure 19:
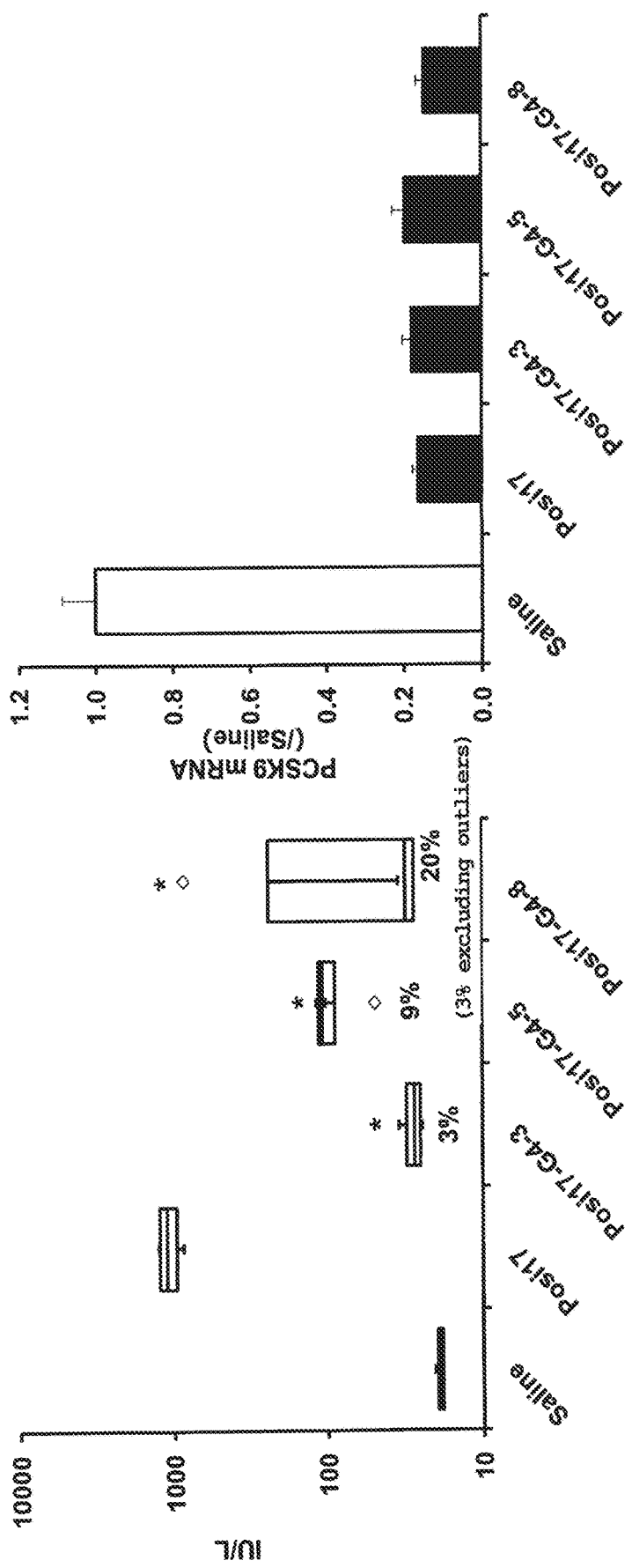
FIG. 19 is a graph showing the results of hepatotoxicity of antisense oligonucleic acid and PCSK9 gene expression-suppressing activity evaluated in the Example described later.

With regard to each of the obtained antisense oligonucleic acids, the ALT concentration in mouse serum and PCSK9 gene expression-suppressing activity were measured in the same manner as in the above-mentioned Example 3. The results are shown in FIG. 19. In FIG. 19, "*" indicates presence of a significant difference at $p<0.05$.

As shown in the results of FIG. 19 (1), the hepatotoxicity by Posi17 was significantly reduced to 3%, 9% or 20% by only changing guanine, which is in one of the 2',4'-non-bridged nucleic acid residues in the middle part, to 8-bromoguanine. The hepatotoxicity reducing effect of Posi17-G4-8 showed reduction to 3% when abnormal measurement values were removed. On the other hand, as shown in the results of FIG. 19 (2), PCSK9 gene expression-suppressing activity almost did not change even when guanine, which is in one of the 2',4'-non-bridged nucleic acid residues in the middle part of Posi17, was changed to 8-bromoguanine. Thus, according to the present invention, hepatotoxicity can be reduced without reducing the activity of antisense oligonucleic acid.

Example 20: Evaluation of Hepatotoxicity and Activity of Antisense Oligonucleic Acid No. 97 was selected as an antisense oligonucleic acid targeting mouse Rps6kb2, and the synthesis of No. 97 having the sequence shown in Table 20 and its derivative No. 97-G4-8 was committed to Gene Design, Inc. The theoretical value of the molecular weight of No. 97-G4-8 was 4261.29 and the measured value was 4261.11.

TABLE 20

| No. 97      | $_m$C G c c c t c g c c $_m$C T $_m$C | SEQ ID NO: 58 |
|-------------|---------------------------------------|---------------|
| No. 97-G4-8 | $_m$C G c c c t c μ c c $_m$C T $_m$C | SEQ ID NO: 59 |

Figure 20:
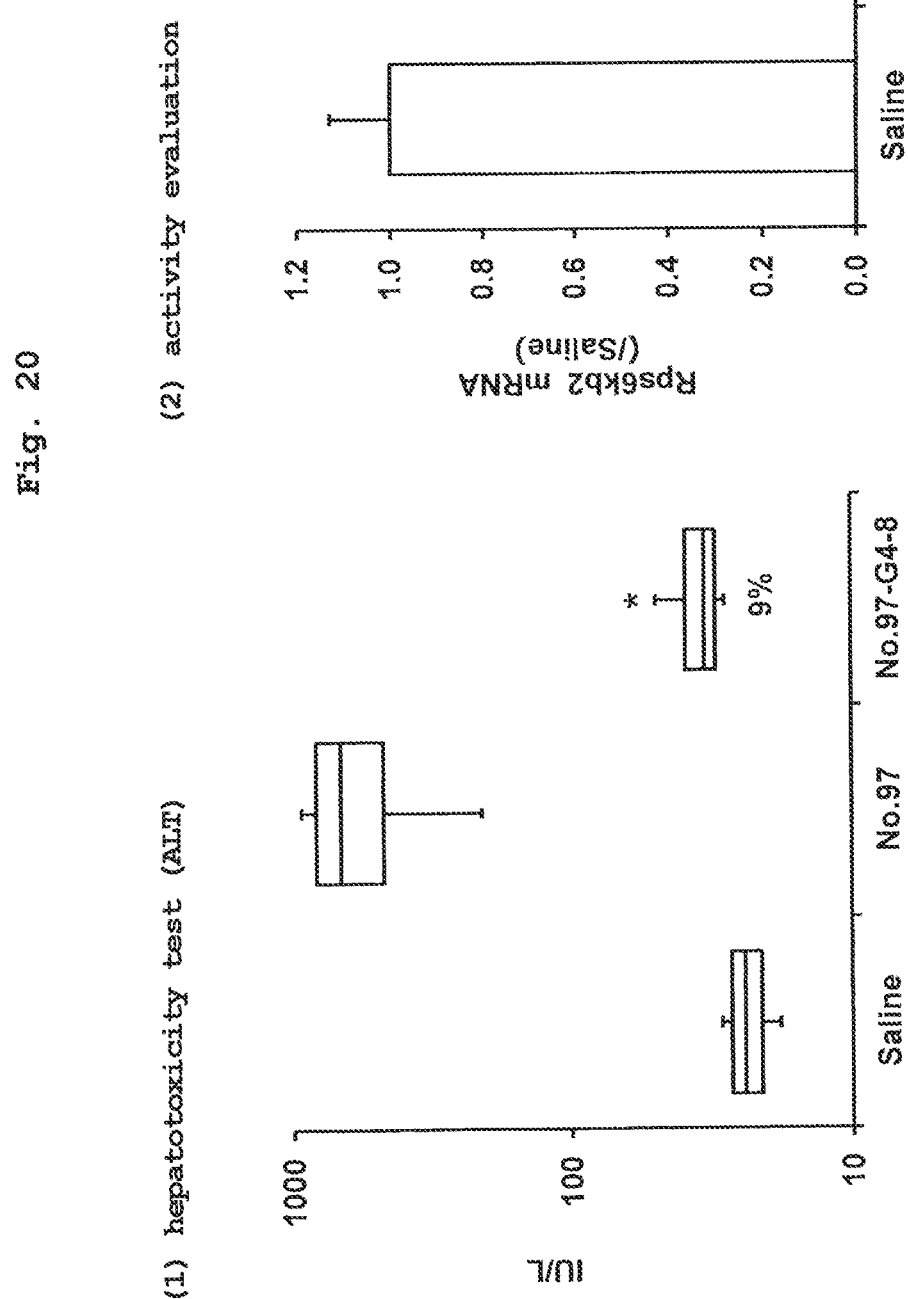
FIG. 20 is a graph showing the results of hepatotoxicity of antisense oligonucleic acid and Rps6kb2 gene expression-suppressing activity evaluated in the Example described later.

With regard to each of the obtained antisense oligonucleic acids, the ALT concentration in mouse serum and Rps6kb2 gene expression-suppressing activity were measured in the same manner as in the above-mentioned Example 3. The results are shown in FIG. 20. In FIG. 20, "*" indicates presence of a significant difference at $p<0.05$.

As shown in the results of FIG. 20 (1), the hepatotoxicity by No. 97 was significantly reduced to 9% by only changing guanine, which is in one of the 2',4'-non-bridged nucleic acid residues in the middle part, to 8-bromoguanine. On the other hand, as shown in the results of FIG. 20 (2), Rps6kb2 gene expression-suppressing activity almost did not change even when guanine, which is in one of the 2',4'-non-bridged nucleic acid residues in the middle part of No. 97, was changed to 8-bromoguanine. Thus, according to the present invention, hepatotoxicity can be reduced without reducing the activity of antisense oligonucleic acid.

Figure 21:
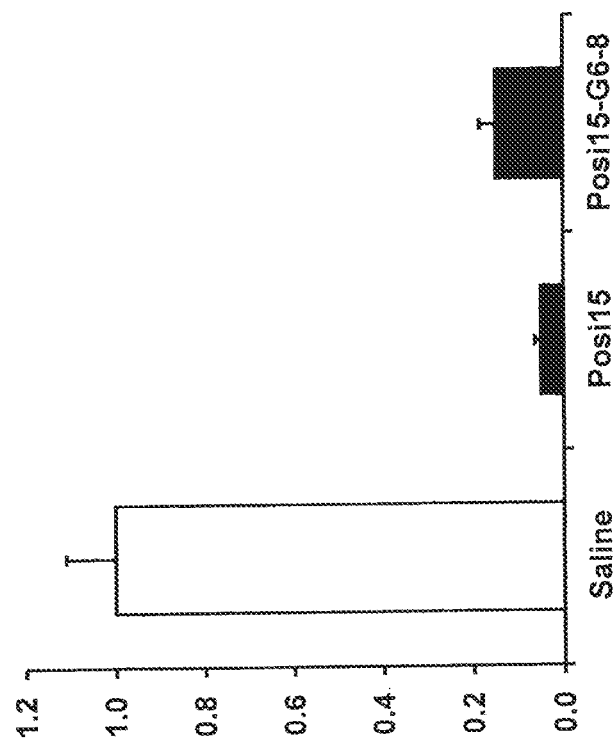
FIG. 21 is a graph showing the results of hepatotoxicity of antisense oligonucleic acid and PCSK9 gene expression-suppressing activity evaluated in the Example described later.
Figure 21:
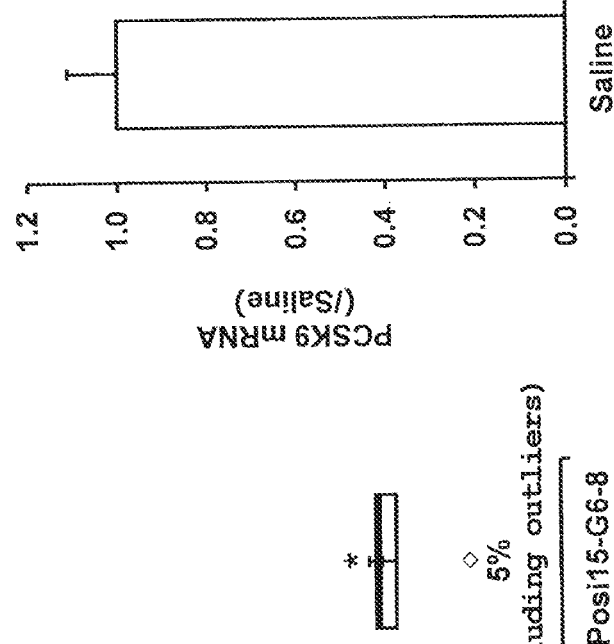
Figure 21:
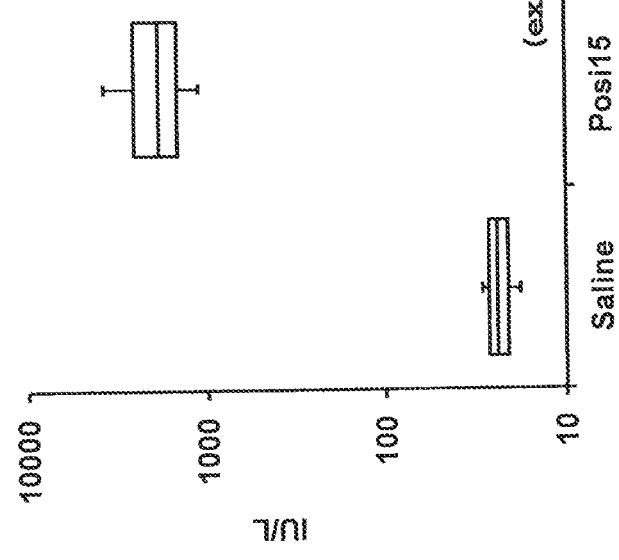
Figure 22:
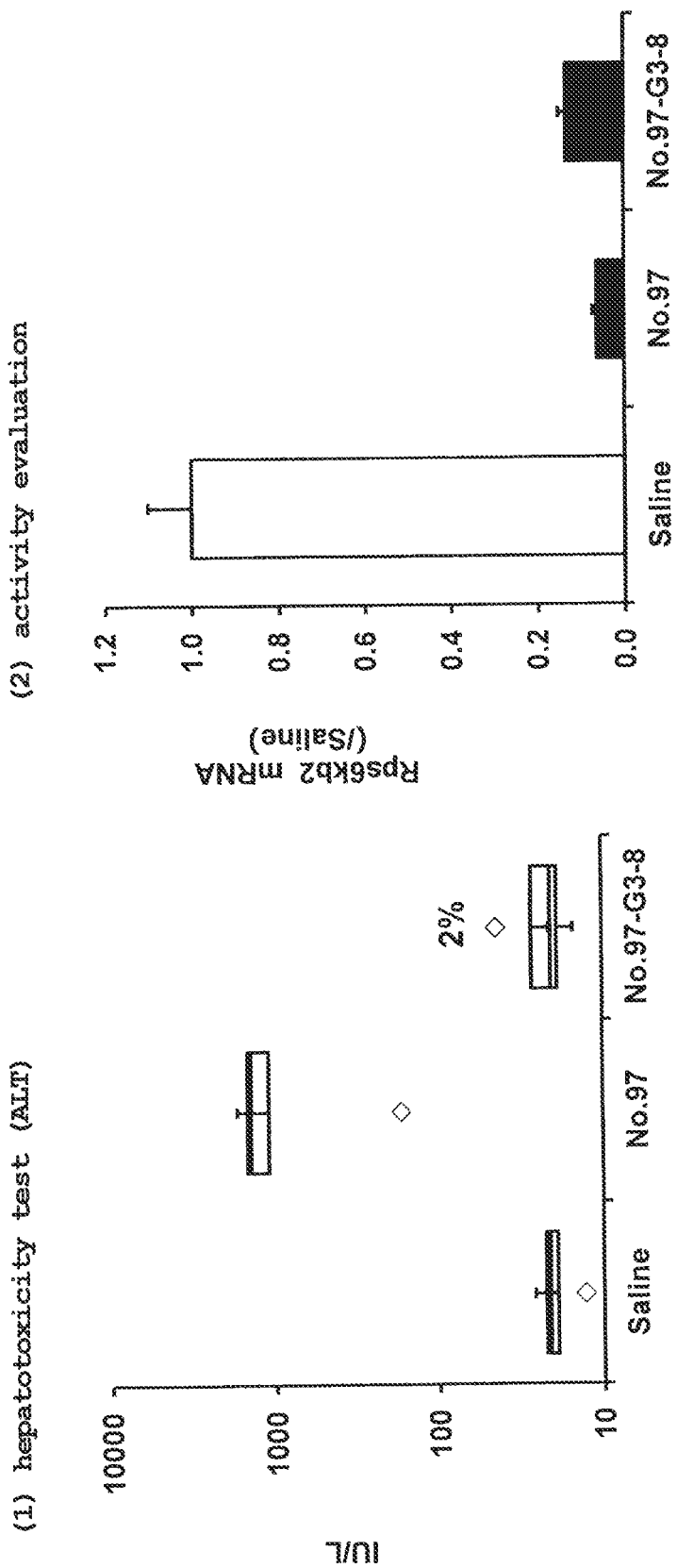
FIG. 22 is a graph showing the results of hepatotoxicity of antisense oligonucleic acid and Rps6kb2 gene expression-suppressing activity evaluated in the Example described later.
Figure 23:
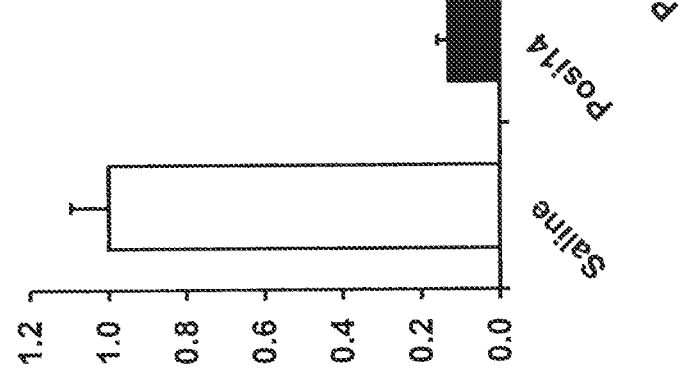
FIG. 23 is a graph showing the results of hepatotoxicity of antisense oligonucleic acid and GR gene expression-suppressing activity evaluated in the Example described later.
Figure 23:
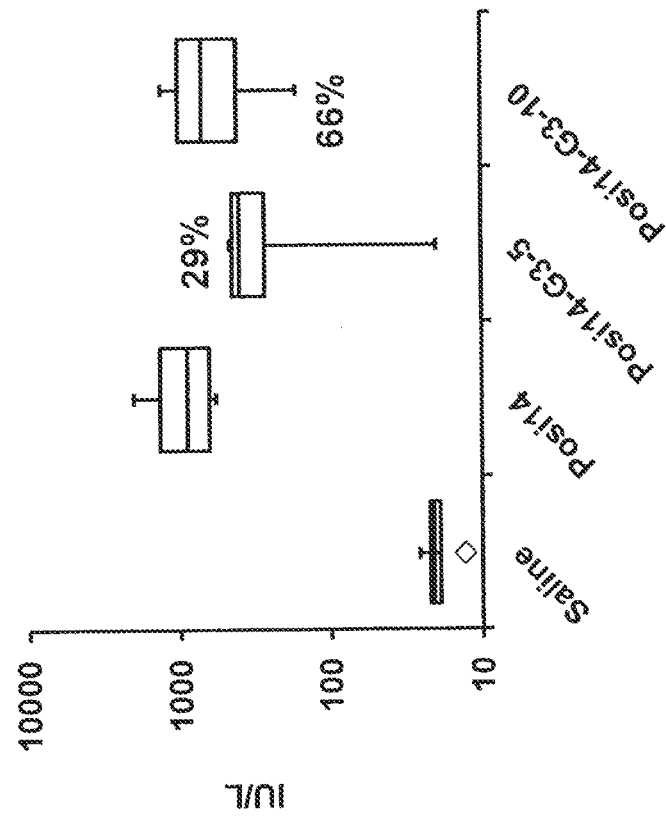
Figure 24:
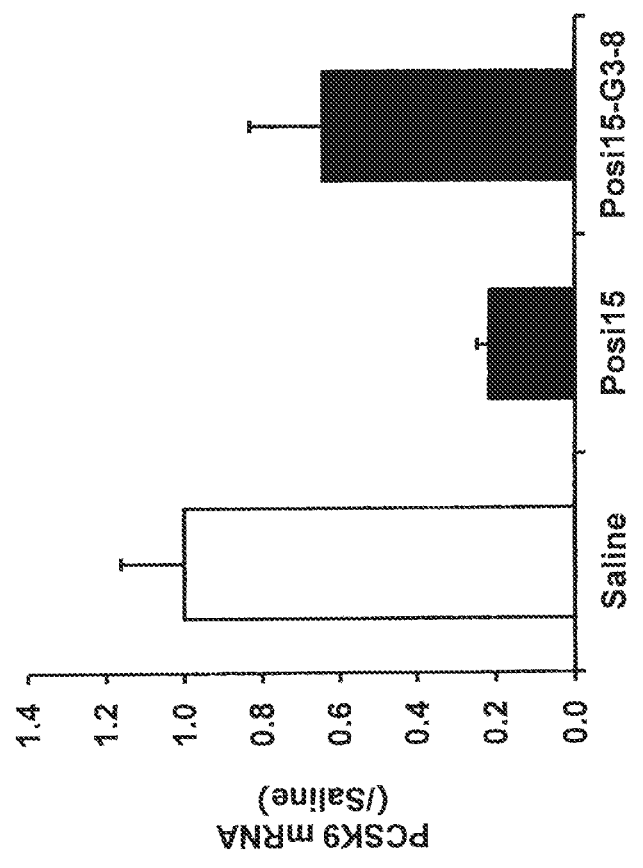
FIG. 24 is a graph showing the results of hepatotoxicity of antisense oligonucleic acid and PCSK9 gene expression-suppressing activity evaluated in the Example described later.
Figure 24:
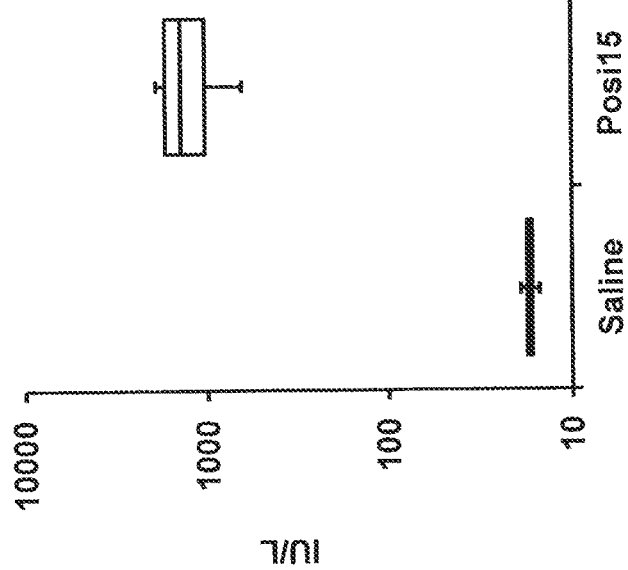
Figure 25:
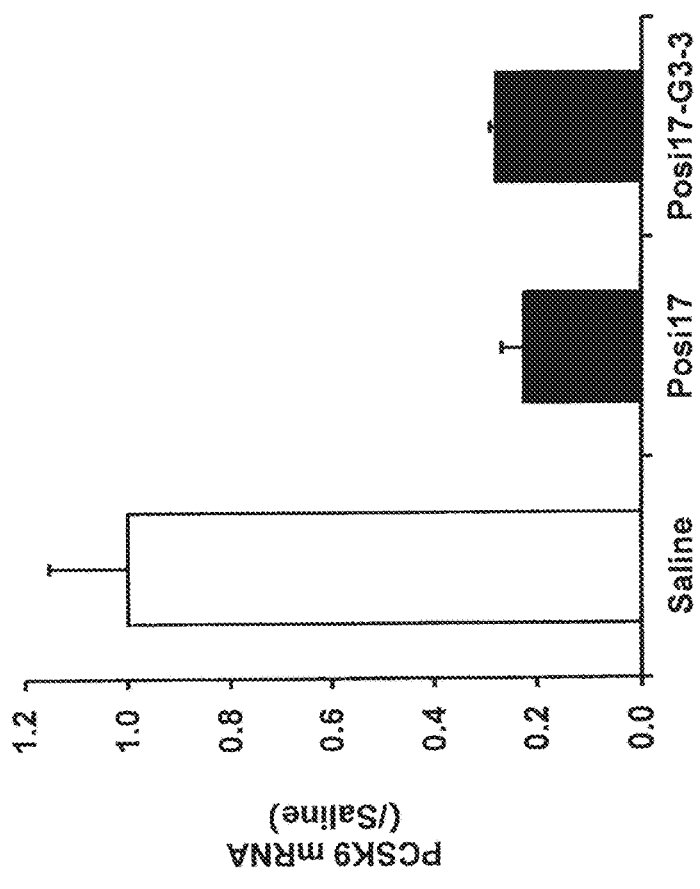
FIG. 25 is a graph showing the results of hepatotoxicity of antisense oligonucleic acid and PCSK9 gene expression-suppressing activity evaluated in the Example described later.
Figure 25:
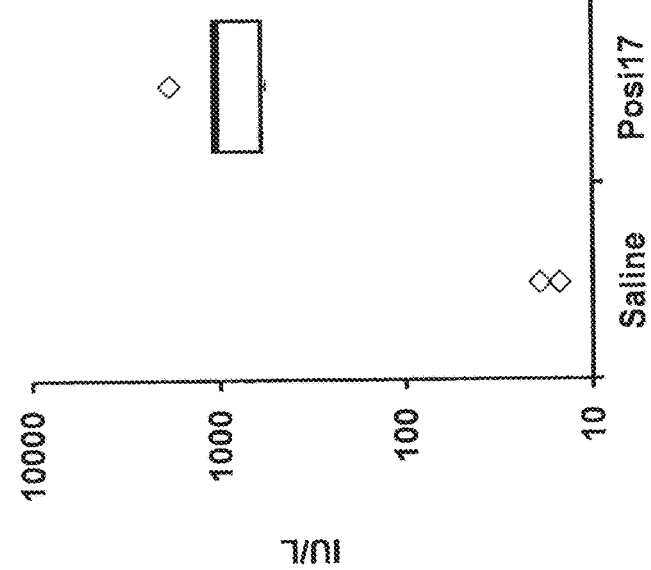

Example 21: Evaluation of Hepatotoxicity and Activity of Antisense Oligonucleic Acid In the same manner as in the above-mentioned Example 5 except that Posi15 derivative, Posi15-G6-8, was used, hepatotoxicity and activity were evaluated. The theoretical value of the molecular weight of Posi15-G6-8 was 4685.90 and the measured value was 4683.03. The sequence of each antisense oligonucleic acid used in this Example is shown in Table 21, and the measurement results of the hepatotoxicity are shown in FIG. 21. In FIG. 21, "*" indicates presence of a significant difference at $p<0.05$.

TABLE 21

| Posi15 | A $_m$C A c c a a g t t c T $_m$C $_m$C | SEQ ID NO: 60 |
|---|---|---|
| Posi15-G6-8 | A $_m$C A c c a a α t t c T $_m$C $_m$C | SEQ ID NO: 61 |

In the above-mentioned sequences, the base in a is 7-phenylethynylguanine and a has the following structure:

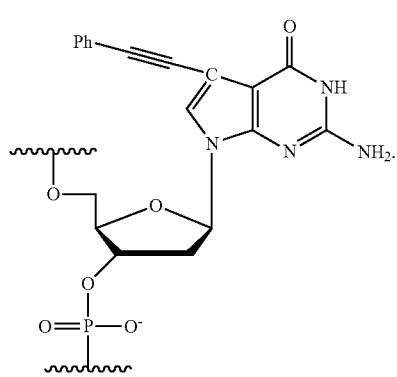

As shown in the results of FIG. 21 (1), the hepatotoxicity by Posi15 was significantly reduced to 5% by only changing guanine, which is in one of the 2',4'-non-bridged nucleic acid residues in the middle part, to 7-phenylethynylguanine and removing abnormal measurement values. On the other hand, as shown in the results of FIG. 21 (2), PCSK9 gene expression-suppressing activity almost did not change even when guanine, which is in one of the 2',4'-non-bridged nucleic acid residues in the middle part of Posi15, was changed to 7-phenylethynylguanine. Thus, according to the present invention, hepatotoxicity can be reduced without reducing the activity of antisense oligonucleic acid.

Example 22: Evaluation of Hepatotoxicity and Activity of Antisense Oligonucleic Acid No. 97 and Posi14 were respectively selected as antisense oligonucleic acids targeting mouse Rps6kb2 and mouse GR, and the synthesis of No. 97, Posi14 having the sequences shown in Table 22 and derivatives in which guanine, which is in one of the 2',4'-non-bridged nucleic acid residues in the middle part, was changed to 8-aminoguanine was committed to Gene Design, Inc. In addition, Posi15 and Posi17 were respectively selected as antisense oligonucleic acids targeting mouse PCSK9 gene and the synthesis of Posi15, Posi17 having the sequences shown in Table 22 and derivatives in which guanine, which is in one of the 2',4'-non-bridged nucleic acid residues in the middle part, was changed to 8-aminoguanine was committed to Gene Design, Inc.

TABLE 22

| No. 97 | $_m$C G c c c t c g c c $_m$C T $_m$C | SEQ ID NO: 62 |
|---|---|---|
| No. 97-G3-8 | $_m$C G c c c t c λ c c $_m$C T $_m$C | SEQ ID NO: 63 |
| Posi14 | A G G t g c t t t g g T $_m$C T | SEQ ID NO: 64 |

TABLE 22-continued

| Posi14-G3-5 | A G G t λ c t t t g g T $_m$C T | SEQ ID NO: 65 |
|---|---|---|
| Posi14-G3-10 | A G G t g c t t t λ g T $_m$C T | SEQ ID NO: 66 |
| Posi15 | A $_m$C A c c a a g t t c T $_m$C $_m$C | SEQ ID NO: 67 |
| Posi15-G3-8 | A $_m$C A c c a a λ t t c T $_m$C $_m$C | SEQ ID NO: 68 |
| Posi17 | $_m$C T g t g a t g a c $_m$C T $_m$C | SEQ ID NO: 69 |
| Posi17-G3-3 | $_m$C T λ t g a t g a c $_m$C T $_m$C | SEQ ID NO: 70 |

With regard to each of the obtained antisense oligonucleic acids, the ALT concentration in mouse serum and mouse Rps6kb2 gene, mouse GR gene or mouse PCSK9 gene expression-suppressing activity were measured in the same manner as in the above-mentioned Example 3. The results are shown in FIGS. 22-25.

As shown in the results of FIGS. 22-25 (1), the hepatotoxicity by No. 97, Posi14, Posi15 and Posi17 was clearly reduced by only changing guanine, which is in one of the 2',4'-non-bridged nucleic acid residues in the middle part, to 8-aminoguanine. On the other hand, as shown in the results of FIGS. 22-25 (2), mouse Rps6kb2 gene expression-, mouse GR gene expression- and mouse PCSK9 gene expression-suppressing activities almost did not change except a part thereof even when guanine, which is in one of the 2',4'-non-bridged nucleic acid residues in the middle part of No. 97, Posi14, Posi15 and Posi17, was changed to 8-aminoguanine. Thus, according to the present invention, hepatotoxicity can be reduced without reducing the activity of antisense oligonucleic acid.

Example 23: Evaluation of Hepatotoxicity of Antisense Oligonucleic Acid

12 was selected as an antisense oligonucleic acid that induces strong hepatotoxicity, and the synthesis of #12 having the sequence shown in Table 23 and a derivative in which guanine, which is in one of the 2',4'-non-bridged nucleic acid residues in the middle part, was changed to 7-substituted guanine having the following structure was committed to Gene Design, Inc. The compound used for introduction of the 7-substituted guanosine derivative is novel and the synthesis method thereof is described later.

TABLE 23

| #12 | G T $_m$C c g c a t g c c T A A | SEQ ID NO: 71 |
|---|---|---|
| #12-G6-9 | G T $_m$C c g c a t α c c T A A | SEQ ID NO: 72 |
| #12-G7-9 | G T $_m$C c g c a t β c c T A A | SEQ ID NO: 73 |
| #12-G8-9 | G T $_m$C c g c a t γ c c T A A | SEQ ID NO: 74 |
| #12-G9-9 | G T $_m$C c g c a t δ c c T A A | SEQ ID NO: 75 |

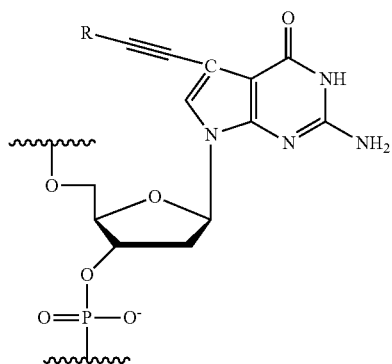

α: R = Ph
β: R = 4-pyridyl
γ: R = HOCH₂

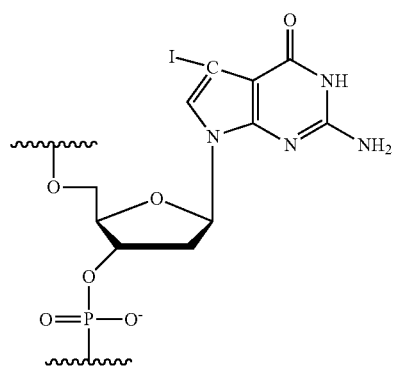

δ

Figure 26:
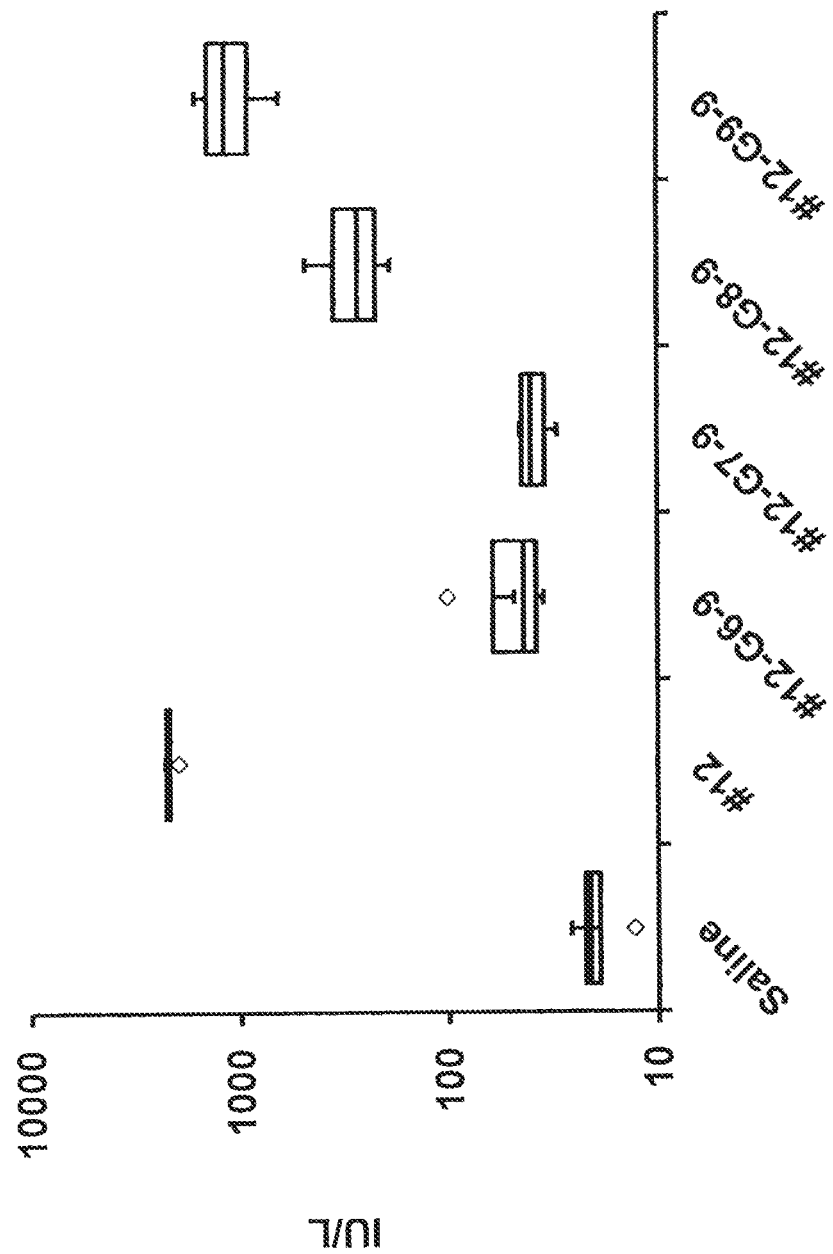
FIG. 26 is a graph showing the results of hepatotoxicity of antisense oligonucleic acid evaluated in the Example described later.

With regard to each of the obtained antisense oligonucleic acids, the ALT concentration in mouse serum was measured in the same manner as in the above-mentioned Example 3. The results are shown in FIG. 26. As shown in the results of FIG. 26, hepatotoxicity by #12 was effectively decreased by only introducing a substituent into the 7-position of guanine, which is in one of the 2′,4′-non-bridged nucleic acid residues in the middle part.

Example 24: Evaluation of Hepatotoxicity and Activity of Antisense Oligonucleic Acid Posi14 and Posi15 were respectively selected as an antisense oligonucleic acid targeting mouse GR and mouse PCSK9 gene, and the synthesis of Posi14, Posi15 having the sequences shown in Table 24 and a derivative in which guanine, which is in one of the 2′,4′-non-bridged nucleic acid residues in the middle part, was changed to 7-substituted guanine was committed to Gene Design, Inc.

TABLE 24

| | | |
|---|---|---|
| Posi14 | A G G t g c t t t g g T ₘC T | SEQ ID NO: 76 |
| Posi14-G7-5 | A G G t β c t t t g g T ₘC T | SEQ ID NO: 77 |
| Posi14-G9-5 | A G G t δ c t t t g g T ₘC T | SEQ ID NO: 78 |
| Posi14-G9-10 | A G G t g c t t t δ g T ₘC T | SEQ ID NO: 79 |
| Posi15 | A ₘC A c c a a g t t c T ₘC ₘC | SEQ ID NO: 80 |

TABLE 24-continued

| | | |
|---|---|---|
| Posi15-G7-8 | A ₘC A c c a a β t t c T ₘC ₘC | SEQ ID NO: 81 |
| Posi15-G9-8 | A ₘC A c c a a δ t t c T ₘC ₘC | SEQ ID NO: 82 |

With regard to each of the obtained antisense oligonucleic acids, the ALT concentration in mouse serum and mouse GR gene or mouse PCSK9 gene expression-suppressing activity were measured in the same manner as in the above-mentioned Example 3. The results are shown in FIGS. 27, 28.

Figure 27:
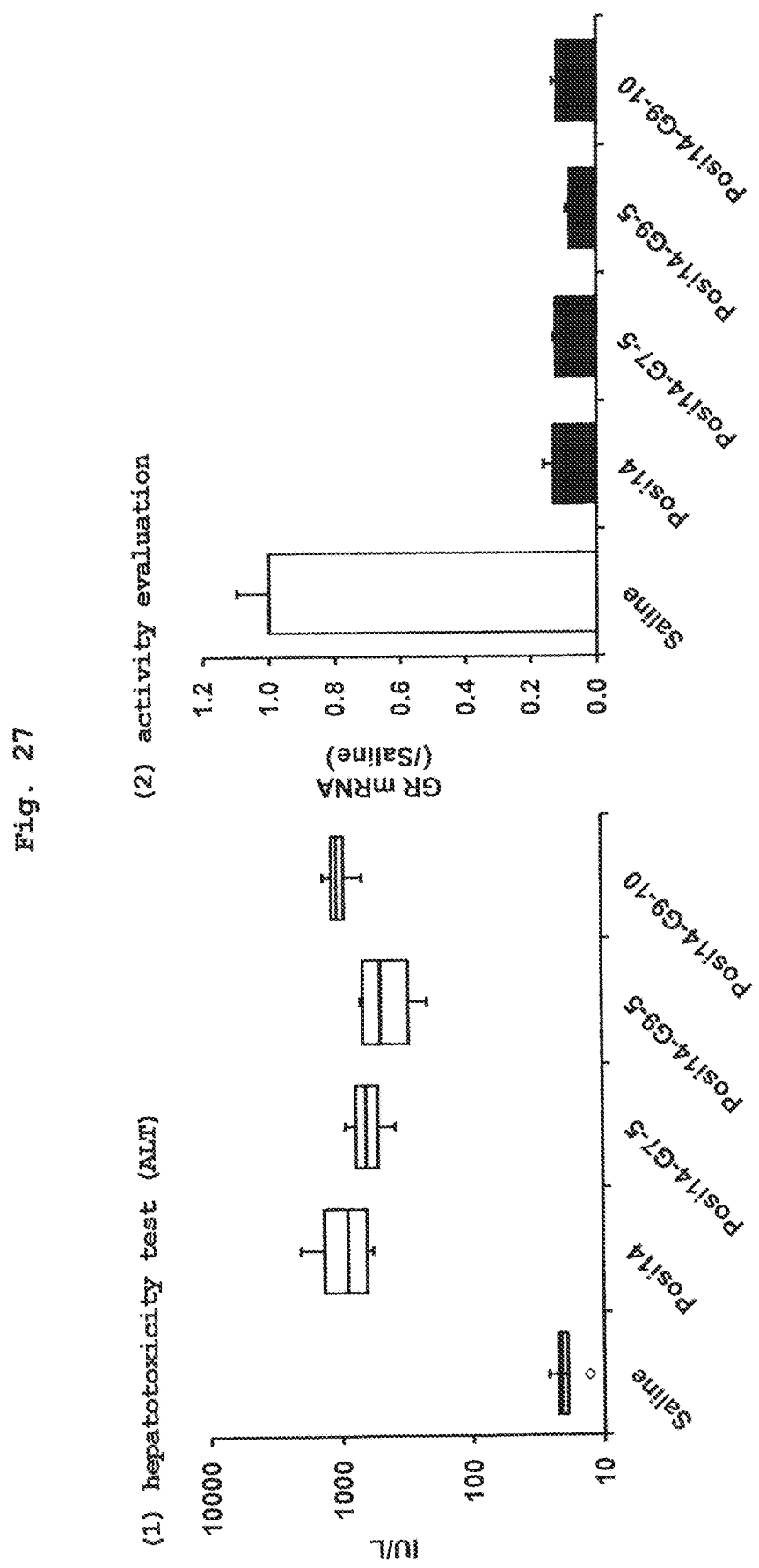
FIG. 27 is a graph showing the results of hepatotoxicity of antisense oligonucleic acid and GR gene expression-suppressing activity evaluated in the Example described later.
Figure 28:
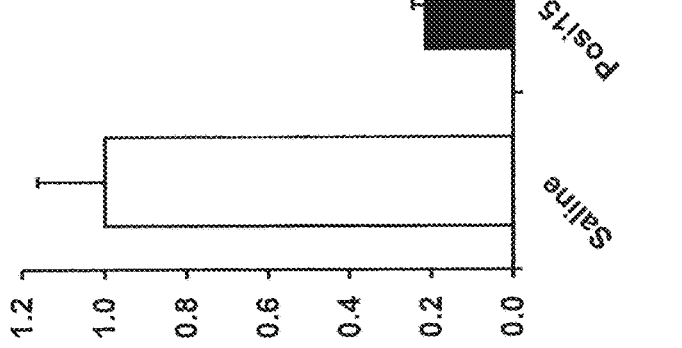
FIG. 28 is a graph showing the results of hepatotoxicity of antisense oligonucleic acid and PCSK9 gene expression-suppressing activity evaluated in the Example described later.
Figure 28:
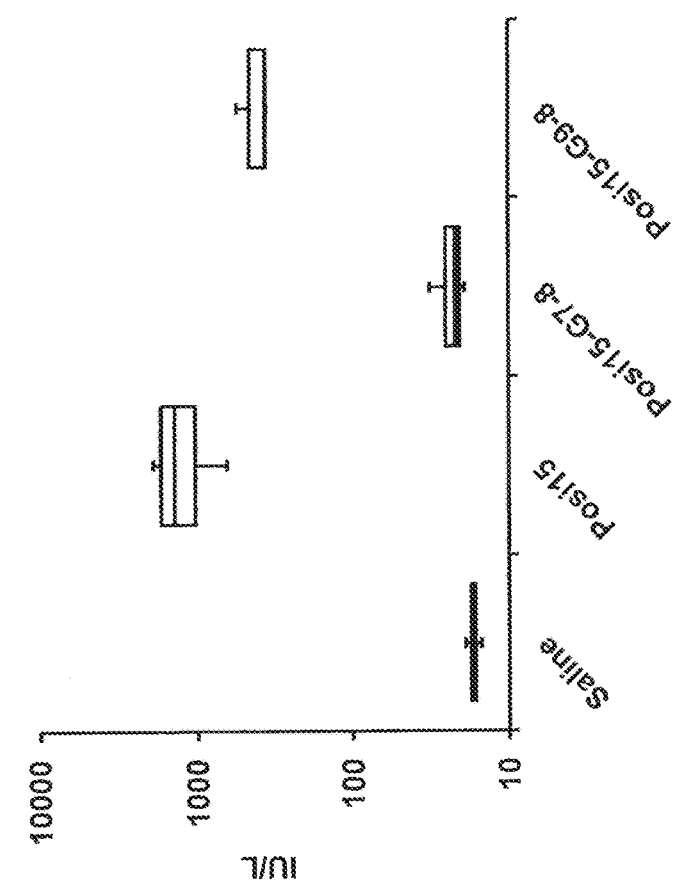

As shown in the results of FIG. 27, 28 (1), hepatotoxicity by Posi14 and Posi15 was clearly reduced by only changing guanine, which is in one of the 2′,4′-non-bridged nucleic acid residues in the middle part, to 7-substituted guanine. On the other hand, as shown in the results of FIGS. 27, 28 (2), mouse GR gene expression- and mouse PCSK9 gene expression-suppressing activities almost did not change even when guanine, which is in one of the 2′,4′-non-bridged nucleic acid residues in the middle part of Posi14 and Posi15, was changed to 7-substituted guanine. Thus, according to the present invention, hepatotoxicity can be reduced without reducing the activity of antisense oligonucleic acid.

Example 25: Evaluation of Hepatotoxicity of Antisense Oligonucleic Acid

101 was selected as an antisense oligonucleic acid that induces strong hepatotoxicity, and the synthesis of #101 having the sequence shown in Table 25 and a derivative in which cytosine, which is in one of the 2′,4′-non-bridged nucleic acid residues in the middle part, was changed to 5-hydroxycytosine was committed to Gene Design, Inc.

TABLE 25

| | | |
|---|---|---|
| #101 | G T T a t g c c a c c ₘC T A | SEQ ID NO: 83 |
| #101-C2-7 | G T T a t g ζ c a c c ₘC T A | SEQ ID NO: 84 |
| #101-C2-8 | G T T a t g c ζ a c c ₘC T A | SEQ ID NO: 85 |
| #101-C2-10 | G T T a t g c c a ζ c ₘC T A | SEQ ID NO: 86 |
| #101-C2-11 | G T T a t g c c a c ζ ₘC T A | SEQ ID NO: 87 |

Figure 29:
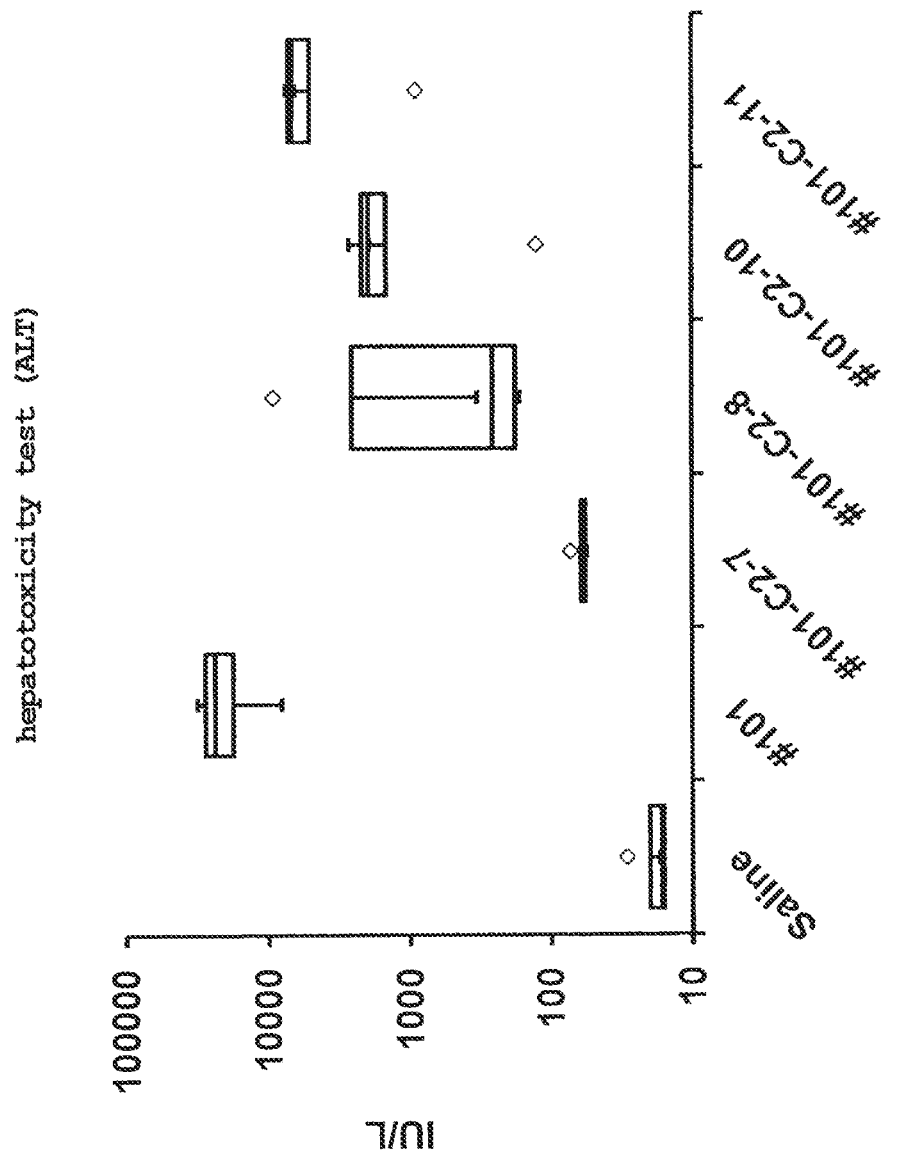
FIG. 29 is a graph showing the results of hepatotoxicity of antisense oligonucleic acid evaluated in the Example described later.

With regard to each of the obtained antisense oligonucleic acids, the ALT concentration in mouse serum was measured in the same manner as in the above-mentioned Example 3. The results are shown in FIG. 29. As shown in the results of FIG. 29, hepatotoxicity by #101 was effectively decreased by only changing cytosine, which is in one of the 2′,4′-non-bridged nucleic acid residues in the middle part, to 5-hydroxycytosine.

Example 26: Evaluation of Hepatotoxicity of Antisense Oligonucleic Acid

101 was selected as an antisense oligonucleic acid that induces strong hepatotoxicity, and the synthesis of #101 having the sequence shown in Table 26 and a derivative in which 1 to 3 bases in the 2′,4′-non-bridged nucleic acid residues in the middle part was (were) changed to 5-hydroxycytosine (ζ), 2-thiocarbonylthymine (κ) or 8-bromoguanine (μ) was committed to Gene Design, Inc.

TABLE 26

| #101 | G T T a t g c c a c c $_m$C T A | SEQ ID NO: 88 |
|---|---|---|
| #101-C2-7 | G T T a t g ζ c a c c $_m$C T A | SEQ ID NO: 89 |
| #101-T6-5 | G T T a κ g c c a c c $_m$C T A | SEQ ID NO: 90 |
| #101-G4-6 | G T T a t μ c c a c c $_m$C T A | SEQ ID NO: 91 |
| #101-T6C2 | G T T a κ g ζ c a c c $_m$C T A | SEQ ID NO: 92 |
| #101-T6G4 | G T T a κ μ c c a c c $_m$C T A | SEQ ID NO: 93 |
| #101-G4C2 | G T T a t μ ζ c a c c $_m$C T A | SEQ ID NO: 94 |
| #101-T6G4C2 | G T T a κ μ ζ c a c c $_m$C T A | SEQ ID NO: 95 |

Figure 30:
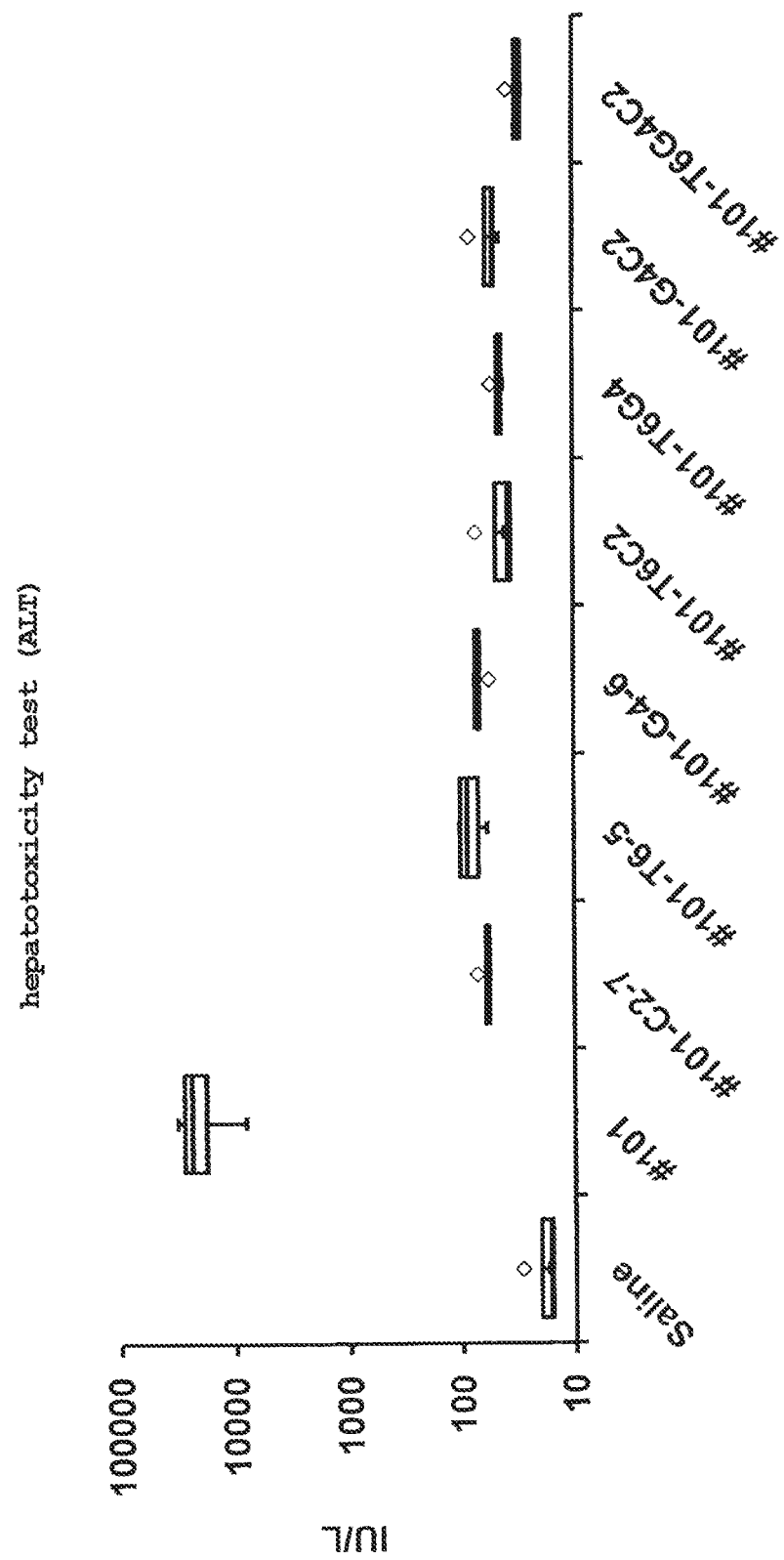
FIG. 30 is a graph showing the results of hepatotoxicity of antisense oligonucleic acid evaluated in the Example described later.

With regard to each of the obtained antisense oligonucleic acids, the ALT concentration in mouse serum was measured in the same manner as in the above-mentioned Example 3. The results are shown in FIG. 30. As shown in the results of FIG. 30, it was demonstrated that hepatotoxicity by #101 was effectively decreased by only changing one base in the 2',4'-non-bridged nucleic acid residues in the middle part to a derivative, and the hepatotoxicity attenuation effect is increased still more by changing two or more bases in the 2',4'-non-bridged nucleic acid residues in the middle part, to the derivative(s).

Example 27: Synthesis of 7-deaza-7-iodoguanosine Derivative

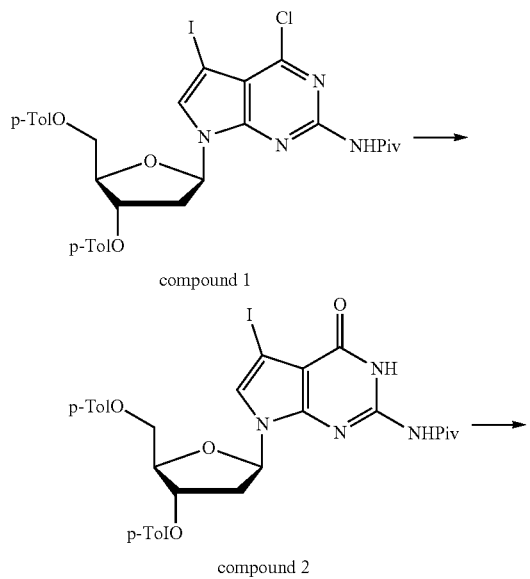

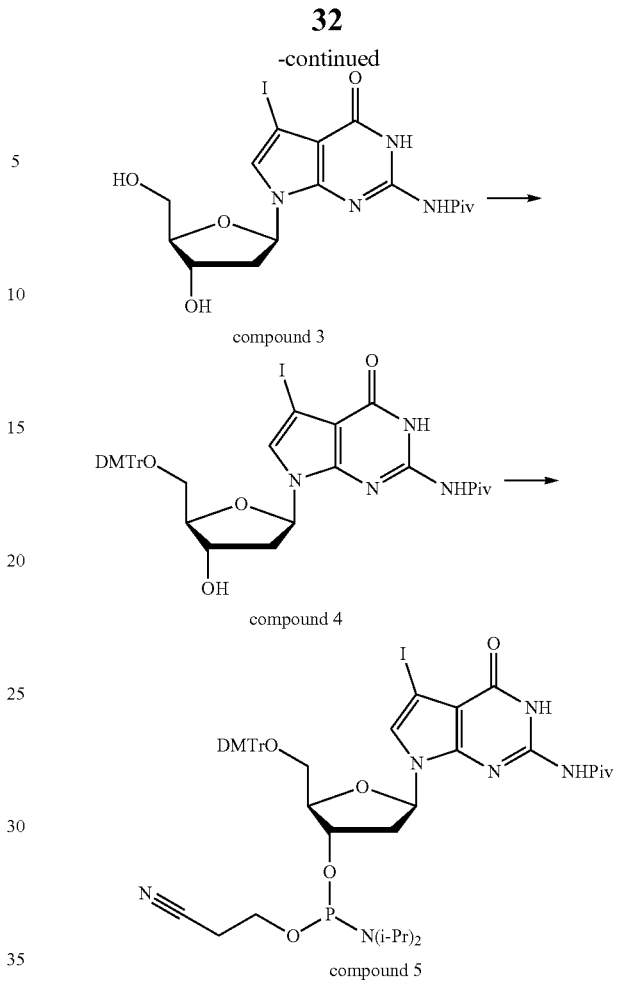

(1) Synthesis of Compound 2

Compound 1 was synthesized according to F. Seela et al., Synthesis, 2004, 8, 1203-1210 and M. Mackova et al., ChemBioChem, 2015, 16, 2225-2236.

Tetramethylguanidine (4.3 mL, 35 mmol) and pyridine-2-aldoxime (4.3 g, 35 mmol) were added to a mixed solution of compound 1 (5.1 g, 7.0 mmol) in DMF/1,4-dioxane (170 mL, DMF:1,4-dioxane=1:1), and the mixture was stirred under a nitrogen atmosphere at room temperature overnight. The mixture was diluted with ethyl acetate, washed successively with 1N aqueous hydrochloric acid solution, saturated aqueous sodium hydrogen carbonate and saturated brine, dried over anhydrous sodium sulfate and concentrated to give a residue. The residue was washed with methanol to give compound 2 (4.9 g) as a white solid.

$^1$H NMR (300 MHz, DMSO-d$^6$) δH: 1.22 (9H, s), 2.38 (3H, s), 2.40 (3H, s), 2.64 (1H, m), 2.91 (1H, m), 4.45-4.62 (3H, m), 5.63 (1H, d, J=5.9 Hz), 6.55 (1H, dd, J=9.1, 5.5 Hz), 7.34-7.41 (5H, m), 7.88-7.94 (4H, m), 10.96 (1H, s), 11.95 (1H, s)

(2) Synthesis of Compound 3

Under ice-cooling, 1N sodium methoxide (12.4 mL, 12.4 mmol) was added to a mixed solution of compound 2 (4.5 g, 6.2 mmol) in THF/methanol (151.5 mL, THF:methanol=150:1.5), and the mixture was stirred under a nitrogen atmosphere under ice-cooling for 15 min. Under ice-cooling, acetic acid (0.8 mL) was added and the mixture was concentrated to give a residue. The residue was purified by silica gel column chromatography (eluent: chloroform/methanol=9/1) to give compound 3 (3.0 g) as a white solid.

$^1$H NMR (300 MHz, DMSO-d$^6$) δH: 1.23 (9H, s), 2.09 (1H, m), 2.36 (1H, m), 3.50 (2H, m), 3.76 (1H, s), 4.29 (1H, s), 4.93 (1H, t, J=5.1 Hz), 5.23 (1H, d, J=3.3 Hz), 6.45 (1H, dd, J=8.1, 5.5 Hz), 7.45 (1H, s), 10.97 (1H, s), 11.90 (1H, s)

(3) Synthesis of Compound 4

Dimethoxytrityl chloride (0.8 g, 2.4 mmol) was added to a solution (15 mL) of compound 3 (1.0 g, 2.2 mmol) in pyridine, and the mixture was stirred under a nitrogen atmosphere, overnight. Methanol was added and the mixture was stirred for 1 hr, diluted with chloroform, washed with saturated aqueous sodium hydrogen carbonate and saturated brine, dried over sodium sulfate and concentrated to give a residue. The residue was purified by silica gel column chromatography (eluent: chloroform/methanol/triethylamine=94/5/1) to give compound 4 (1.3 g) as a white solid.

$^1$H NMR (300 MHz, DMSO-d$^6$) δH: 1.20 (9H, s), 2.15 (1H, m), 2.40 (1H, m), 3.04 (1H, m), 3.13 (1H, m), 3.70 (6H, s), 3.86 (1H, m), 4.27 (1H, m), 5.26 (1H, d, J=3.7 Hz), 6.43 (1H, m), 6.81-6.84 (4H, m), 7.15-7.35 (10H, m), 10.94 (1H, s), 11.90 (1H, s)

(4) Synthesis of Compound 5

2-Cyanoethyl diisopropylchlorophosphoramidite (0.27 mL, 1.2 mmol) was added to a solution (30 mL) of diisopropylethylamine (0.28 mL, 1.7 mmol) and compound 4 (0.5 g, 0.6 mmol) in dichloromethane, and the mixture was stirred under a nitrogen atmosphere for 1 hr, diluted with dichloromethane, washed successively with saturated aqueous sodium hydrogen carbonate and saturated brine, dried over anhydrous sodium sulfate, and concentrated to give a residue. The residue was purified by silica gel column chromatography (eluent: hexane/ethyl acetate/triethylamine=10/9/1) to give the title compound (0.4 g) as a white solid. $^{31}$P NMR (122 MHz, CDCl$_3$) δP: 148.53, 148.91.

Example 28: Synthesis of 7-deaza-7-(2-phenylethynyl) guanosine Derivative

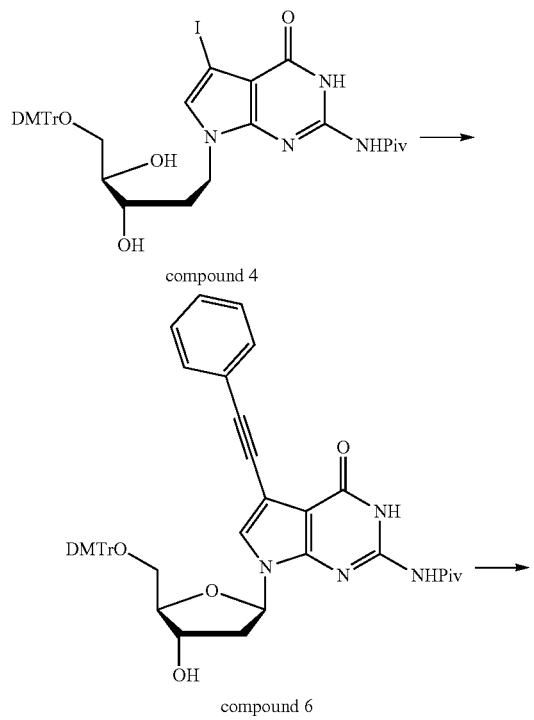

(1) Synthesis of Compound 6

To a solution (5 mL) of copper iodide (6 mg, 0.03 mmol), triethylamine (0.09 mL, 0.6 mmol), ethynylbenzene (0.04 mL, 0.4 mmol) and compound 4 (0.2 g, 0.3 mmol) in acetonitrile was added tetrakis(triphenylphosphine)palladium(0) (35 mg, 0.03 mmol), and the mixture was stirred under a nitrogen atmosphere at 80° C. for 2 hr. The reaction mixture was filtered through celite, and concentrated to give a residue. The residue was purified by silica gel column chromatography (ethyl acetate:triethylamine=98:2) to give the title compound (0.15 g).

$^1$H NMR (300 MHz, CDCl$_3$) δH: 1.30 (9H, s), 1.90 (1H, d, J=3.7 Hz), 2.42 (2H, m), 3.28 (1H, m), 3.40 (1H, m), 3.73 (6H, s), 4.03 (1H, m), 4.55 (1H, m), 6.44 (1H, m), 6.81-6.84 (4H, m), 7.13 (1H, s), 7.17-7.33 (10H, m), 7.41-7.43 (2H, m), 7.50-7.54 (2H, m), 7.91 (1H, s), 11.69 (1H, s)

(2) Synthesis of Compound 7

2-Cyanoethyl diisopropylchlorophosphoramidite (0.16 mL, 0.7 mmol) was added to a solution (20 mL) of diisopropylethylamine (0.15 mL, 1.2 mmol) and compound 6 (0.4 g, 0.5 mmol) in dichloromethane, and the mixture was stirred under a nitrogen atmosphere for 1 hr, diluted with dichloromethane, washed successively with saturated aqueous sodium hydrogen carbonate and saturated brine, dried over anhydrous sodium sulfate and concentrated to give a residue. The residue was purified by silica gel column chromatography (eluent: hexane/ethyl acetate/triethylamine=10/9/1) to give the title compound (0.4 g) as a white solid.

$^{31}$P NMR (162 MHz, CDCl$_3$) δP:148.70, 148.97.

Example 29: Synthesis of 7-deaza-7-[2-(4-pyridyl)ethynyl]guanosine Derivative

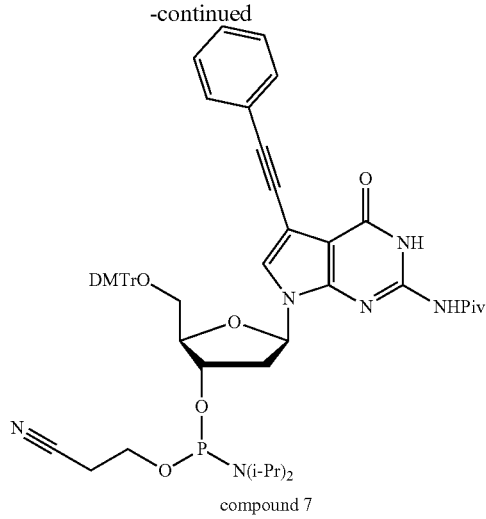

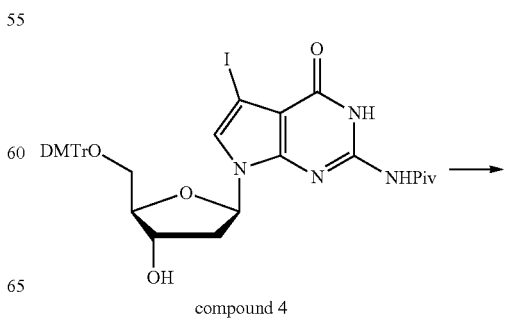

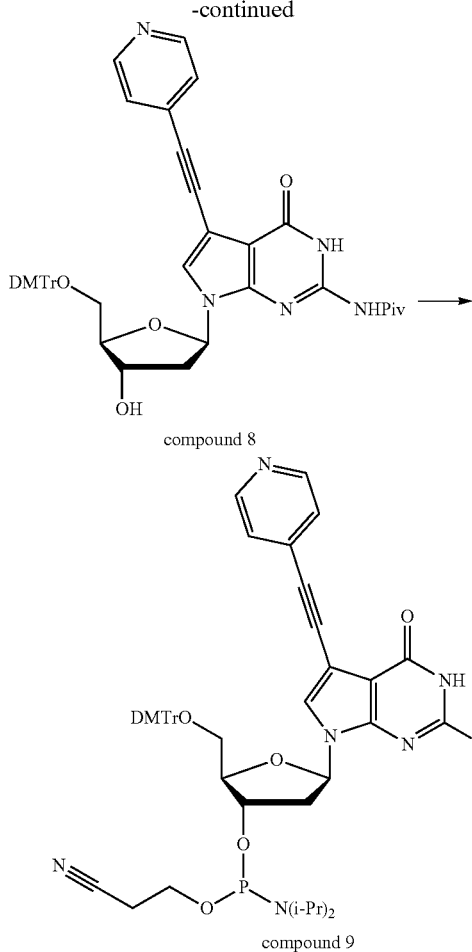

compound 8

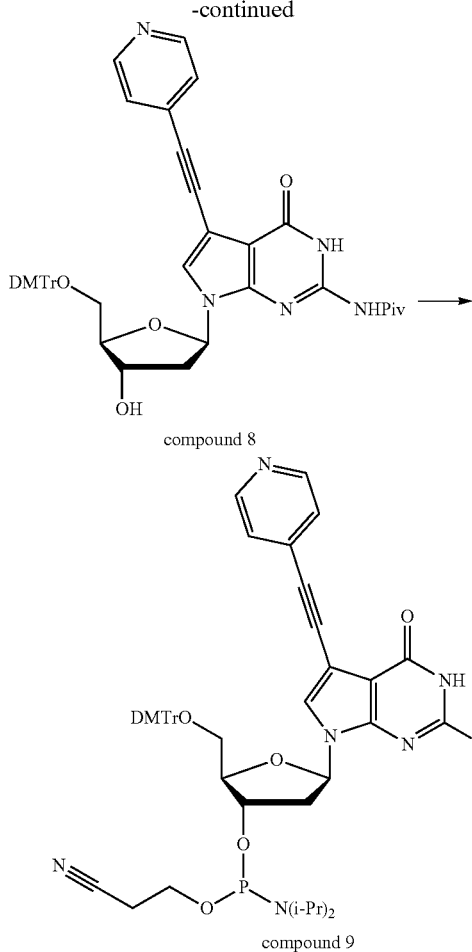

compound 9

(1) Synthesis of Compound 8

To an acetonitrile solution (2.5 mL) containing copper iodide (2 mg, 0.01 mmol), triethylamine (0.04 mL, 0.3 mmol), p-ethynylpyridine (20 mg, 0.2 mmol) and compound 4 (0.1 g, 0.1 mmol) was added tetrakis(triphenylphosphine)palladium(0) (10 mg, 0.01 mmol), and the mixture was stirred under a nitrogen atmosphere at 80° C. for 1 hr. The reaction mixture was filtered through celite and concentrated to give a residue. The residue was purified by silica gel column chromatography (eluent: ethyl acetate/triethylamine=98/2) to give the title compound (0.08 g) as a pale-yellow solid.

$^1$H NMR (300 MHz, CDCl$_3$) δH: 1.31 (9H, s), 2.21 (1H, m), 2.43 (2H, m), 3.30 (1H, m), 3.40 (1H, m), 3.73 (6H, s), 4.06 (1H, m), 4.57 (1H, brs), 6.41 (1H, tr, J=6.6 Hz), 6.80-6.83 (4H, m), 7.28-7.43 (10H, m), 7.17-7.22 (2H, m), 8.14 (1H, s), 8.53-8.55 (2H, m), 11.78 (1H, s)

(2) Synthesis of Compound 9

2-Cyanoethyl diisopropylchlorophosphoramidite (0.15 mL, 0.7 mmol) was added to a solution (30 mL) of diisopropylethylamine (0.3 mL, 1.7 mmol) and compound 8 (0.5 g, 0.7 mmol) in dichloromethane, and the mixture was stirred under a nitrogen atmosphere for 1 hr. The mixture was diluted with dichloromethane, washed successively with saturated aqueous sodium hydrogen carbonate and saturated brine, dried over anhydrous sodium sulfate and concentrated to give a residue. The residue was purified by silica gel column chromatography (eluent: hexane/ethyl acetate/triethylamine=10/9/1) to give the title compound (0.5 g) as a white solid.

$^{31}$P NMR (162 MHz, CDCl$_3$) δP:148.64, 149.07.

Example 30: Synthesis of 7-deaza-7-[2-(acetoxymethyl)ethynyl]guanosine Derivative

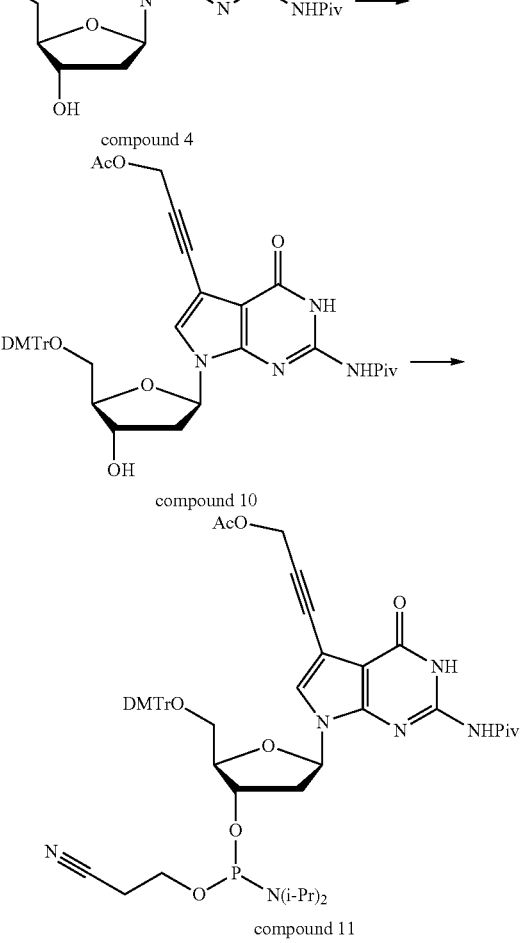

(1) Synthesis of Compound 10

To a solution (2.5 mL) of copper iodide (4 mg, 0.01 mmol), triethylamine (0.09 mL, 0.7 mmol), 1-acetoxy-2-propyne (20 mg, 0.2 mmol) and compound 4 (0.1 g, 0.1 mmol) in acetonitrile was added tetrakis(triphenylphosphine)palladium(0) (22 mg, 0.01 mmol), and the mixture was stirred under a nitrogen atmosphere at 80° C. for 1 hr. The reaction mixture was filtered through celite and concentrated to give a residue. The residue was purified by silica gel column chromatography (eluent: chloroform/methanol/triethylamine=98/1/1) and repurified by amino silica gel silica gel column chromatography (eluent: chloroform/methanol/triethylamine=98/1/1) to give the title compound (0.08 g) as a pale-yellow solid.

$^1$H NMR (300 MHz, CDCl$_3$) δH: 1.28 (9H, s), 2.08 (3H, s), 2.15 (1H, d, J=3.2 Hz), 2.37 (2H, m), 3.24 (1H, m), 3.37 (1H, m), 3.77 (6H, s), 4.01 (1H, m), 4.50 (1H, brs), 4.91 (2H, s), 6.38 (1H, m), 6.80-6.83 (4H, m), 7.07 (1H, s), 7.81-7.41 (9H, m), 8.03 (1H, s), 11.73 (1H, s)

(2) Synthesis of Compound 11

2-Cyanoethyl diisopropylchlorophosphoramidite (0.1 mL, 0.4 mmol) was added to a solution (20 mL) of diisopropylethylamine (0.2 mL, 1.0 mmol) and compound 10 (0.3 g, 0.4 mmol) in dichloromethane, and the mixture was stirred under a nitrogen atmosphere for 1 hr. The mixture was diluted with dichloromethane, washed successively with saturated aqueous sodium hydrogen carbonate and saturated brine, dried over anhydrous sodium sulfate and concentrated to give a residue. The residue was purified by silica gel column chromatography (eluent: hexane/ethyl acetate/triethylamine=10/9/1) to give the title compound (0.3 g) as a white solid.

$^{31}$P NMR (122 MHz, CDCl$_3$) δP: 148.72, 149.0427.

The invention claimed is:

1. A method for reducing hepatotoxicity of an antisense oligonucleic acid, the method comprising
    (1) obtaining or preparing an unmodified antisense oligonucleic acid having a base length of not less than 7 nt and not more than 30 nt, wherein (a) nucleic acid residues of not less than 1 nt and not more than 5 nt respectively from both terminals are 2',4'-bridged nucleic acids and (b) 2',4'-non-bridged nucleic acid residue(s) is(are) present between both terminals,
    (2) obtaining or preparing a modified variant of the unmodified antisense oligonucleic acid, wherein one or more bases in the nucleic acid residue(s) of the 2',4'-non-bridged nucleic acid residue(s) is/are modified,
    (3) measuring serum concentration of AST (aspartate aminotransferase) and ALT (alanine aminotransferase) after administration of the unmodified antisense oligonucleic acid and the modified variant, and
    (4) selecting a modified variant showing reduced serum concentration of AST (aspartate aminotransferase) and ALT (alanine aminotransferase) after administration compared to the unmodified antisense oligonucleic acid to provide an antisense oligonucleic acid with reduced hepatotoxicity.

2. The method according to claim 1, wherein the hepatotoxicity is caused by the interaction with a biomolecule other than the target mRNA.

3. The method according to claim 1, wherein the 2',4'-non-bridged nucleic acid residue with the one or more modified bases is contained in a sequence of TGC or TCC.

4. The method according to claim 1, wherein the one or more modified bases is 5-hydroxycytosine, 4-acetylcytosine, 3-$C_{1-6}$ alkylcytosine, 5-$C_{2-6}$ alkylcytosine, 2-thiocytosine, 2-thiothymine, dihydrothymine, pseudo thymine, 2-thiouridine, 5-(carboxyhydroxymethyl)uridine, 5-carboxymethyl-aminomethyl-2-thiouridine, 5-carboxymethylaminomethyluridine, dihydrouridine, pseudo uridine, 5-methylaminomethyluridine, 5-methylaminomethyl-2-thiouridine, 5-methoxycarbonylmethyl-2-thiouridine, 5-methoxycarbonylmethyluridine, 5-methoxyuridine, 8-aminoguanine, 8-halogenoguanine, 7-deaza-7-(2-phenylethynyl)guanine, 7-deaza-7-(2-pyridylethynyl)guanine, 7-deaza-7-[2-($C_{1-7}$ alkanoyloxy-$C_{1-6}$ alkyl)-ethynyl]guanine, 7-deaza-7-[2-(hydroxy-$C_{1-6}$ alkyl)ethynyl]guanine, 1-$C_{1-6}$ alkylguanine, 2,2-di($C_{1-6}$ alkyl)guanine, 2-$C_{1-6}$ alkylguanine, 7-deaza-7-$C_{1-6}$ alkylguanine, 7-deaza-7-$C_{2-6}$ alkenylguanine, 7-deaza-7-$C_{2-6}$ alkynylguanine, 7-deaza-7-halogenoguanine, inosine, 1-$C_{1-6}$ alkylinosine, queuosine, β,D-galactosylqueuosine, β,D-mannosylqueuosine, $N^6$—$C_{2-6}$ alkenyladenine, 1-$C_{1-6}$ alkyladenine, 2-$C_{1-6}$ alkyladenine, $N^6$—$C_{1-6}$ alkyladenine, or 2-$C_{1-6}$ alkylthio-$N^6$—$C_{2-6}$ alkenyladenine.

5. The method according to claim 4, wherein the one or more modified bases is 7-deaza-7-(2-phenylethynyl)guanine, 7-deaza-7-[2-(4-pyridyl)ethynyl]guanine, 7-deaza-7-[2-(2-pyridyl)ethynyl]-guanine, 7-deaza-7-[2-(3-pyridyl)ethynyl]guanine, 7-deaza-7-[2-($C_{1-7}$ alkanoyloxy-$C_{1-6}$ alkyl)ethynyl]guanine, 7-deaza-7-[2-(hydroxy-$C_{1-6}$ alkyl)ethynyl]guanine, 7-deaza-7-$C_{1-6}$ alkylguanine, 7-deaza-7-$C_{2-6}$ alkenylguanine, 7-deaza-7-$C_{2-6}$ alkynylguanine, or 7-deaza-7-halogenoguanine.

6. The method according to claim 1, wherein the 2',4'-non-bridged nucleic acid residue is DNA.

7. The method according to claim 1, wherein the 2',4'-bridged nucleic acid residue has a structure of any of the following formulas (I) to (III):

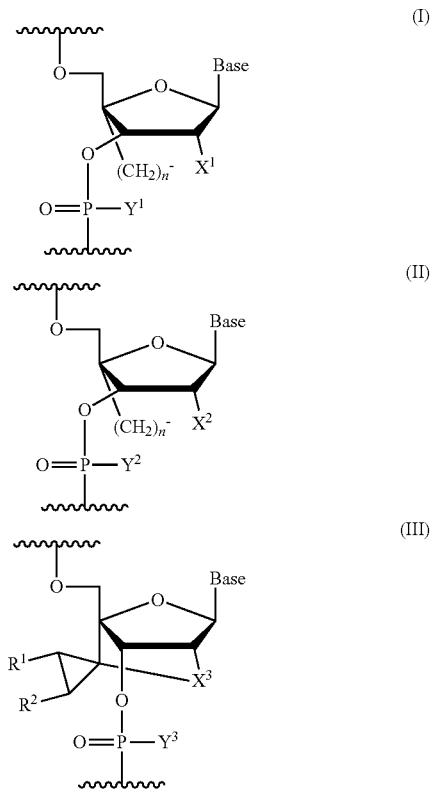

wherein
$X^1$ is O, S, a >N($R^3$) group, a —C(=O)—O— group or a —C(=O)—N($R^4$)— group ($R^3$ and $R^4$ are each independently H or a $C_{1-6}$ alkyl group),
$X^2$ is a guanidino group represented by any of the following formulas (IV) to (VII):

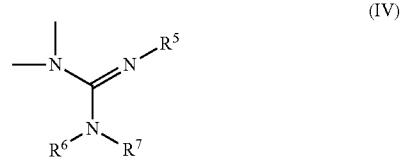

-continued

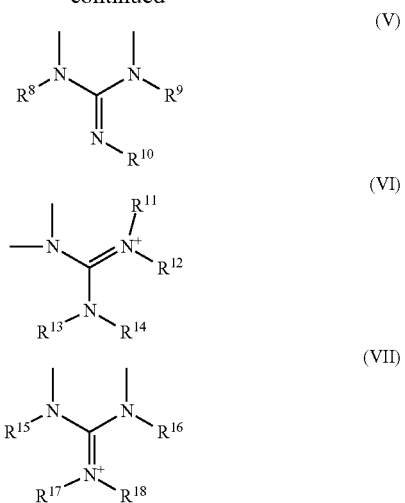

wherein R$^5$-R$^{18}$ are each independently H, a C$_{1-6}$ alkyl group, a C$_{3-10}$ cycloalkyl group, an amino-protecting group or a 2-cyanoethyloxycarbonyl group, X$^3$ is O, S, a >N(R$^{19}$) group, a —C(=O)—O— group or a —C(=O)—N(R$^{20}$)— group (R$^{19}$ and R$^{20}$ are each independently H or a C$_{1-6}$ alkyl group), Y$^1$-Y$^3$ are each independently O$^-$ or S$^-$, Base is a nucleic acid base group, R$^1$ and R$^2$ are each independently H, a C$_{1-6}$ alkyl group or R$^1$ and R$^2$ may be taken together to form a C$_{1-4}$ alkylene group, and n is an integer of not less than 0 and not more than 2.

8. The method according to claim 7, wherein the 2',4'-bridged nucleic acid residue has a structure of the formula (I), X$^1$ is O and n is 1.

9. A production method of an antisense oligonucleic acid showing reduced hepatotoxicity, the method comprising (1) obtaining or preparing an unmodified antisense oligonucleic acid having a base length of not less than 7 nt and not more than 30 nt, wherein (a) nucleic acid residues of not less than 1 nt and not more than 5 nt respectively from both terminals are 2',4'-bridged nucleic acids and (b) 2',4'-non-bridged nucleic acid residue(s) is(are) present between both terminals, (2) preparing a modified variant of the unmodified antisense oligonucleic acid, wherein one or more bases in the nucleic acid residue(s) of the 2',4'-non-bridged nucleic acid residue(s) is/are modified, (3) measuring serum concentration of AST (aspartate aminotransferase) and ALT (alanine aminotransferase) after administration of the unmodified antisense oligonucleic acid and the modified variant, and (4) selecting a modified variant showing reduced serum concentration of AST (aspartate aminotransferase) and ALT (alanine aminotransferase) after administration compared to the unmodified antisense oligonucleic acid to provide an antisense oligonucleic acid with reduced hepatotoxicity.

10. The production method according to claim 9, wherein the hepatotoxicity is caused by the interaction with a biomolecule other than the target mRNA.

11. The production method according to claim 9, wherein the 2',4'-non-bridged nucleic acid residue with the one or more modified bases is contained in a sequence of TGC or TCC.

12. The production method according to claim 9, wherein the one or more modified bases is 5-hydroxycytosine, 4-acetylcytosine, 3-C$_{1-6}$ alkylcytosine, 5-C$_{2-6}$ alkylcytosine, 2-thiocytosine, 2-thiothymine, dihydrothymine, pseudo thymine, 2-thiouridine, 5-(carboxyhydroxymethyl)uridine, 5-carboxymethylaminomethyl-2-thiouridine, 5-carboxymethylaminomethyluridine, dihydrouridine, pseudo uridine, 5-methylaminomethyluridine, 5-methylaminomethyl-2-thiouridine, 5-methoxycarbonylmethyl-2-thiouridine, 5-methoxycarbonylmethyluridine, 5-methoxyuridine, 8-aminoguanine, 8-halogenoguanine, 7-deaza-7-(2-phenylethynyl)guanine, 7-deaza-7-(2-pyridylethynyl)guanine, 7-deaza-7-[2-(C$_{1-7}$ alkanoyloxy-C$_{1-6}$ alkyl)-ethynyl]guanine, 7-deaza-7-[2-(hydroxy-C$_{1-6}$ alkyl)ethynyl]guanine, 1-C$_{1-6}$ alkylguanine, 2,2-di(C$_{1-6}$ alkyl)guanine, 2-C$_{1-6}$ alkylguanine, 7-deaza-7-C$_{1-6}$ alkylguanine, 7-deaza-7-C$_{2-6}$ alkenylguanine, 7-deaza-7-C$_{2-6}$ alkynylguanine, 7-deaza-7-halogenoguanine, inosine, 1-C$_{1-6}$ alkylinosine, queuosine, β,D-galactosylqueuosine, β,D-mannosylqueuosine, N$^6$—C$_{2-6}$ alkenyladenine, 1-C$_{1-6}$ alkyladenine, 2-C$_{1-6}$ alkyladenine, N$^6$—C$_{1-6}$ alkyladenine, or 2-C$_{1-6}$ alkylthio-N$^6$—C$_{2-6}$ alkenyladenine.

13. The production method according to claim 12, wherein the one or more modified bases is 7-deaza-7-(2-phenylethynyl)guanine, 7-deaza-7-[2-(4-pyridyl)ethynyl]guanine, 7-deaza-7-[2-(2-pyridyl)ethynyl]-guanine, 7-deaza-7-[2-(3-pyridyl)ethynyl]guanine, 7-deaza-7-[2-(C$_{1-7}$ alkanoyloxy-C$_{1-6}$ alkyl)ethynyl]guanine, 7-deaza-7-[2-(hydroxy-C$_{1-6}$ alkyl)ethynyl]guanine, 7-deaza-7-C$_{1-6}$ alkylguanine, 7-deaza-7-C$_{2-6}$ alkenylguanine, 7-deaza-7-C$_{2-6}$ alkynylguanine, or 7-deaza-7-halogenoguanine.

14. The production method according to claim 9, wherein the 2',4'-non-bridged nucleic acid residue is DNA.

15. The production method according to claim 9, wherein the 2',4'-bridged nucleic acid residue has a structure of any of the following formulas (I) to (III):

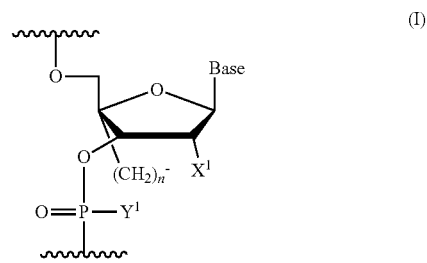

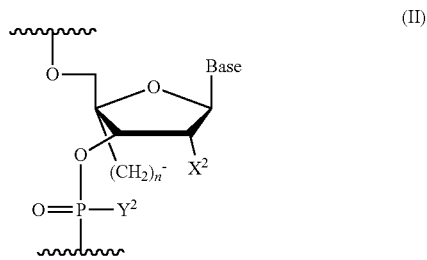

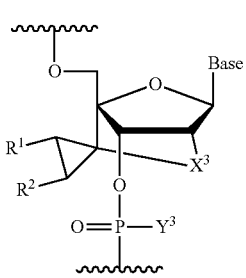

(III)

wherein $X^1$ is O, S, a >N($R^3$) group, a —C(=O)—O— group or a —C(=O)—N($R^4$)— group ($R^3$ and $R^4$ are each independently H or a $C_{1-6}$ alkyl group), $X^2$ is a guanidino group represented by any of the following formulas (IV) to (VII):

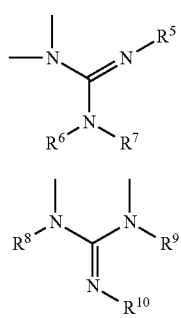

(IV)

(V)

(VI)

(VII)

wherein $R^5$-$R^{18}$ are each independently H, a $C_{1-6}$ alkyl group, a $C_{3-10}$ cycloalkyl group, an amino-protecting group or a 2-cyanoethyloxycarbonyl group, $X^3$ is O, S, a >N($R^{19}$) group, a —C(=O)—O— group or a —C(=O)—N($R^{20}$)— group ($R^{19}$ and $R^{20}$ are each independently H or a $C_{1-6}$ alkyl group), $Y^1$-$Y^3$ are each independently $O^-$ or $S^-$, Base is a nucleic acid base group, $R^1$ and $R^2$ are each independently H, a $C_{1-6}$ alkyl group or $R^1$ and $R^2$ may be taken together to form a $C_{1-4}$ alkylene group, and n is an integer of not less than 0 and not more than 2.

16. The production method according to claim 15, wherein the 2',4'-bridged nucleic acid residue has a structure of the formula (I), $X^1$ is O and n is 1.

* * * * *